(12) United States Patent
Li

(10) Patent No.: US 7,521,461 B2
(45) Date of Patent: Apr. 21, 2009

(54) BENZOIC ACID DERIVATIVES AS MODULATORS OF PPAR ALPHA AND GAMMA

(75) Inventor: Lanna Li, Molndal (SE)

(73) Assignee: AstraZeneca AB, Sodertalje (SE)

( * ) Notice: Subject to any disclaimer, the term of this patent is extended or adjusted under 35 U.S.C. 154(b) by 375 days.

(21) Appl. No.: 10/518,819

(22) PCT Filed: Jun. 17, 2003

(86) PCT No.: PCT/GB03/02598

§ 371 (c)(1),
(2), (4) Date: Dec. 20, 2004

(87) PCT Pub. No.: WO04/000295

PCT Pub. Date: Dec. 31, 2003

(65) Prior Publication Data

US 2005/0267149 A1   Dec. 1, 2005

(30) Foreign Application Priority Data

Jun. 20, 2002   (SE) .................................... 0201937

(51) Int. Cl.
  A61K 31/47    (2006.01)
  A61K 31/44    (2006.01)
  A61K 31/426   (2006.01)
  A61K 31/4172  (2006.01)
  A61K 31/195   (2006.01)
  C07C 229/38   (2006.01)

(52) U.S. Cl. .................. 514/307; 514/357; 514/365; 514/397; 514/567; 546/146; 546/335; 548/200; 548/341.1; 562/442

(58) Field of Classification Search ............. 514/307, 514/357, 365, 397, 567; 546/146, 335; 548/200, 548/341.1; 562/442
See application file for complete search history.

(56) References Cited

U.S. PATENT DOCUMENTS

| | | | |
|---|---|---|---|
| 4,113,871 A | 9/1978 | Stach et al. | |
| 5,334,753 A | 8/1994 | Bennetau et al. | |
| 5,750,783 A | 5/1998 | Goldmann et al. | |
| 5,922,767 A * | 7/1999 | Kanamaru et al. | 514/596 |
| 6,258,850 B1 | 7/2001 | Andersson | |
| 6,306,854 B1 | 10/2001 | Brown et al. | |
| 2002/0022656 A1 | 2/2002 | Sauerberg et al. | |

FOREIGN PATENT DOCUMENTS

| | | |
|---|---|---|
| DE | 198 25 804 A1 | 12/1999 |
| EP | 802186 | 4/1997 |
| EP | 0 803 186 | 10/1997 |
| EP | 1184366 | 3/2002 |
| JP | 10072371 | 3/1998 |
| WO | WO-99/20275 A2 | 4/1999 |
| WO | 9932477 | 7/1999 |
| WO | 0064876 | 11/2000 |
| WO | 0064888 | 11/2000 |
| WO | WO-01/12187 A2 | 2/2001 |
| WO | 04000295 | 12/2003 |

OTHER PUBLICATIONS

Patani et al. "Bioisosterism: A Rational Approach in Drug Design" Chemical Reviews, 1996, vol. 96, pp. 3147-3176.*
Harshad K. Rami et al., "Synthetic ligands for PPARγ—review of patent literature 1994-1999," Expert Opinion on Therapeutic Patents 10(5):623-634 (2000).
Notice of Allowance dated Nov. 15, 2007 cited in copending U.S. Appl. No. 10/519,376.
Office Action dated May 3, 2007 cited in copending U.S. Appl. No. 10/519,376.
Notice of copending applications.
Quick "The relationship between chemical structure and physiological response," The Journal of Biological Chemistry (1932) 157-169.

* cited by examiner

Primary Examiner—Rei-Tsang Shiao
Assistant Examiner—Joseph R Kosack
(74) Attorney, Agent, or Firm—Pepper Hamilton LLP

(57) ABSTRACT

A compound of formula (I) wherein $R^1$ represents aryl optionally substituted by a heterocyclic group or a heterocyclic group optionally substituted by aryl wherein each aryl or heterocyclic group is optionally substituted; the group —$(CH_2)_m$-T-$(CH_2)_n$—U—$(CH_2)_p$— is attached at either the 3 or 4 position in the phenyl ring as indicated by the numbers in formula (I) and represents a group selected from one or more of the following: $O(CH_2)_2$, $O(CH_2)_3$, $NC(O)NR^4(CH_2)_2$, $CH_2S(O_2)NR^5(CH_2)_2$, $CH_2N(R^6)C(O)CH_2$, $(CH_2)_2N(R^6)C(O)(CH_2)_2$, $C(O)NR^7CH_2$, $C(O)NR^7(CH_2)_2$, and $CH_2N(R^6)C(O)CH_2O$; V represents O, S, $NR^8$ or a single bond; q represents 1, 2, or 3; W represents O, S, $N(R^9)C(O)$, $NR^{10}$, or a single bond; $R^2$ represents halo, a $C_{1-4}$ alkyl group which is optionally substituted by one or more fluoro, a $C_{1-4}$ alkoxy group which is optionally substituted by one or more fluoro, a $C_{1-4}$ acyl group, aryl, an aryl $C_{1-4}$ alkyl group, CN or $NO_2$; r represents 0, 1, 2 or 3; $R^3$ halo, a $C_{1-4}$ alkyl group which is optionally substutited by one or more fluoro, a $C_{1-4}$ alkoxy group which is optionally substituted by one or more fluoro, a $C_{1-4}$ acyl group, aryl, an aryl $C_{1-4}$ alkyl group, or CN; s represents 0, 1, 2 or 3; and $R^4$, $R^5$, $R^6$, $R^7$, $R^8$, $R^9$, and $R^{10}$ independently represent H, a $C_{1-10}$ alkyl group, aryl or an aryl $C_{1-4}$ alkyl group or when m is O and T represents a group $N(R^6)C(O)$ or a group $(R^5)NS(O_2)$ then $R^1$ and $R^6$ or $R^1$ and $R^5$ together with the nitrogen atom to which they are attached represent a heteroaryl group; with provisos and pharmaceutically acceptable salts thereof, processes for preparing such compounds, their utility in treating clinical conditions associated with insulin resistance, methods for their therapeutic use and pharmaceutical compositions containing them.

10 Claims, No Drawings

BENZOIC ACID DERIVATIVES AS MODULATORS OF PPAR ALPHA AND GAMMA

This application is a national stage filing under 35 U.S.C. 371 of PCT application PCT/GB2003/002598 filed Jun. 17, 2003, which claims priority from Sweden Application No. 0201937-0, filed Jun. 20, 2001, the specifications of each of which are incorporated by reference herein.

FIELD OF THE INVENTION

The present invention relates to certain novel benzoic acid derivatives, to processes for preparing such compounds, to their utility in treating clinical conditions associated with insulin resistance, to methods for their therapeutic use and to pharmaceutical compositions containing them

BACKGROUND OF THE INVENTION

The Insulin Resistance Syndrome (IRS) including type 2 diabetes mellitus, which refers to a cluster of manifestations including insulin resistance with accompanying hyperinsulinaemia, possible type 2 diabetes mellitus, arterial hypertension, central (visceral) obesity, dyslipidaemia observed as deranged lipoprotein levels typically characterised by elevated VLDL (very low density lipoproteins), small dense LDL particles and reduced HDL (high density lipoprotein) concentrations and reduced fibrinolysis.

Recent epidemiological research has documented that individuals with insulin resistance run a greatly increased risk of cardiovascular morbidity and mortality, notably suffering from myocardial infarction and stroke. In type 2 diabetes mellitus atherosclerosis related conditions cause up to 80% of all deaths.

In clinical medicine there is awareness of the need to increase the insulin sensitivity in IRS suffering patients and thus to correct the dyslipidaemia which is considered to cause the accelerated progress of atherosclerosis. However, currently this is not a universally well defined disease.

Compounds which are modulators of peroxisome proliferator-activated receptors (PPAR, for a review of the PPARs see T. M. Willson et al, J Med Chem 2000, Vol 43, 527) are effective in treating conditions associated with insulin resistance.

Surprisingly a series of compounds has now been found which are modulators of PPARα and/or PPARγ activity.

DESCRIPTION OF THE INVENTION

The present invention provides a compound of formula I

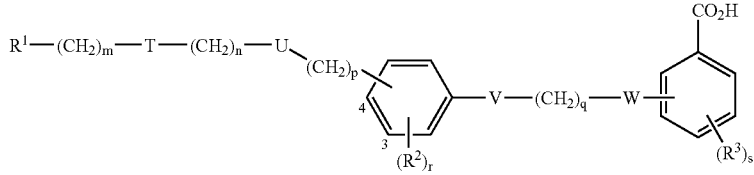

wherein $R^1$ represents aryl optionally substituted by a heterocyclic group or a heterocyclic group optionally substituted by aryl wherein each aryl or hetero cyclic group is optionally substituted by one or more of the following groups:
a $C_{1-6}$alkyl group;
a $C_{1-6}$acyl group;
aryl$C_{1-6}$alkyl, wherein the alkyl, aryl, or alkylaryl group is optionally substituted by one or more $R^b$;
halogen,
—CN and $NO_2$,
—$NR^cCOOR^a$;
—$NR^cCOR^a$;
—$NR^cR^a$;
—$NR^cSO_2R^d$;
—$NR^cCONR^kR^c$;
—$NR^cCSNR^aR^k$;
—$OR^a$;
—$OSO_2R^d$;
—$SO_2R^d$;
—$SOR^d$;
—$SR^c$;
—$SO_2NR^aR^f$;
—$SO_2OR^a$;
—$CONR^cR^a$;
—$OCONR^fR^a$;
wherein $R^a$ represents H, a $C_{1-6}$alkyl group, aryl or aryl$C_{1-6}$alkyl group wherein the alkyl, aryl or aryl$C_{1-6}$alkyl group is optionally substituted one or more times by $R^b$, wherein $R^b$ represents $C_{1-6}$alkyl, aryl, aryl$C_{1-6}$alkyl, cyano, —$NR^cR^d$, =O, halo, —OH, —SH, —$OC_{1-4}$alkyl, —Oaryl, —$OC_{1-4}$alkylaryl, —$COR^c$, —$SR^d$, —$SOR^d$, or —$SO_2R^d$, wherein $R^c$ represents H, $C_{1-4}$alkyl, aryl, aryl$C_{1-4}$alkyl and $R^d$ represents $C_{1-4}$alkyl, aryl, aryl$C_{1-4}$alkyl;
wherein $R^f$ represents hydrogen, $C_{1-4}$alkyl, $C_{1-4}$acyl, aryl, aryl$C_{1-4}$alkyl and $R^a$ is as defined above; and
$R^k$ represents hydrogen, $C_{1-4}$alkyl, aryl, aryl$C_{1-4}$alkyl;
the group —$(CH_2)_m$-T-$(CH_2)_n$—U—$(CH_2)_p$— is attached at either the 3 or 4 position in the phenyl ring as indicated by the numbers in formula I and represents a group selected from one or more of the following: $O(CH_2)_2$, $O(CH_2)_3$, $NC(O)NR^4(CH_2)_2$, $CH_2S(O_2)NR^5(CH_2)_2$, $CH_2N(R^6)C(O)CH_2$, $(CH_2)_2N(R^6)C(O)(CH_2)_2$, $C(O)NR^7 CH_2$, $C(O)NR^7(CH_2)_2$, and $CH_2N(R^6)C(O)CH_2O$;
V represents O, S, $NR^8$, or a single bond;
q represents 1, 2 or 3;
W represents O, S, $N(R^9)C(O)$, $NR^{10}$, or a single bond;
$R^2$ represents halo, a $C_{1-4}$alkyl group which is optionally substituted by one or more fluoro, a $C_{1-4}$alkoxy group which is optionally substituted by one or more fluoro, a $C_{1-4}$acyl group, aryl, an aryl$C_{1-4}$alkyl group, CN or $NO_2$;
r represents 0, 1, 2 or 3;

$R^3$ represents halo, a $C_{1-4}$alkyl group which is optionally substituted by one or more fluoro, a $C_{1-4}$alkoxy group which is optionally substituted by one or more fluoro, a $C_{1-4}$acyl group, aryl, an aryl$C_{1-4}$alkyl group, or CN;

s represents 0, 1, 2 or 3; and $R^4$, $R^5$, $R^6$, $R^7$, $R^8$, $R^9$ and $R^{10}$ independently represent H, a $C_{1-10}$alkyl group, aryl or an aryl$C_{1-4}$alkyl group or when m is 0 and T represents a group $N(R^6)C(O)$ or a group $(R^5)NS(O_2)$ then $R^1$ and $R^6$ or $R^1$ and $R^5$ together with the nitrogen atom to which they are attached represent a heteroaryl group;

and pharmaceutically acceptable salts thereof;

with the provisos that when 1) when $R^1$ is phenyl optionally substituted by one or two groups independently selected from halo, a $C_{1-4}$alkyl group which is optionally substituted by one or more fluoro, a $C_{1-4}$alkoxy group which is optionally substituted by one or more fluoro;

m is 1;

T is $N(R^6)C(O)$ wherein $R^6$ represents a $C_{2-8}$alkyl group which is optionally interrupted by oxygen;

n is 1;

U is absent or represents methylene;

p is 0;

r is 0;

V is O or S;

q is 1; and

W is a single bond attached to the position ortho to the carboxylic acid group; then s does not represent 0; and 2) when $R^1$ is phenyl optionally substituted by one or two groups independently selected from halo, a $C_{1-4}$alkyl group which is optionally substituted by one or more fluoro, a $C_{1-4}$alkoxy group which is optionally substituted by one or more fluoro;

m is 1;

T is $N(R^6)C(O)$ wherein $R^6$ represents an unbranched $C_{2-7}$alkyl group;

n is 1;

U is O;

p is 0;

r is 0 or 1;

and when r is 1 $R^2$ is attached at the 3 position and is $OCH_3$;

V is a single bond;

q is 2; and

W is O or S attached to the position ortho to the carboxylic acid group;

then s does not represent 0.

Examples of $C_{1-6}$alkyl include methyl, ethyl, n-propyl, isopropyl, n-butyl, iso-butyl, sec-butyl, t-butyl and straight- and branched-chain pentyl and hexyl as well as cyclopropyl, cyclobutyl, cyclopentyl and cyclohexyl. Preferred alkyl groups are methyl, ethyl, propyl, isopropyl and tertiary butyl.

Unless otherwise stated or indicated, the term "halogen" shall mean fluorine, chlorine, bromine or iodine, preferably fluorine.

Unless otherwise stated or indicated, the term "aryl" denotes a substituted or unsubstituted phenyl or a fused ring system such as naphthyl Unless otherwise stated or indicated, the term "a heterocyclic group" is a saturated, partially saturated or unsaturated, mono or bicyclic ring containing 4-12 atoms of which at least one atom is chosen from nitrogen, sulphur or oxygen, which may, unless otherwise specified, be carbon or nitrogen linked, wherein a —$CH_2$— group can optionally be replaced by a —C(O)— and a ring sulphur atom may be optionally oxidised to form the S-oxide(s). Examples and suitable values of the term "heterocyclic group" are morpholino, piperidyl, pyridyl, pyranyl, pyrrolyl, imidazolyl, thiazolyl, indolyl, quinolyl, isoquinolyl, thienyl, 1,3-benzodioxolyl, 1,3-dioxolanyl, thiadiazolyl, piperazinyl, isothiazolidinyl, 1,3,4-triazolyl, tetrazolyl, pyrrolidinyl, 2-oxazolidinonyl, 5-isoxazolonyl, benz-3-azepinyl, 1,4-benzodioxanyl, thiomorpholino, pyrrolinyl, homopiperazinyl, 3,5-dioxapiperidinyl, 3-pyrazolin-5-onyl tetrahydropyranyl, benzimidazolyl, benzthiazolyl, imidazo[1,2-a]pyridyl, pyrimidyl, pyrazinyl, pyridazinyl, isoxazolyl, 4-pyridone, 1-isoquinolone, 2-pyrrolidone, 4-thiazolidone, dihydroisoquinol-2 (1H)-yl, 2,3-dihydro-1,5-benzothiazepin-4(5H)-one. Preferably a "heterocyclic group" is pyridyl, imidazolyl, thiazolyl, quinolyl, thienyl, 1,3-benzodioxolyl, 1,3-dioxolanyl, isothiazolidinyl 1,3,4-triazolyl, tetrazolyl, 2-oxazolidinonyl, 5-isoxazolonyl, benz-3-azepinyl, hydantoinyl, 1,4-benzodioxanyl, thiomorpholino, 3-pyrazolin-5-onyl, benzimidazolyl, benzthiazolyl, imidazo[1,2-a]pyridyl, pyrimidyl, pyrazinyl, and 2,3-dihydro-1,5-benzothiazepin-4(5H)-one.

Further values of $R^1$, T, U, V, W, $R^2$, $R^3$, m, n, p, q, r and s in compounds of Formula I now follow. It will be understood that such values may be used with any of the definitions, claims or embodiments defined hereinbefore or hereinafter.

In a first aspect $R^1$ represents phenyl which is optionally substituted by one or more of the following: halo, hydroxy, a $C_{1-4}$alkyl group which is optionally substituted by one or more fluoro, a $C_{1-4}$alkoxy group which is optionally substituted by one or more fluoro, benzyloxy, a $C_{1-4}$alkylsulphonyloxy group, phenyl or a heteroaryl group, or $R^1$ represents a heterocyclic group which is optionally substituted by one or more of the following: halo, a $C_{1-4}$alkyl group which is optionally substituted by one or more fluoro, a $C_{1-4}$alkoxy group which is optionally substituted by one or more fluoro or phenyl optionally substituted by one or more of the following: halo, a $C_{1-4}$alkyl group which is optionally substituted by one or more fluoro, a $C_{1-4}$alkoxy group which is optionally substituted by one or more fluoro. In particular $R^1$ represents phenyl, furyl, pyridyl or thiazolyl each of which is optionally substituted by on or more of the following: halo (particularly fluoro), a $C_{1-4}$alkyl group, trifluoromethyl, a $C_{1-4}$alkoxy group, methanesulphonyloxy, hydroxy, benzyloxy, imidazolyl or phenyl.

In a second aspect the group —$(CH_2)_m$-T-$(CH_2)_n$—U—$(CH_2)_p$— is attached at the 4 position in the phenyl ring as indicated by the numbers in formula I , that is para to the group V.

In a third aspect the group —V—$(CH_2)_q$—W— represents a group selected from one or more of the following: $OCH_2$, $SCH_2$, $NHCH_2$, $CH_2CH_2S$ or $CH_2CH_2O$.

In a fourth aspect the group —V—$(CH_2)_q$—W— represents the group $OCH_2$.

In a fifth aspect the group —V—$(CH_2)_q$—W— is joined at the ortho position with respect to the carboxylic acid group.

In a sixth aspect $R^2$ is halo, a $C_{1-4}$alkyl group or a $C_{1-4}$alkoxy group and r is 0 or 1.

In a seventh aspect s is 0.

It will be appreciated by those skilled in the art that certain compounds of formula I may contain an optically active centre and therefore can exist as enantiomers which can be separated as described later. It is expected that most, if not all, of the activity of the compounds of formula I resides in one enantiomer: either the S or the R enantiomer or the (+) or the (−) enantiomer. The enantiomers which are more active in the assays which are described later are preferred forms of the present invention. It will be understood that the present invention includes all mixtures of this active enantiomer with the other enantiomer, for example the racemic mixture.

The active enantiomers may be isolated by separation of racemate for example by fractional crystallization, resolution or HPLC on a chiral column (for example a Chiralpak™ AD 250×50 column). Alternatively the active enantiomers may be made by chiral synthesis from chiral starting materials under conditions which will not cause racemisation or epimerisation, or by derivatisation with a chiral reagent.

Prodrugs of the compounds of formula I also form part of the present invention. The term "prodrug" as used in this specification includes derivatives of the carboxylic acid group which are converted in a mammal, particularly a human, into the carboxylic acid group or a salt or conjugate thereof. It should be understood that, whilst not being bound by theory, it is believed that most of the activity associated with the prodrugs arises from the activity of the compound of formula I into which the prodrugs are converted. Prodrugs can be prepared by routine methodology well within the capabilities of someone skilled in the art. Various prodrugs of carboxy are known in the art. For examples of such prodrug derivatives, see:
a) Design of Prodrugs, edited by H. Bundgaard, (Elsevier, 1985) and Methods in Enzymology. 42: 309-396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113-191 (1991);
c) H. Bundgaard, Advanced Drug Delivery Reviews, 8:1-38 (1992);
d) H. Bundgaard, et al., Journal of Pharmaceutical Sciences, 77:285 (1988); and
e) N. Kakeya, et al., Chem Pharm Bull, 32:692 (1984).

The above documents a to e are herein incorporated by reference.

In vivo cleavable esters are just one type of prodrug of the parent molecule.

The compounds of formula I have activity as medicaments. In particular the compounds of formula I are selective agonists of either PPARα or PPARγ, particularly of PPARα, or are agonists of PPARα and PPARγ. The term agonists as used herein, includes partial agonists.

The present invention provides one or more compounds selected from
3-{[(3-{[(1,1'-biphenyl-4-ylcarbonyl)amino] methyl}phenyl)amino]methyl}benzoic acid;
2-{[4-(2-oxo-2-{[4-(trifluoromethyl)benzyl]amino}ethyl) phenoxy]methyl}benzoic acid;
2-[(3-{2-[benzyl(hexyl)amino]-2-oxoethyl}phenoxy)methyl]benzoic acid;
2-{[3-(2-oxo-2-{[4-(trifluoromethyl)benzyl]amino}ethyl) phenoxy]methyl}benzoic acid;
2-[(4-{3-[[2-(3,4-dimethoxyphenyl)ethyl](methyl)amino]-3-oxopropyl}phenoxy)-methyl]benzoic acid;
2-[(4-{2-[({4-methyl-2-[4-(trifluoromethyl)phenyl]-1,3-thiazol-5-yl}carbonyl)amino]-ethyl}phenoxy)methyl] benzoic acid;
2-({4-[2-({[(2,4-difluorophenyl)amino]carbonyl}amino) ethyl]phenoxy}methyl)benzoic acid;
2-[(4-{2-[(2-methyl-5-phenyl-3-furoyl)amino] ethyl}phenoxy)methyl]benzoic acid;
2-[(4-{2-[(benzylsulfonyl)amino]ethyl}phenoxy)methyl] benzoic acid;
2-[(4-{2-[benzyl(hexyl)amino]-2-oxoethyl}-2-fluorophenoxy)methyl]benzoic acid;
2-[(4-{2-[benzyl(hexyl)amino]-2-oxoethyl}-2-methoxyphenoxy)methyl]benzoic acid;
2-({4-[3-(3,4-dihydroisoquinolin-2 (1H)-yl)-3-oxopropyl] phenoxy}methyl)benzoic acid;
2-[(4-{2-[4-(1H-imidazol-1-yl)phenoxy]ethyl}-phenoxymethyl]benzoic acid;
2-{[4-(2-{4-[(methylsulfonyl)oxy]phenoxy}ethyl)phenoxy] methyl}benzoic acid;
2-[(3-{2-[4-(benzyloxy)phenoxy]ethyl}phenoxy)methyl] benzoic acid;
2-{[3-(2-{4-[(methylsulfonyl)oxy]phenoxy}ethyl)phenoxy] methyl}benzoic acid;
2-({3-[2-(4-hydroxyphenoxy)ethyl]phenoxy}methyl)benzoic acid;
2-[(4-{3-[4-(benzyloxy)phenoxy]propyl}phenoxy)methyl] benzoic acid;
2-{[4-(3-{4-[(methylsulfonyl)oxy]phenoxy}propyl)phenoxy]methyl}benzoic acid;
2-({4-[3-(4-hydroxyphenoxy)propyl]phenoxy}methyl)benzoic acid;
2-{[4-(3-{[2-(2-ethoxyphenyl)ethyl]amino}-3-oxopropyl) phenoxy]methyl}benzoic acid;
2-[(4-{3-[ethyl(2-pyridin-2-ylethyl)amino]-3-oxopropyl}phenoxy)methyl]benzoic acid;
2-{[2-(3-{2-[benzyl(hexyl)amino]-2-oxoethoxy}phenyl) ethyl]thio}benzoic acid;
2-{[4-(2-{heptyl[2-(2-methoxyphenyl)ethyl]amino}-2-oxoethyl)phenoxy]methyl}benzoic acid;
2-[(4-{2-[[2-(4-chlorophenyl)ethyl](heptyl)amino]-2-oxoethyl}phenoxy)methyl]benzoic acid;
2-[(4-{2-[heptyl(2-phenylethyl)amino]-2-oxoethyl}-phenoxy)methyl]benzoic acid;
2-[(4-{2-[ethyl(2-fluorobenzyl)amino]-2-oxoethoxy}phenoxy)methyl]benzoic acid;
2-[(4-{2-[ethyl(2-fluorobenzyl)amino]-2-oxoethyl}benzyl) oxy]benzoic acid;
2-[(4-{2-[heptyl(2-phenylethyl)amino]-2-oxoethyl}benzyl) oxy]benzoic acid;
2-{2-[4-(2-{isobutyl[4-(trifluoromethyl)benzyl]amino}-2-oxoethoxy)phenyl]ethoxy}-benzoic acid; and
2-[(4-{2-[[2-(4-chlorophenyl)ethyl](heptyl)amino]-2-oxoethyl}benzyl)oxy]benzoic acid and pharmaceutically acceptable salts thereof.

It will also be understood that certain compounds of the present invention may exist in solvated as well as unsolvated forms. It is to be understood that the present invention encompasses all such solvated forms. Certain compounds of the present invention may exist as tautomers. It is to be understood that the present invention encompasses all such tautomers.

Methods of Preparation

The compounds of the invention may be prepared as outlined below. However, the invention is not limited to these methods, the compounds may also be prepared as described for structurally related compounds in the prior art. The reactions can be carried out according to standard procedures or as described in the experimental section. Compounds of formula I may be prepared by reacting a compound of formula II

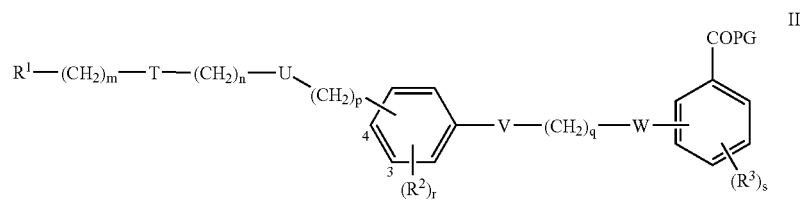

in which $R^1$, T, U, V, W, $R^2$, $R^3$, m, n, p, q, r and s are as previously defined and PG represents a protecting group for a carboxylic hydroxy group as described in the standard text "Protective Groups in Organic Synthesis", $2^{nd}$ Edition (1991) by Greene and Wuts, with a de-protecting agent. The protecting group may also be a resin, such as Wang resin or 2-chlorotrityl chloride resin. Protecting groups may be removed in accordance to techniques which are well known to those skilled in the art. One such protecting group is where PG represents $C_{1-6}$alkoxy group or an arylalkoxy group eg benzyloxy, such that COPG represents an ester. Such esters can be reacted with a hydrolysing agent, for example lithium hydroxide in the presence of a solvent for example a mixture of THF and water or potassium hydroxide in a $C_{1-3}$ alcohol for example methanol, at a temperature in the range of 0-200° C. or by microwave radiation to give compounds of formula I. Compounds of formula II may be prepared according to one of the following routes 1 to 5. It will be appreciated by those skilled in the art that methods analogous to those given in routes 1 to 5 may be used to prepare intermediates for compounds of Formula I in which $R^1$ is a heterocyclic group. Also analogous routes to routes 1 to 5 may be used to prepare compounds of Formula I in which the oxygen atom in the linking chains is replaced by S or NR.

route 1

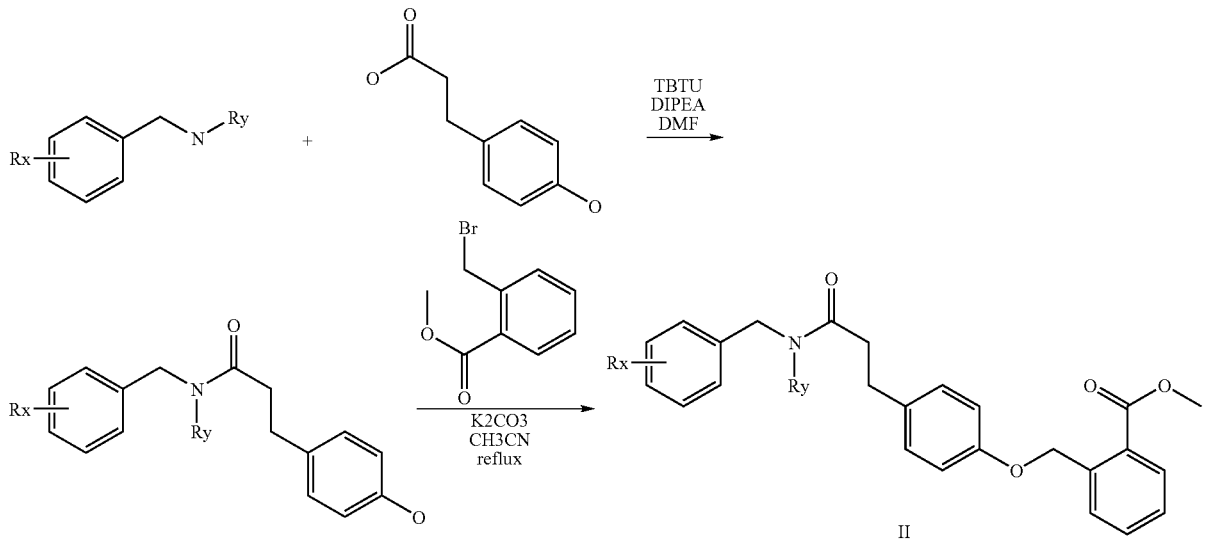

route 2

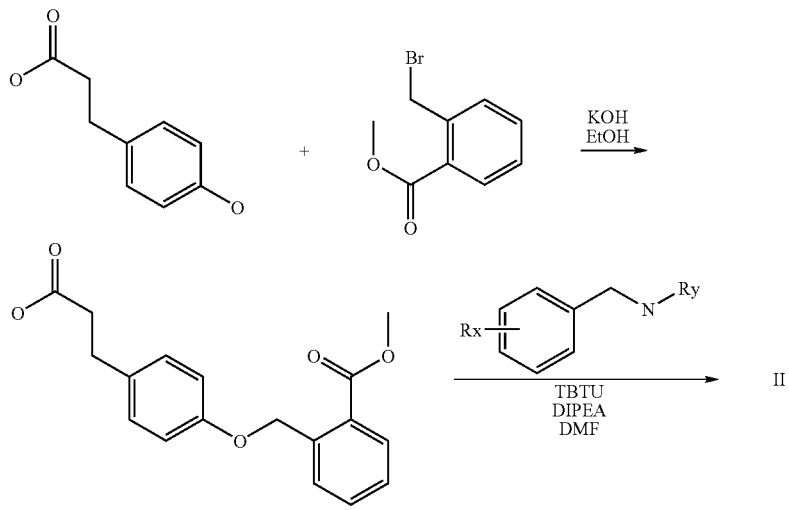

route 3

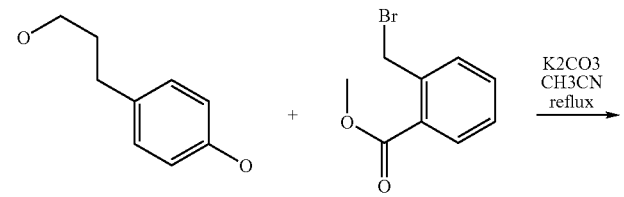

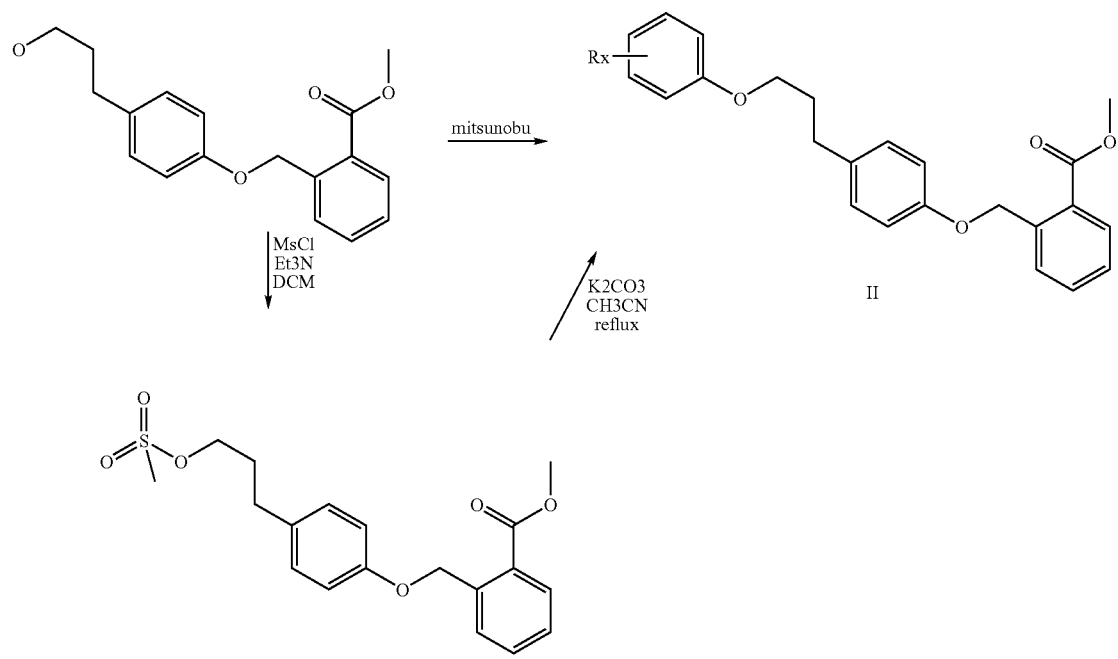
route 4
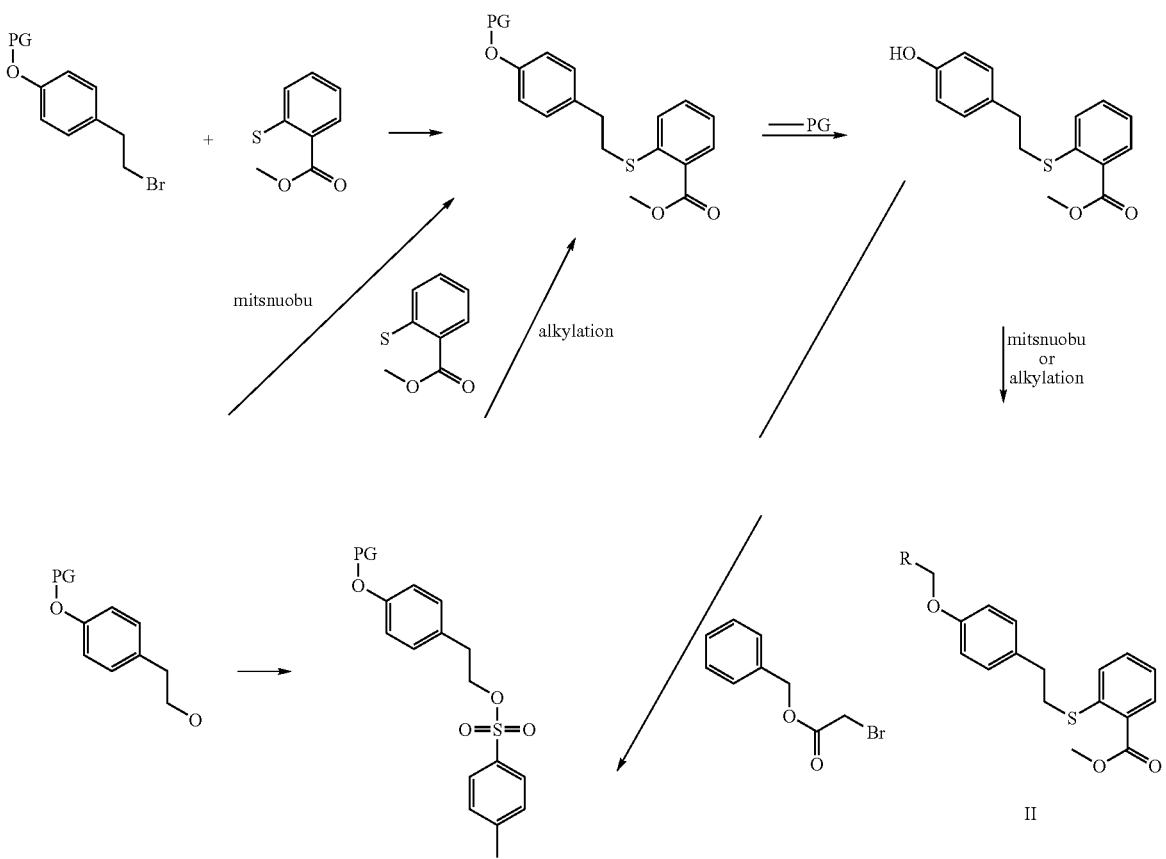

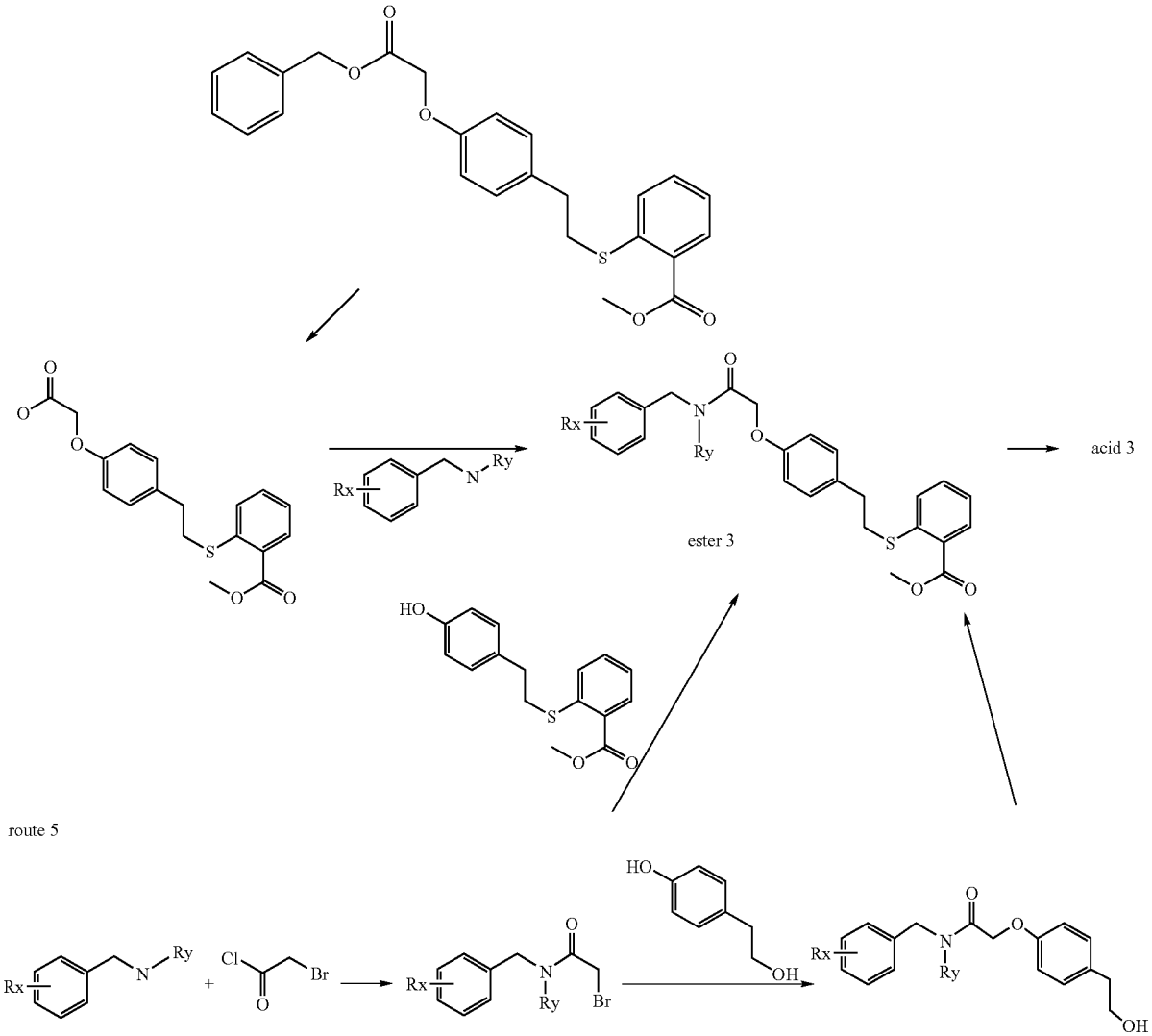
route 5
Starting amines may be prepared as described in Ralph N Salvatore et al Tetrahedron, 57, 7785-7811, 2001 or by the methods given below.
1. Making amide then reduction.
2. reductive amination
3. N-alkylation
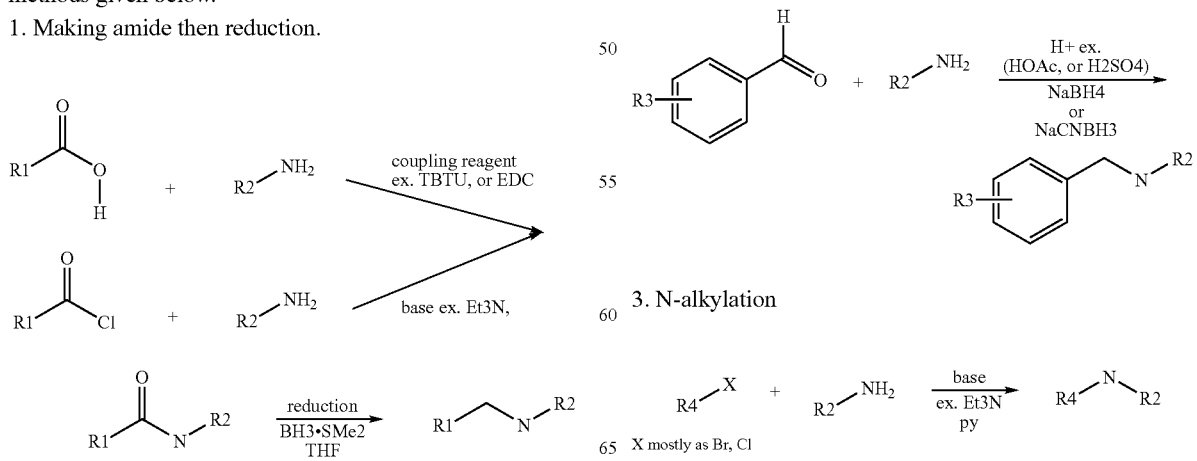

Compounds of formula II are believed to be novel and are claimed herein as useful intermediates in the preparation of compounds of formula I.

The compounds of the invention may be isolated from their reaction mixtures using conventional techniques.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

In any of the preceding methods of preparation, where necessary, hydroxy, amino or other reactive groups may be protected using a protecting group, $R^p$ as described in the standard text "Protective groups in Organic Synthesis", $2^{nd}$ Edition (1991) by Greene and Wuts. The protecting group may also be a resin, such as Wang resin or 2-chlorotrityl chloride resin. The protection and deprotection of functional groups may take place before or after any of the reaction steps described hereinbefore. Protecting groups may be removed in accordance to techniques which are well known to those skilled in the art.

The expression "inert solvent" refers to a solvent which does not react with the starting materials, reagents, intermediates or products in a manner which adversely affects the yield of the desired product.

Pharmaceutical Preparations

The compounds of the invention will normally be administered via the oral, parenteral, intravenous, intramuscular, subcutaneous or in other injectable ways, buccal, rectal, vaginal, transdermal and/or nasal route and/or via inhalation, in the form of pharmaceutical preparations comprising the active ingredient either as a free acid, or a pharmaceutically acceptable salt, in a pharmaceutically acceptable dosage form. Depending upon the disorder and patient to be treated and the route of administration, the compositions may be administered at varying doses.

Suitable daily doses of the compounds of the invention in therapeutical treatment of humans are about 0.0001-100 mg/kg body weight, preferably 0.001-10 mg/kg body weight.

Oral formulations are preferred particularly tablets or capsules which may be formulated by methods known to those skilled in the art to provide doses of the active compound in the range of 0.5 mg to 500 mg for example 1 mg, 3 mg, 5 mg, 10 mg, 25 mg, 50 mg, 100 mg and 250 mg.

According to a further aspect of the invention there is thus provided a pharmaceutical formulation including any of the compounds of the invention, or pharmaceutically acceptable derivatives thereof, in admixture with pharmaceutically acceptable adjuvants, diluents and/or carriers.

Pharmacological Properties

The present compounds of formula (I) are useful for the prophylaxis and/or treatment of clinical conditions associated with inherent or induced reduced sensitivity to insulin (insulin resistance) and associated metabolic disorders (also known as metabolic syndrome). These clinical conditions will include, but will not be limited to, general obesity, abdominal obesity, arterial hypertension, hyperinsulinaemia, hyperglycaemia, type 2 diabetes and the dyslipidaemia characteristically appearing with insulin resistance. This dyslipidaemia, also known as the atherogenic lipoprotein profile, is characterised by moderately elevated non-esterified fatty acids, elevated very low density lipoprotein (VLDL) triglyceride rich particles, high Apo B levels, low high density lipoprotein (HDL) levels associated with low apoAI particle levels and high Apo B levels in the presence of small, dense, low density lipoproteins (LDL) particles, phenotype B.

The compounds of the present invention are expected to be useful in treating patients with combined or mixed hyperlipidemias or various degrees of hypertriglyceridemias and postprandial dyslipidemia with or without other manifestations of the metabolic syndrome.

Treatment with the present compounds is expected to lower the cardiovascular morbidity and mortality associated with atherosclerosis due to their antidyslipidaemic as well as antiinflammatory properties. The cardiovascular disease conditions include macro-angiopathies of various internal organs causing myocardial infarction, congestive heart failure, cerebrovascular disease and peripheral arterial insufficiency of the lower extremities. Because of their insulin sensitizing effect the compounds of formula I are also expected to prevent or delay the development of type 2 diabetes from the metabolic syndrome and diabetes of pregnancy. Therefore the development of long-term complications associated with chronic hyperglycaemia in diabetes mellitus such as the micro-angiopathies causing renal disease, retinal damage and peripheral vascular disease of the lower limbs are expected to be delayed. Furthermore the compounds may be useful in treatment of various conditions outside the cardiovascular system whether or not associated with insulin resistance, like polycystic ovarian syndrome, obesity, cancer and states of inflammatory disease including neurodegenerative disorders such as mild cognitive impairment, Alzheimer's disease, Parkinson's disease and multiple sclerosis.

The compounds of the present invention are expected to be useful in controlling glucose levels in patients suffering from type 2 diabetes.

The present invention provides a method of treating or preventing dyslipidemias, the insulin resistance syndrome and/or metabolic disorders (as defined above) comprising the administration of a compound of formula I to a mammal (particularly a human) in need thereof.

The present invention provides a method of treating or preventing type 2 diabetes comprising the administration of an effective amount of a compound of formula I to a mammal (particularly a human) in need thereof.

In a further aspect the present invention provides the use of a compound of formula I as a medicament.

In a further aspect the present invention provides the use of a compound of formula I in the manufacture of a medicament for the treatment of insulin resistance and/or metabolic disorders.

Combination Therapy

The compounds of the invention may be combined with another therapeutic agent that is useful in the treatment of disorders associated with the development and progress of atherosclerosis such as hypertension, hyperlipidaemias, dyslipidaemias, diabetes and obesity. The compounds of the invention may be combined with another therapeutic agent that decreases the ratio of LDL:HDL or an agent that causes a decrease in circulating levels of LDL-cholesterol. In patients with diabetes mellitus the compounds of the invention may also be combined with therapeutic agents used to treat complications related to micro-angiopathies.

The compounds of the invention may be used alongside other therapies for the treatment of metabolic syndrome or type 2 diabetes and its associated complications, these include biguanide drugs, for example metformin, phenformin and buformin, insulin (synthetic insulin analogues, amylin)

and oral antihyperglycemics (these are divided into prandial glucose regulators and alpha-glucosidase inhibitors). An example of an alpha-glucosidase inhibitor is acarbose or voglibose or miglitol. An example of a prandial glucose regulator is repaglinide or nateglinide.

In another aspect of the invention, the compound of formula I, or a pharmaceutically acceptable salt, solvate, solvate of such a salt or a prodrug thereof, may be administered in association with another PPAR modulating agent. PPAR modulating agents include but are not limited to a PPAR alpha and/or gamma and/or delta agonist, or pharmaceutically acceptable salts, solvates, solvates of such salts or prodrugs thereof. Suitable PPAR alpha and/or gamma agonists, pharmaceutically acceptable salts, solvates, solvates of such salts or prodrugs thereof are well known in the art. These include the compounds described in WO 01/12187, WO 01/12612, WO 99/62870, WO 99/62872, WO 99/62871, WO 98/57941, WO 01/40170, J Med Chem, 1996, 39, 665, Expert Opinion on Therapeutic Patents, 10 (5), 623-634 (in particular the compounds described in the patent applications listed on page 634) and J Med Chem, 2000, 43, 527 which are all incorporated herein by reference. Particularly a PPAR alpha and/or gamma agonist refers to BMS 298585, clofibrate, fenofibrate, bezafibrate, gemfibrozil and ciprofibrate; GW 9578, pioglitazone, rosiglitazone, rivoglitazone, balaglitazone, KRP-297, JTT-501, SB 213068, GW 1929, GW 7845, GW 0207, L-796449, L-165041 and GW 2433. Particularly a PPAR alpha and/or gamma agonist refers to (S)-2-ethoxy-3-[4-(2-{4-methanesulphonyloxy-phenyl}ethoxy)phenyl]propanoic acid and pharmaceutically acceptable salts thereof.

In addition the combination of the invention may be used in conjunction with a sulfonylurea for example: glimepiride, glibenclamide (glyburide), gliclazide, glipizide, gliquidone, chloropropamide, tolbutamide, acetohexamide, glycopyramide, carbutamide, glibonuride, glisoxepid, glybuthiazole, glibuzole, glyhexamide, glymidine, glypinamide, phenbutamide, tolcylamide and tolazamide. Preferably the sulfonylurea is glimepiride or glibenclamide (glyburide). More preferably the sulfonylurea is glimepiride. Therefore the present invention includes administration of a compound of the present invention in conjunction with one, two or more existing therapies described in this paragraph. The doses of the other existing therapies for the treatment of type 2 diabetes and its associated complications will be those known in the art and approved for use by regulatory bodies for example the FDA and may be found in the Orange Book published by the FDA. Alternatively smaller doses may be used as a result of the benefits derived from the combination. The present invention also includes a compound of the present invention in combination with a cholesterol-lowering agent. The cholesterol-lowering agents referred to in this application include but are not limited to inibitors of HMG-CoA reductase (3-hydroxy-3-methylglutaryl coenzyme A reductase). Suitably the HMG-CoA reductase inhibitor is a statin selected from the group consisting of atorvastatin, bervastatin, cerivastatin, dalvastatin, fluvastatin, itavastatin, lovastatin, mevastatin, nicostatin, nivastatin, pravastatin and simvastatin, or a pharmaceutically acceptable salt, especially sodium or calcium, or a solvate thereof, or a solvate of such a salt. A particular statin is atorvastatin, or a pharmaceutically acceptable salt, solvate, solvate of such a salt or a prodrug thereof. A more particular statin is atorvastatin calcium salt. A particularly preferred statin is, however, a compound with the chemical name (E)-7-[4-(4-fluorophenyl)-6-isopropyl-2-[methyl(methylsulfonyl)-amino]-pyrimidin-5-yl](3R,5S)-3,5-dihydroxyhept-6-enoic acid, [also known as (E)-7-[4-(4-fluorophenyl)-6-isopropyl-2-[N-methyl-N-(methylsulfonyl)-amino] pyrimidin-5-yl](3R,5S)-3,5-dihydroxyhept-6-enoic acid] or a pharmaceutically acceptable salt or solvate thereof, or a solvate of such a salt. The compound (E)-7-[4-(4-fluorophenyl)-6-isopropyl-2-[methyl-(methylsulfonyl)-amino]-pyrimidin-5-yl](3R,5S)-3,5-dihydroxyhept-6-enoic acid, and its calcium and sodium salts are disclosed in European Patent Application, Publication No. EP-A-0521471, and in Bioorganic and Medicinal Chemistry, (1997), 5(2), 437-444. This latter statin is now known under its generic name rosuvastatin.

In the present application, the term "cholesterol-lowering agent" also includes chemical modifications of the HMG-CoA reductase inhibitors, such as esters, prodrugs and metabolites, whether active or inactive.

The present invention also includes a compound of the present invention in combination with a bile acid sequestering agent, for example colestipol or cholestyramine or cholestagel.

The present invention also includes a compound of the present invention in combination with an inhibitor of the ileal bile acid transport system (IBAT inhibitor).

Suitable compounds possessing IBAT inhibitory activity have been described, see for instance the compounds described in WO 93/16055, WO 94/18183, WO 94/18184, WO 94/24087, WO 96/05188, WO 96/08484, WO 96/16051, WO 97/33882, WO 98/07749, WO 98/38182, WO 98/40375, WO 98/56757, WO 99/32478, WO 99/35135, WO 99/64409, WO 99/64410, WO 00/01687, WO 00/20392, WO 00/20393, WO 00/20410, WO 00/20437, WO 01/34570, WO 00/35889, WO 00/47568, WO 00/61568, WO 01/68637, WO 01/68096, WO 02/08211, WO 00/38725, WO 00/38726, WO 00/38727, WO 00/38728, WO 00/38729, DE 19825804, JP 10072371, U.S. Pat. No. 5,070,103, EP 251 315, EP 417 725, EP 489 423, EP 549 967, EP 573 848, EP 624 593, EP 624 594, EP 624 595, EP 869 121, EP 864 582, and EP 1 070 703, and the contents of these patent applications, particularly the compounds described in claim 1 and the named examples, are incorporated herein by reference.

Particular classes of IBAT inhibitors suitable for use in the present invention are benzothiepines, and the compounds described in the claims, particularly claim 1, of WO 00/01687, WO 96/08484 and WO 97/33882 are incorporated herein by reference. Other suitable classes of IBAT inhibitors are the 1,2-benzothiazepines, 1,4-benzothiazepines and 1,5-benzothiazepines. A further suitable class of IBAT inhibitors is the 1,2,5-benzothiadiazepines.

One particular suitable compound possessing IBAT inhibitory activity is (3R,5R)-3-butyl-3-ethyl-1,1-dioxido-5-phenyl-2,3,4,5-tetrahydro-1,4-benzothiazepin-8-yl β-D-glucopyranosiduronic acid (EP 864 582). Other suitable IBAT inhibitors include one of:
1,1-dioxo-3,3-dibutyl-5-phenyl-7-methylthio-8-(N-{(R)-1'-phenyl-1'-[N'-(carboxymethyl) carbamoyl] methyl}carbamoylmethoxy)-2,3,4,5-tetrahydro-1,5-benzothiazepine;
1,1-dioxo-3,3-dibutyl-5-phenyl-7-methylthio-8-(N-{(R)-α-[N'-(carboxymethyl)carbamoyl]-4-hydroxybenzyl}carbamoylmethoxy)-2,3,4,5-tetrahydro-1,5-benzothiazepine;
1,1-dioxo-3,3-dibutyl-5-phenyl-7-methylthio-8-(N-{(R)-1'-phenyl-1'-[N'-(2-sulphoethyl)carbamoyl] methyl}carbamoylmethoxy)-2,3,4,5-tetrahydro-1,5-benzothiazepine;
1,1-dioxo-3-butyl-3-ethyl-5-phenyl-7-methylthio-8-(N-{(R)-1'-phenyl-1'-[N'-(2-sulphoethyl)carbamoyl] methyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-sulphoethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-sulphoethyl) carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(5-carboxypentyl) carbamoyl] benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-(N-{α-[N'-(2-sulphoethyl)carbamoyl]-2-fluorobenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(R)-(2-hydroxy-1-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'(R)-(2-hydroxy-1-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-{N-[(R)-α-(N'-{(R)-1-[N''-(R)-(2-hydroxy-1-carboxyethyl)carbamoyl]-2-hydroxyethyl}carbamoyl)benzyl]carbamoylmethoxy}-2,3,4,5-tetrahydro-1,5-benzothiazepine;

1,1-dioxo-3-butyl-3-ethyl-5-phenyl-7-methylthio-8-(N-{α-[N'-(carboxymethyl)carbamoyl] benzyl}carbamoylmethoxy)-2,3,4,5-tetrahydro-1,5-benzothiazepine;

1,1-dioxo-3-butyl-3-ethyl-5-phenyl-7-methylthio-8-(N-{α-[N'-((ethoxy)(methyl)phosphoryl-methyl)carbamoyl] benzyl}carbamoylmethoxy)-2,3,4,5-tetrahydro-1,5-benzothiazepine;

1,1-dioxo-3-butyl-3-ethyl-5-phenyl-7-methylthio-8-{N-[(R)-α-(N'-{2-[(hydroxy)(methyl)phosphoryl]ethyl}carbamoyl)benzyl]carbamoylmethoxy}-2,3,4,5-tetrahydro-1,5-benzothiazepine;

1,1-dioxo-3,3-dibutyl-5-phenyl-7-methylthio-8-(N-{(R)-α-[N'-(2-methylthio-1-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-{N-[(R)-α-(N'-{2-[(methyl)(ethyl) phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-{N-[(R)-α-(N'-{2-[(methyl)(hydroxy) phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-(N-{(R)-α-[(R)-N'-(2-methylsulphinyl-1-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methoxy-8-[N-{(R)-α-[N'-(2-sulphoetlyl)carbamoyl]-4-hydroxybenzyl}carbamoylmethoxy]-2,3,4,5-tetrahydro-1,5-benzothiazepine;

1,1-dioxo-3,3-dibutyl-5-phenyl-7-methylthio-8-(N-{(R)-α-[N-((R)-1-carboxy-2-methylthio-ethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxybutyl) carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxypropyl) carbamoyl] benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl) carbamoyl] benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl)carbamoyl] benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-(2-sulphoethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((R)-1-carboxy-2-methylthioethyl)carbamoyl] benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-{(S)-1-[N-((S)-2-hydroxy-1-carboxyethyl)carbamoyl] propyl}carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)carbamoyl] benzyl}carbamoylmethoxy)-2,3,4,5-tetrahydro-1,2,5-benzothiadiazepine;

1,1-Dioxo-3,3-dibutyl-5-phenyl-7-methylthio-8-(N-{(R)-α-[N-((S)-1-carboxypropyl) carbamoyl]-4-hydroxybenzyl}carbamoylmethoxy)-2,3,4,5-tetrahydro-1,2,5-benzothiadiazepine;

1,1-Dioxo-3,3-dibutyl-5-phenyl-7-methylthio-8-[N-((R/S)-α-{N-[1-(R)-2-(S)-1-hydroxy-1-(3,4-dihydroxyphenyl) prop-2-yl]carbamoyl}-4-hydroxybenzyl)carbamoylmethoxy]-2,3,4,5-tetrahydro-1,2,5-benzothiadiazepine;

1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxyhexyl)carbamoyl]-4- hydroxybenzyl}carbamoylmethoxy)-2,3,4,5-tetrahydro-1,2,5-benzothiadiazepine; and 1,1-Dioxo-3,3-dibutyl-5-phenyl-7-methylthio-8-(N-{(R)-α-[N-(2-(S)-3-(R)-4)-5-(R)-2,3,4,5,6-pentahydroxyhexyl)carbamoyl]benzyl}carbamoylmethoxy)-2,3,4,5-tetrahydro-1,2,5-benzothiadiazepine;

or a pharmaceutically acceptable salt, solvate, solvate of such a salt or a prodrug thereof.

According to an additional further aspect of the present invention there is provided a combination treatment comprising the administration of an effective amount of a compound of the formula I, or a pharmaceutically acceptable salt, solvate, solvate of such a salt or a prodrug thereof, optionally together with a pharmaceutically acceptable diluent or carrier, with the simultaneous, sequential or separate administration one or more of the following agents selected from:

a CETP (cholesteryl ester transfer protein) inhibitor, for example those referenced and described in WO 00/38725 page 7 line 22-page 10, line 17 which are incorporated herein by reference;

a cholesterol absorption antagonist for example azetidinones such as SCH 58235 and those described in U.S. Pat. No. 5,767,115 which are incorporated herein by reference;

a MTP (microsomal transfer protein) inhibitor for example those described in Science, 282, 751-54, 1998 which are incorporated herein by reference;

a nicotinic acid derivative, including slow release and combination products, for example, nicotinic acid (niacin), acipimox and niceritrol;

a phytosterol compound for example stanols;

probucol;

an omega-3 fatty acid for example Omacor™;

an anti-obesity compound for example orlistat (BP 129,748) and sibutramine (GB 2,184,122 and U.S. Pat. No. 4,929,629);

an antihypertensive compound for example an angiotensin converting enzyme (ACE) inhibitor, an angiotensin II receptor antagonist, an andrenergic blocker, an alpha andrenergic blocker, a beta andrenergic blocker for example metoprolol, a mixed alpha/beta andrenergic blocker, an andrenergic stimulant, calcium channel blocker, an AT-1 blocker, a saluretic, a diuretic or a vasodilator;

a CB1 antagonist or inverse agonist for example as described in WO01/70700 and EP 65635;

aspirin;

a Melanin concentrating hormone (MCH) antagonist;

a PDK inhibitor; or modulators of nuclear receptors for example LXR, FXR, RXR, and RORalpha;

or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

Particular ACE inhibitors or pharmaceutically acceptable salts, solvates, solvate of such salts or a prodrugs thereof, including active metabolites, which can be used in combination with a compound of formula I include but are not limited to, the following compounds: alacepril, alatriopril, altiopril calcium, ancovenin, benazepril, benazepril hydrochloride, benazeprilat, benzoylcaptopril, captopril captopril-cysteine, captopril-glutathione, ceranapril, ceranopril, ceronapril, cilazapril, cilazaprilat, delapril, delapril-diacid, enalapril, enalaprilat, enapril, epicaptopril, foroxymithine, fosfenopril, fosenopril, fosenopril sodium, fosinopril, fosinopril sodium, fosinoprilat, fosinoprilic acid, glycopril, hemorphin-4, idrapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spiropril hydrochloride, temocapril, temocapril hydrochloride, teprotide, trandolapril, trandolaprilat, utibapril, zabicipril, zabiciprilat, zofenopril and zofenoprilat. Preferred ACE inhibitors for use in the present invention are ramipril, ramiprilat, lisinopril, enalapril and enalaprilat. More preferred ACE inhibitors for uses in the present invention are ramipril and ramiprilat.

Preferred angiotensin II antagonists, pharmaceutically acceptable salts, solvates, solvate of such salts or a prodrugs thereof for use in combination with a compound of formula I include, but are not limited to, compounds: candesartan, candesartan cilexetil, losartan, valsartan, irbesartan, tasosartan, telmisartan and eprosartan, Particularly preferred angiotensin II antagonists or pharmaceutically acceptable derivatives thereof for use in the present invention are candesartan and candesartan cilexetil.

Therefore in an additional feature of the invention, there is provided a method for the treatment of type 2 diabetes and its associated complications in a warm-blooded animal, such as man, in need of such treatment which comprises administering to said animal an effective amount of a compound of formula I, or a pharmaceutically acceptable salt, solvate, solvate of such a salt or a prodrug thereof in simultaneous, sequential or separate administration with an effective amount of one the other compounds described in this combination section, or a pharmaceutically acceptable salt, solvate, solvate of such a salt or a prodrug thereof.

Therefore in an additional feature of the invention, there is provided a method of treating hyperlipidemic conditions in a warm-blooded animal, such as man, in need of such treatment which comprises administering to said animal an effective amount of a compound of formula I, or a pharmaceutically acceptable salt, solvate, solvate of such a salt or a prodrug thereof in simultaneous, sequential or separate administration with an effective amount of one the other compounds described in this combination section or a pharmaceutically acceptable salt, solvate, solvate of such a salt or a prodrug thereof.

According to a further aspect of the invention there is provided a pharmaceutical composition which comprises a compound of formula I, or a pharmaceutically acceptable salt, solvate, solvate of such a salt or a prodrug thereof, and one of the other compounds described in this combination section or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula I, or a pharmaceutically acceptable salt, solvate, solvate of such a salt or a prodrug thereof, and one of the other compounds described in this combination section or a pharmaceutically acceptable salt, solvate, solvate of such a salt or a prodrug thereof.

According to a further aspect of the present invention there is provided a kit comprising:

a) a compound of formula I, or a pharmaceutically acceptable salt, solvate, solvate of such a salt or a prodrug thereof, in a first unit dosage form;

b) one of the other compounds described in this combination section or a pharmaceutically acceptable salt, solvate, solvate of such a salt or a prodrug thereof; in a second unit dosage form; and c) container means for containing said first and second dosage forms.

According to a further aspect of the present invention there is provided a kit comprising:

a) a compound of formula I, or a pharmaceutically acceptable salt, solvate, solvate of such a salt or a prodrug thereof, together with a pharmaceutically acceptable diluent or carrier, in a first unit dosage form;

b) one of the other compounds described in this combination section or a pharmaceutically acceptable salt, solvate, solvate of such a salt or a prodrug thereof, in a second unit dosage form; and c) container means for containing said first and second dosage forms.

According to another feature of the invention there is provided the use of a compound of the formula I, or a pharmaceutically acceptable salt, solvate, solvate of such a salt or a prodrug thereof, and one of the other compounds described in this combination section, or a pharmaceutically acceptable salt, solvate, solvate of such a salt or a prodrug thereof, in the manufacture of a medicament for use in the treatment of metabolic syndrome or type 2 diabetes and its associated complications in a warm-blooded animal, such as man.

According to another feature of the invention there is provided the use of a compound of the formula I, or a pharmaceutically acceptable salt, solvate, solvate of such a salt or a prodrug thereof, and one of the other compounds described in this combination section, or a pharmaceutically acceptable salt, solvate, solvate of such a salt or a prodrug thereof, in the manufacture of a medicament for use in the treatment of hyperlipidaemic conditions in a warm-blooded animal, such as man.

According to a further aspect of the present invention there is provided a combination treatment comprising the administration of an effective amount of a compound of the formula I, or a pharmaceutically acceptable salt, solvate, solvate of such a salt or a prodrug thereof, optionally together with a pharmaceutically acceptable diluent or carrier, with the simultaneous, sequential or separate administration of an effective amount of one of the other compounds described in this combination section, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

WORKING EXAMPLES $^1$H NMR and $^{13}$C NMR measurements were performed on a Varian Mercury 300 or Varian UNITY plus 400, 500 or 600 spectrometers, operating at $^1$H frequencies of 300, 400, 500 and 600 MHz, respectively, and at $^{13}$C frequencies of 75, 100, 125 and 150 MHz, respectively. Measurements were made on the delta scale ($\delta$).

Unless otherwise stated, chemical shifts are given in ppm with the solvent as internal standard.

Abbreviations
IRS insulin resistance syndrome
TLC thin layer chromatography
HOBtxH$_2$O 1-hydroxybenzotriazole-hydrate
DIBAH diisobutylaluminium hydride
DMSO dimethyl sulfoxide
EtOAc ethyl acetate
DMF N,N-dimethylformamide
THF tetrahydrofuran
HPLC high performance liquid chromatography
MeCN acetonitrile
TFA trifluoroacetic acid
Pd/C palladium on charcoal
HATU O-(7-azabenzotriazolyl-1-yl)-N,N,N',N'-tetramethyluronium hexafluorophosphate
DCM dichloromethane
NH$_4$OAc ammonium acetate
MeOH Methanol
DIPEA N,N-diisopropylethylamine
DMAP 4-dimethylaminopyridine
Trisamine Tris(hydroxymethyl)aminomethane
TBTU O-(benzotriazol-1-yl)-N,N,N',N'-tetramethyluronium tetrafluoroborate
EDC 1-ethyl-3-(3-dimethylaminopropyl)carbodiimide hydrochloride
NH$_4$OAc ammonium acetate
LC-MS liquid chromatography-mass spectroscopy
ISOLUTE® FLASH Si is a silica column suitable for chromatography
Borohydride on polymer support is Borohydride on Amberlite IRA-400 available from Aldrich
t triplet
s singlet
d doublet
q quartet
qvint quintet
m multiplet
br broad
bs broad singlet
dm doublet of multiplet
bt broad triplet
dd doublet of doublet Example 1 a) tert-Butyl 3-{[(1,1'-biphenyl-4-ylcarbonyl)amino]methyl}phenylcarbamate

Biphenyl-4-carboxylic acid (981 mg, 4.949 mmol) and 3-(aminomethyl)-1-N-boc-aniline (1.0 g, 4.499 mmol) were mixed in DMF (10 ml). Under stirring, benzotriazol-1-yl-oxytri-pyrrolidinophosphonium hexafluorophosphate (2.343 g, 4.504 mmol) was added and then N,N-diisopropylethylamine (1.164 g, 9.007 mmol) was added. The mixture was stirred overnight at room temperature. Water and ethyl acetate were added. The organic phase was washed with water, sodium hydrogencarbonate (sat.) and water (×2) and dried with magnesium sulphate. The solvent was removed. Diethyl ether was added into the residue. The solid product was filtered, washed with little diethyl ether and dried, 1.44 g product was obtained. The filtrate was evaporated to dryness. DCM was added to the residue. Filtration gave 0.12 g more solid product. In total 1.56 g desired product was obtained, yield 86%.

$^1$H NMR (400 MHz, CDCl$_3$): $\delta$ 3.61 (s, 9H), 4.66 (d, 2H), 6.43 (s, br, 1H), 6.50 (s, 1H), 7.06-7.09 (m, 1H), 7.27-7.30 (m, 2H), 7.38-7.50 (m, 4H), 7.61-7.64 (m, 2H), 7.67 (d, 2H) and 7.88 (2H).

b) N-(3-Aminobenzyl)-1,1'-biphenyl-4-carboxamide tert-Butyl 3-{[(1,1'-biphenyl-4-ylcarbonyl)amino]methyl}phenylcarbamate (250 mg, 0.6 mmol) was dissolved in DCM (10 ml). Trifluoroacetic acid (0.2 ml) was added. The mixture was stirred overnight. HPLC showed that more than 50% of the starting material was not reacted. More trifluoroacetic acid (0.3 ml) was added. The mixture was stirred overnight again. Water was added into the mixture. The phases were not clear. DCM was evaporated in vacuum Ethyl acetate was added to the residue. The obtained organic phase was washed with water (×3) and dried with magnesium sulphate. The solvent was then evaporated. Solid product (185 mg) was obtained, yield 99%.

$^1$H NMR (500 MHz, CD$_3$OD): δ 4.64 (s, 2H), 7.27 (d, 1H), 7.37-7.40 (m, 2H), 7.45-7.53 (my 4H), 7.66 (d, 2H), 7.74 (d, 2H) and 7.95 (d, 2H).

c) 3-{[(3-{[(1,1'-Biphenyl-4-ylcarbonyl)amino]methyl}phenyl)amino]methyl}benzoic acid N-(3-aminobenzyl)-1,1'-biphenyl-4-carboxamide (20 mg, 0.07 mmol) was dissolved in acetic acid (0.5 ml). 3-Carboxybenzaldehyde (14 mg, 0.09 mmol) was added and then sodium borohydride (11 mg, 0.28 mmol) was added. The mixture was stirred at room temperature for 2 hours and evaporated to dryness. DCM was added into the residue. The mixture was loaded on a column (ISOLUTE® SI, 500 mg/3 ml). It was eluted with DCM, MeOH/DCM (0.5:99.5) and then MeOH/DCM (1:99). The product fractions were combined and the solvent was removed, Re-chromatography of the residue on a column (ISOLUTE® SI, 1 g/6 ml) using DCM, MeOH/DCM (0.5:99.5) and then MeOH/DCM (1:99) as eluant gave 9 mg the desired product, yield 31%.

$^1$H NMR (500 MHz, CD$_3$OD): δ 4.37 (s, 2H), 4.46 (d, 2H), 6.53 (d, 1H), 6.59-6.61 (m, 2H), 7.04 (t, 1H), 7.30-7.38 (m, 2H), 7.46 (t, 2H), 7.55 (d, 1H), 7.65-7.70 (m, 4H), 7.83 (t, 3H), 8.02 (s, 1H) and 8.80 (br, 1H).

Example 2 a) Methyl 2-{[4(2-oxo-2-{[4-(trifluoromethyl)benzyl]amino}ethyl)phenoxy]methyl}-benzoate (4-{[2-(Methoxycarbonyl)benzyl]oxy}phenyl)acetic acid (50 mg, 0.167 mmol) was dissolved in DCM (2 ml), 4-(Trifluoromethyl)benzylamine (35 mg, 0.2 mmol) was added, then EDC (38 mg, 0.2 mmol) was added and then DMAP (24.4 mg, 0.2 mmol) was added. The mixture was stirred at room temperature overnight. 1% hydrochloric acid (1 ml) and water (1 ml) was added into the mixture. The two phases were separated using a Whatman Filter Tube. The obtained organic solution was evaporated in vacuum and the solid product (72 mg) was left, yield 95%.

$^1$H NMR (500 MHz, CDCl$_3$): δ 3.63 (s, 2H), 3.93 (s, 3H), 4.50 (d, 2H), 5.53 (s, 2H), 5.79 (hr, 1H), 7.02 (d, 2H), 7.22 (d, 2H), 7.32 (d, 2H), 7.42 (t, 1H), 7.57-7.61 (r, 3H), 7.77 (d, 1H) and 8.07 (d, 1H).

b) 2-{[4-(2-Oxo-2-{[4-(trifluoromethyl)benzyl]amino}ethyl)phenoxy]methyl}benzoic acid Methyl 2-{[4-(2-oxo-2-{[4-(trifluoromethyl)benzyl]amino}ethyl)phenoxy]methyl}-benzoate (71 mg, 0.155 mmol) in THF (1.5 ml) was cooled in an ice-bath. Lithium hydroxide (7.5 mg, 0.310 mmol) in water (1.5 ml) was dropped in. The cooling-bath was then removed and the mixture was stirred overnight. HPLC showed that the reaction was not complete. More lithium hydroxide (0.2M, 0.5 ml) was added. The reaction mixture was stirred for 4 days more. It was then evaporated in vacuum to remove THF. The residue was acidified with 1% hydrochloric acid, pH=3-4, and then extracted with ethyl acetate. The organic phase was dried with magnesium sulphate and evaporated. Chromatography of the residue on a column (ISOLUTE® SI, 2 g/6 ml) using DCM, MeOH/DCM (0.5:99.5, then 1:99, and then 2:98) as eluant gave 39 mg white solid product, yield 57%.

$^1$H NMR (500 MHz, CD$_3$OD): δ 3.50 (s, 2H), 4.42 (d, 2H), 5.47 (s, 2H), 6.94 (d, 2H), 7.22 (d, 2H), 7.37-7.40 (m, 3H), 7.53-7.58 (m, 3H), 7.69 (d, 1H) and 8.01 (d, 1H).

Example 3 a) (3-{[2-(Methoxycarbonyl)benzyl]oxy}phenyl)acetic acid

3-Hydroxyphenylacetic acid (760 mg, (5 mmol) was dissolved in ethanol (99.5%, 20 ml). Potassium hydroxide (560 mg, 10 mmol) was added. The mixture was stirred for 30 minutes. 2-Bromomethylbenzoic acid methyl ester (1.144 g, 5 mmol) was then dropped in. The resulting mixture was heated to reflux for 2 hours and then evaporated in vacuum to dry. Water and ethyl acetate were added into the residue and the phases were separated. The water phase was acidified with 10% hydrochloric acid, pH~5, and then extracted with ethyl acetate. The organic phase was dried (magnesium sulphate) and evaporated in vacuum to dry. Chromatography of the residue on a column (ISOLUTE® SI, 5 g/25 ml) using DCM, MeOH/DCM (1:99) as eluant gave 213 mg, the desired product, yield 14%.

$^1$H NMR (500 MHz, CDCl$_3$): δ 3.65 (s, 2H), 3.91 (s, 3H), 5.51 (s, 2H), 6.90-6.96 (m, 3H), 7.27 (t, 1H), 7.39 (t, 1H), 7.57 (t, 1H), 7.77 (d, 1H) and 8.04 (d, 1H).

b) Methyl 2-[(3-{2-[benzyl(hexyl)amino]-2-oxoethyl}phenoxy)methyl]benzoate (3-{[2-(Methoxycarbonyl)benzyl]oxy}phenyl)acetic acid (60 mg, 0.2 mmol) was dissolved in DCM (2 ml), N-hexylbenzylamine (46 mg, 0.24 mmol) was added, then EDC (46 mg, 0.24 mmol) was added and then DMAP (29.3 mg, 0.24 mmol) was added. The mixture was stirred at room temperature overnight. 1% hydrochloric acid (1 ml) and water (1 ml) were added into the mixture. The two phases were separated by using a Whatman Filter Tube. The obtained organic portion was evaporated in vacuum and 59 mg crude oil product was left. It was then used directly in next step.

c) 2-[(3-{2-[Benzyl(hexyl)amino]-2-oxoethyl}phenoxy)methyl]benzoic acid

Methyl 2-[(3-{2-[benzyl(hexyl)amino]-2-oxoethyl}phenoxy)methyl]benzoate (59 mg, 0.125 mmol) in THF (1 ml) was cooled in an ice-bath. Lithium hydroxide (6 mg, 0.249 mmol) in water (1 ml) was dropped in. The cooling-bath was then removed and the mixture was stirred for 13 days and then evaporated in vacuum to remove THF. The residue was acidified with 1% hydrochloric acid, pH~4, and extracted with ethyl acetate. The organic phase was dried (magnesium sulphate) and evaporated. Chromatography of the residue on a column (ISOLUTE® SI, 1 g/6 ml) using DCM and MeOH/DCM (0.5:99.5, then 1:99) as eluant gave 7 mg the desired product, yield 8% (two steps).

$^1$H NMR (rotamers, 500 MHz, CDCl$_3$): δ 0.85-0.90 (m, 3H), 1.20-1.30 (m, 6H), 1.45-1.57 (m, 2H), 3.20, 3.40 (t, t, 2H), 3.70, 3.80 (s, s, 2H), 4.51, 4.65 (s, s, 2H), 5.51, 5.52 (s, s, 2H), 6.83-7.00 (m, 3H), 7.14-7.43 (m, 7H), 7.59 (t, 1H), 7.78 (d, 1H) and 8.13 (d, 1H).

Example 4 a) Methyl 2-{[3-(2-oxo-2-{[4-(trifluoromethyl)benzyl]amino}ethyl)phenoxy]methyl}-benzoate (3-{[2-(Methoxycarbonyl)benzyl]oxy}phenyl)acetic acid (60 mg, 0.2 mmol) was dissolved in DCM (2 ml). 4-(Trifluoromethyl)benzylamine (42 mg, 0.24 mmol) was added, then EDC (46 mg, (0.24 mmol) was added and then DMAP (29.3 mg, 0.24 mmol) was added. The mixture was stirred at room temperature overnight. 1% Hydrochloric acid (1 ml) and water (1 ml) were added to the mixture. The two phases were separated by using a Whatman Filter Tube. The obtained organic portion was evaporated in vacuum and 82 mg solid product was left. It was then used directly in next step.

b) 2-{[3-(2-Oxo-2-{[4-(trifluoromethyl)benzyl]amino}ethyl)phenoxy]methyl}benzoic acid Methyl 2-{[3-(2-oxo-2-{[4-(trifluoromethyl)benzyl]amino}ethyl)phenoxy]methyl}-benzoate (82 mg, 0.18 mmol) in THF (2 ml) was cooled in an ice-bath. Lithium hydroxide (8.6 mg, 0.36 mmol) in water (1 ml) was dropped in. The cooling-bath was then removed and the mixture was stirred for 7 days and then evaporated in vacuum to remove THF. The residue was acidified with 1% hydrochloric acid, pH~3, and extracted with ethyl acetate. The organic phase was dried (magnesium sulphate) and evaporated. Chromatography of the residue on a column (ISOLUTE® SI, 2 g/6 ml) using DCM and MeOH/DCM (1:99, then 2:98) as eluant gave 20 mg the desired product, yield 22.5% (two steps).

$^1$H NMR (500 MHz, CD$_3$OD): δ 3.55 (s, 2H), 4.43 (s, 2H), 5.47 (s, 2H), 6.90 (t, 2H), 6.98 (s, 1H), 7.23 (t, 1H), 7.38-7.42 (m, 3H), 7.53-7.59 (m, 3H), 7.70 (d, 1H) and 8.03 (d, 1H).

Example 5 a) N-[2-(3,4-dimethoxyphenyl)ethyl]-3-(4-hydroxyphenyl)-N-methylpropanamide 3-(4-Hydroxyphenyl)propionic acid (166.2 mg, 1 mmol) was dissolved in DMF (4 ml). 2-(3,4-Dimethoxyphenyl)-N-methylethylamine (211 mg, 1.05 mmol) was added. The mixture was cooled in an ice-bath. TBTU (337 mg, 1.05 mmol) was added, followed by DIPEA (0.37 ml, 2.1 mmol). The mixture was stirred overnight and the temperature was allowed up to room temperature. Ethyl acetate and sodium hydrogencarbonate aqueous solution (sat.) were added and then the two phases were separated. The water phase was extracted with ethyl acetate. The organic phases were combined and dried (magnesium sulphate) and evaporated. Chromatography of the residue on a column (ISOLUTE® SI, 5 g/15 ml) using DCM and then MeOH/DCM (1:99) as eluant gave 333 mg the desired product, yield 97%.

$^1$H NMR (rotamers, 500 MHz, CDCl$_3$): δ 2.35, 2.59 (t, t, 2H), 2.71-2.80, 2.90 (m, t, 4H), 2.84, 2.97 (s, s, 3H), 3.45, 3.58 (t, t, 2H), 3.84-3.86 (m, 6H), 6.61-6.83 (m, 4H), 6.95 (d, 1H), 7.05 (d, 1H) and 7.50, 7.56 (s, s, 1H).

b) Methyl 2-[(4-{3-[[2-(3,4-dimethoxyphenyl)ethyl](methyl)amino]-3-oxopropyl}phenoxy)methyl]benzoate N-[2-(3,4-dimethoxyphenyl)ethyl]-3-(4-hydroxyphenyl)-N-methylpropanamide (198 mg, 0.577 mmol), 2-bromomethyl-benzoic acid methyl ester (139 mg, 0.605 mmol) and potassium carbonate, anhydrous (120 mg, 0.864 mmol) were mixed in acetonitrile (15 ml). The mixture was heated to reflux overnight and then evaporated to dry. Water and ethyl acetate were added and the two phases were separated. The organic phase was dried (magnesium sulphate) and evaporated. Chromatography of the residue on a column (ISOLUTE® SI, 2 g/6 ml) using heptane/DCM (50:50), then DCM and then MeOH/DCM (0.5:99.5) as eluant gave 172 mg the desired product, yield 61%.

$^1$H NMR (rotamers, 500 MHz, CDCl$_3$); 2.34, 2.58 (t, t, 2H), 2.70-2.97 (m, 7H), 3.44, 3.53 (t, t, 2H ), 3.84-3.92 (m, 9H), 5.49 (s, br, 2H), 6.61-6.82 (m, 3H), 6.92 (t, 2H), 7.05 (d, 1H), 7.15 (d, 1H), 7.38 (t, 1H), 7.55 (t, 1H), 7.74-7.77 (m, 1H) and 8.03 (d, 1H).

c) 2-[(4-{3-[[2-(3,4-Dimethoxyphenyl)ethyl](methyl)amino]-3-oxopropyl}phenoxy)-methyl]benzoic acid Lithium hydroxide (12 mg, 0.488 mmol) in water (1 ml) was added to methyl 2-[(4-{3-[[2-(3,4-dimethoxyphenyl)ethyl](methyl)amino]-3-oxopropyl}phenoxy)methyl]benzoate (120 mg, 0.244 mmol) dissolved in THF (2 ml). The mixture was irradiated in a microwave oven (Smith Synthesizer) at 150° C. for 7 minutes and then evaporated to remove THF. The residue was acidified with 1% hydrochloric acid, pH~4, and extracted with ethyl acetate (×2). The organic extracts were combined and washed with brine and dried with magnesium sulphate and then evaporated. Chromatography of the residue on a column (ISOLUTE® SI, 2 g/6 ml) using DCM, then MeOH/DCM (1:99) as eluant gave 102 mg the desired product, yield 87.5%.

$^1$H NMR (rotamers, 500 MHz, CDCl$_3$): δ 2.40, 2.64 (t, t, 2H), 2.73-3.01 (m, 7H), 3.47, 3.63 (t, t, 2H), 3.85-3.88 (m, 6H), 5.56, 5.57 (s, s, 2H), 6.63-6.83 (m, 3H), 6.93-6.97 (m, 2H), 7.07 (d, 1H), 7.17 (d, 1H), 7.41 (t, 1H), 7.57-7.61 (m, 1H), 7.81 (t, 1H) and 8.18 (d, 1H).

Example 6 a) Methyl 2-[(4-{2-[(tert-butoxycarbonyl)amino]ethyl}phenoxy)methyl]benzoate tert-Butyl 2-(4-hydroxyphenyl)ethylcarbamate (3.534 g, 14.9 mmol), 2-bromomethyl-benzoic acid methyl ester (3.582 g, 15.6 mmol) and potassium carbonate, anhydrous (3.087 g, 22.3 mmol) were mixed in acetonitrile (50 ml). The mixture was heated to reflux overnight and then evaporated to dry. Water and ethyl acetate were added and the two phases were separated. The organic phase was dried (magnesium sulphate) and evaporated. Chromatography of the residue on a column (ISOLUTE® SI, 20 g/70 ml) using DCM and then MeOH/DCM (1:99) as eluant gave 5.427 g the desired product, yield 94.5%.

$^1$H NMR (500 MHz, CDCl$_3$): δ 1.44 (s, 9H), 2.72 (t, 2H), 3.30-3.35 (m, 2H), 3.86 (s, 3H), 4.87 (s, br, 1H), 5.46 (s, 2H), 6.92 (d, 2H), 7.09 (d, 2H), 7.33 (t, 1H), 7.51 (t, 1H), 7.74 (d, 1H) and 8.00 (d, 1H).

b) Methyl 2-{[4-(2-aminoethyl phenoxy]methyl}benzoate hydrochloride

Methyl 2-[(4-{2-[(tert-butoxycarbonyl) amino]ethyl}phenoxy)methyl]benzoate (5.1 g, 13.2 mmol) was dissolved in ethyl acetate (50 ml) and it was cooled in an ice-bath. Hydrochloric acid (4M in dioxane, 30 ml, 120 mmol) was added. The cooling bath was removed after 30 minutes. The mixture was stirred for 3 hours more and white precipitates fell out during the time. The reaction mixture was evaporated to dry. Ethyl acetate (20 ml) was added into the residue. It was then filtered. White solid product (3.785 g) was obtained, yield 89%.

$^1$H NMR (500 MHz, CDCl$_3$): δ 3.06 (t, 2H), 3.23 (t, 2H), 3.90 (s, 3H), 5.45 (s, 2H), 6.93 (d, 2H), 7.18 (d, 2H), 7.37 (t, 1H), 7.55 (t, 1H), 7.73 (d, 1H), 8.02 (d, 1H) and 8.35 (s, br, 2H).

c) Methyl 2-[(4-{2-[({4-methyl-2-[4-(trifluoromethyl)phenyl]-1,3-thiazol-5-yl}carbonyl)amino]ethyl}phenoxy)methyl]benzoate 4-Methyl-2-[4-(trifluoromethyl)phenyl]-1,3-thiazole-5-carboxylic acid (50 mg, 0.174 mmol) and methyl 2-{[4-(2-aminoethyl)phenoxy]methyl}benzoate hydrochloride (59 mg, 0.183 mmol) were mixed in DMF (4 ml) and the mixture was then cooled in an ice-bath. TBTU (59 mg, 0.183 mmol) was added and followed by DIPEA (47.2 mg, 0.366 mmol). The mixture was stirred at room temperature overnight. Ethyl acetate and sodium hydrogencarbonate aqueous solution (sat.) were added. The two phases were separated. The organic phase was washed with water and dried (magnesium sulphate) and evaporated. Chromatography of the residue on a column (ISOLUTE® SI, 2 g/6 ml) using DCM and then MeOH/DCM (0.5:99.5) as eluant gave 59 mg the desired product, white solid, yield 61%.

$^1$H NMR (400 MHz, CDCl$_3$): δ 2.62 (s, 3H), 2.87 (t, 2H), 3.67 (dt, 2H), 3.89 (s, 3H), 5.49 (s, 2H), 5.86 (t, 1H), 6.97 (d, 2H), 7.15 (d, 2H), 7.36 (t, 1H), 7.54 (t, 1H), 7.67 (d, 2H), 7.74 (d, 2H) and 7.99-8.03 (m, 3H).

d) 2-[(4-{2-[({4-Methyl-2-[4-(trifluoromethyl)phenyl]-1,3-thiazol-5-yl}carbonyl)amino]ethyl}phenoxy)methyl]benzoic acid Lithium hydroxide (4 mg, 0.166 mmol) in water (1 ml) was added into methyl 2-[(4-{2-[({4-methyl-2-[4-(trifluoromethyl)phenyl]-1,3-thiazol-5-yl}carbonyl)amino]ethyl}-phenoxy)methyl]benzoate (46 mg, 0.083 mmol) dissolved in THF (2 ml). The mixture was then irradiated in a microwave oven (Smith Synthesizer) at 150° C. for 7 minutes and then evaporated to remove THF. The residue was acidified with 1% hydrochloric acid, pH~4, and extracted with ethyl acetate (×2). The organic extracts were combined and dried with magnesium sulphate and then evaporated. Chromatography of the residue on a column (ISOLUTE® SI, 2 g/6 ml) using DCM, then MeOH/DCM (1:99) as eluant gave 38 mg the desired product, yield 85%.

$^1$H NMR (400 MHz, THF-d8): δ 2.65 (s, 3H), 2.85 (t, 2H), 3.54 (dt, 2H), 5.52 (s, 2H), 6.94 (d, 2H), 7.17 (d, 2H), 7.36 (t, 1H), 7.41 (t, 1H), 7.53 (t, 1H), 7.75-7.79 (m, 3H), 8.06 (d, 1H) and 8.14 (d, 2H).

Example 7 a) Methyl 2-({4-[2-({[(2,4-difluorophenyl)amino]carbonyl}amino)ethyl]phenoxy}-methyl))benzoate 2,4-Difluorophenyl isocyanate (26.5 mg, 0.171 mmol) and methyl 2-{[4-(2-aminoethyl)phenoxy]methyl}benzoate hydrochloride (55 mg, 0.171 mmol) were mixed in DCM (4 ml). PS-DIEA (3.66 mmol/g, 140 mg, 0.512 mmol) was added. The mixture was shaken at room temperature overnight. White precipitates were falling out. The mixture was evaporated to dry. The residue (with addition of DCM, a suspension) was loaded on a column (ISOLUTE® SI, 2 g/6 ml) and eluted with DCM and then MeOH/DCM (1:99). White solid product 51 mg was obtained, yield 68%.

$^1$H NMR (400 MHz, DMSO-d$_6$): δ 2.65 (t, 2H), 3.26-3.31 (m, 2H), 3.79 (s, 3H), 5.36 (s, 2H), 6.49 (t, 1H), 6.88-6.97 (m, 3H), 7.12-7.22 (m, 3H), 7.44 (t, 1H), 7.58-7.65 (m, 2H), 7.88 (d, 1H), 8.01-8.07 (m, 1H) and 8.23 (s, br, 1H).

b) 2-({4-[2-({[(2,4-Difluorophenyl)amino]carbonyl}amino)ethyl]phenoxy}methyl)benzoic acid Lithium hydroxide (3.7 mg, 0.154 mmol) in water (1 ml) was added into methyl 2-({4-[2-({[(2,4-difluorophenyl)amino]carbonyl}amino)ethyl]phenoxy}methyl)benzoate (34 mg, 0.077 mmol) dissolved in THF (2 ml). The mixture was then irradiated in a microwave oven (Smith Synthesizer) at 150° C. for 7 minutes and then evaporated to remove THF. The residue was acidified with 1% hydrochloric acid, pH~4, and extracted with ethyl acetate (×2). The organic extracts were combined and dried with magnesium sulphate and then evaporated. Chromatography of the residue on a column (ISOLUTE® SI, 1 g/6 ml) using MeOH/DCM (1:99, 2:98, 4:96 and then 10:90) as eluant gave 18 mg the desired product, yield 55%.

$^1$H NMR (400 MHz, THF-d8): δ 2.76 (t, 2H), 3.39-3.44 (m, 2H), 5.51 (s, 2H), 6.40 (t, 1H), 6.79-6.94 (m, 4H), 7.16 (d, 2H), 7.35 (t, 1H), 7.53 (t, 1H), 7.76 (d, 1H), 7.93 (s, br, 1H), 8.06 (d, 1H) and 8.29-8.35 (m, 1H).

Example 8 a) Methyl 2-[(4-{2-[(2-methyl-5-phenyl-3-furoyl)amino]ethyl}phenoxy)methyl]benzoate 2-Methyl-5-phenylfuran-3-carbonyl chloride (36.4 mg, 0.165 mmol) and methyl 2-{[4-(2-aminoethyl)phenoxy]methyl}benzoate hydrochloride (53 mg, 0.165 mmol) were mixed in DCM (4 ml). PS-DIBA (3.66 mmol/g, 135 mg, 0.494 mmol) was added. The mixture was shaken at room temperature overnight. LC-MS showed there was only a trace amount of desired product and a big peak of 2-methyl-5-phenyl-3-furoic acid. TBTU (55 mg, 0.17 mmol) was added. The mixture was shaken for 2 hours and filtered. The filtrate was evaporated to dryness. Chromatography of the residue on a column (ISOLUTE® SI, 2 g/6 ml) using DCM and then MeOH/DCM (0.5:99.5) as eluant gave 34 mg the desired product, yield 44%.

$^1$H NMR (500 MHz, CDCl$_3$): δ 2.61 (s, 3H), 2.85 (t, 2H), 3.60-3.66 (m, 2H), 3.89 (s, 3H), 5.49 (s, 2H), 5.82 (t, 1H), 6.55 (s, 1H), 6.96 (d, 2H), 7.15 (d, 2H), 7.25 (t, 1H), 7.36 (t, 3H), 7.52-7.63 (m, 3H), 7.75 (d, 1H) and 8.02 (d, 1H).

b) 2-[(4-{2-[(2-Methyl-5-phenyl-3-furoyl)amino]ethyl}phenoxy)methyl]benzoic acid Lithium hydroxide (3.3 mg, 0.136 mmol) in water (1 ml) was added into methyl 2-[(4-{2-[(2-methyl-5-phenyl-3-furoyl)amino]ethyl}phenoxy)methyl]benzoate (32 mg, 0.068 mmol) dissolved in THF(2 ml). The mixture was then irradiated in a microwave oven (Smith Synthesizer) at 150° C. for 7 minutes and then evaporated to remove THF. The residue was acidified with 1% hydrochloric acid, pH~4, and extracted with ethyl acetate (×2). The organic extracts were combined and washed with brine and dried with magnesium sulphate and then evaporated. Chromatography of the residue on a column (ISOLUTE® SI, 2 g/6 ml) using DCM, then MeOH/DCM (1:99 and 2:98) as eluant gave 22 mg the desired product, yield 71%.

$^1$H NMR (400 MHz, CDCl$_3$): δ 2.60 (s, 3H), 2.84 (t, 2H), 3.60-3.65 (m, 2H), 5.51 (s, 2H), 5.90 (t, 1H), 6.56 (s, 1H), 6.94 (d, 2H), 7.13 (d, 2H), 7.23 (t, 1H), 7.32-7.40 (m, 3H), 7.55-7.60 (m, 3H), 7.77 (d, 1H) and 8.13 (d, 1H).

Example 9 a) Methyl 2-[(4-{2-[(benzylsulfonyl)amino]ethyl}phenoxy)methyl]benzoate

Alpha-toluenesulfonyl chloride (38 mg, 0.199 mmol) and methyl 2-{[4-(2-aminoethyl)phenoxy]methyl}benzoate hydrochloride (64 mg, 0.199 mmol) were mixed in DCM (3 ml). PS-DIEA (3.66 mmol/g, 272 mg, 0.997 mmol) was added. The mixture was shaken at room temperature over a weekend. It was then loaded on a column (ISOLUTE® SI, 1 g/6 ml) and eluted with DCM. The product fractions were combined and evaporated. Oil product (17 mg) was obtained, yield 19%.

$^1$H NMR (500 MHz, CDCl$_3$): δ 2.74 (t, 2H), 3.19-3.23 (m, 2H), 3.92 (s, 3H), 4.12 (t, 1H), 4.21 (s, 2H), 5.50 (s, 2H), 6.94 (d, 2H), 7.07 (d, 2H), 7.32-7.42 (m, 6H), 7.57 (t, 1H), 7.75 (d, 1H) and 8.05 (d, 1H).

b) 2-[(4-{2-[(Benzylsulfonyl)amino]ethyl}phenoxy)methyl]benzoic acid

Lithium hydroxide (2 mg, 0.077 mmol) in water (0.5 ml) was added into methyl 2-[(4-{2-[(benzylsulfonyl)amino]ethyl}phenoxy)methyl]benzoate (17 mg, 0.038 mmol) dissolved in THF (1 ml). The mixture was then in irradiated in a microwave oven (Smith Synthesizer) at 150° C. for 7 minutes and then evaporated to remove THF. The residue was acidified with 1% hydrochloric acid, pH~4, and extracted with ethyl acetate (×2). The organic extracts were combined and dried with MgSO4 and then evaporated. Chromatography of the residue on a column (ISOLUTE® SI, 500 mg/3 ml) using DCM, then MeOH/DCM (0.5:99.5) as eluant gave 10 mg the desired product, yield 61%.

$^1$H NMR (400 MHz, CDCl$_3$): δ 2.70 (t, 2H), 3.16-3.21 (m, 2H), 4.18 (s, 2H), 4.29 (t, 1H), 5.48 (s, 2H), 6.91 (d, 2H), 7.05 (d, 2H), 7.29-7.35 (m, 5H), 7.41 (t, 1H), 7.59 (t, 1H), 7.76 (d, 1H) and 8.14 (d, 1H).

Example 10 a) N-Benzyl-2-(3-fluoro-4-hydroxyphenyl)-N-hexylacetamide

3-Fluoro-4-hydroxyphenylacetic acid (170 mg, 0.999 mmol) dissolved in DMF (3 ml) was cooled in an ice-bath N-Hexylbenzylamine (201 mg, 1.049 mmol) was added and then TBTU (337 mg, 1.049 mmol) followed by DIPEA (407 mg, 3.147 mmol). The mixture was stirred at room temperature overnight and evaporated. Sodium hydrogencarbonate aqueous solution (sat.) was added into the residue. The mixture was then extracted with ethyl acetate (×2). The extracts were combined and washed with water and brine and dried (magnesium sulphate) and evaporated. Chromatography of the residue on a column (ISOLUTE® SI, 5 g/15 ml) using DCM and then MeOH/DCM (1:99) as eluant gave 265 mg the desired product, yield 77%.

$^1$H NMR (rotamers, 400 MHz, CDCl$_3$): δ 0.83-0.89 (m, 3H), 1.22-1.29 (m, 6H), 1.48-1.58 (m, 2H), 3.21, 3.40 (t, t, 2H), 3.58, 3.68 (s, s, 2H), 4.54, 4.63 (s, s, 2H), 6.72-6.97 (m, 3H), 7.15 (d, 1H), 7.21-7.32 (m, 3H) and 7.35-7.39 (m, 1H).

b) Methyl 2-[(4-{2-[benzyl(hexyl)amino]-2-oxoethyl}-2-fluorophenoxy)methyl]benzoate N-benzyl-2-(3-fluoro-4-hydroxyphenyl)-N-hexylacetamide (142 mg, 0.414 mmol), 2-bromomethylbenzoic acid methyl ester (99.4 mg, 0.434 mmol) and potassium carbonate anhydrous (86 mg, 0.620 mmol) were mixed in acetonitrile (5 ml). The mixture was heated to reflux overnight and then evaporated to dry. Ethyl acetate and water were added and the two phases were separated. The organic phase was washed with brine and dried (magnesium sulphate) and evaporated. Chromatography of the residue on a column (ISOLUTE® SI, 2 g/6 ml) using DCM, MeOH/DCM (0.5:99.5) as eluant gave 144 mg the desired product, yield 71%.

$^1$H NMR (rotamers, 400 MHz, CDCl$_3$): δ 0.83-0.89 (m, 3H), 1.20-1.29 (m, 6H), 1.45-1.58 (m, 2H), 3.18, 3.37 (t, t, 2H), 3.58, 3.69 (s, s, 2H), 3.90 (s, 3H), 4.50, 4.60 (s, s, 2H), 5.53, 5.55 (s, s, 2H), 6.82-7.39 (m, 9H), 7.56 (t, 1H), 7.78-7.82 (in, 1H) and 8.02 (d, 1H).

c) 2-[(4-{2-[Benzyl(hexyl)amino]-2-oxoethyl}-2-fluorophenoxy methyl]benzoic acid Methyl 2-[(4-{2-[benzyl(hexyl)amino]-2-oxoethyl}-2-fluorophenoxy)methyl]benzoate (109 mg, 0.222 mmol) was dissolved in THF (2 ml). Lithium hydroxide (10.6 mg, 0.444 mmol) solved in water (1 ml) was added. The mixture was put in a microwave oven (Smith Synthesizer) at 150° C. for 7 minutes. It was then acidified with 1% hydrochloric acid, pH~3, and extracted with ethyl acetate. The organic extract was washed with brine and dried (magnesium sulphate) and evaporated. Chromatography of the residue on a column (ISOLUTE® SI, 2 g/6 ml) using DCM and then MeOH/DCM (0.5: 99.5, then 1:99) as eluant gave 89 mg the desired product, yield 84%.

$^1$H NMR (rotamers, 300 MHz, CDCl$_3$): δ 0.84-0.92 (m, 3H), 1.26 (s, br, 6H), 1.48-1.60 (m, 2H), 3.21, 3.41 (t, t, 2H), 3.65, 3.75 (s, s, 2H), 4.55, 4.66 (s, s, 2H), 5.60 (s, 2H), 6.84-7.43 (m, 9H), 7.62 (t, 1H), 7.85 (d, 1H) and 8.16

Example 11 a) N-Benzyl-N-hexyl-2-(4-hydroxy-3-methoxyphenyl)acetamide

Homovanillic acid (182 mg, 0.999 mmol) dissolved in DMF (3 ml) was cooled in an ice-bath. N-Hexylbenzylamine (201 mg, 1.049 mmol) was added and then TBTU (337 mg, 1.049 mmol) followed by DIPEA (407 mg, 3.147 mmol). The mixture was stirred at room temperature overnight and evaporated. Sodium hydrogencarbonate aqueous solution (sat.) was added into the residue. The mixture was then extracted with ethyl acetate (×2). The extracts were combined and washed with water and brine and dried (magnesium sulphate) and evaporated. Chromatography of the residue on a column (ISOLUTE® SI, 5 g/15 ml) using DCM and then MeOH/DCM (1:99) as eluant gave 264 mg the desired product, yield 74%.

$^1$H NMR (rotamers, 400 MHz, CDCl$_3$): δ 0.83-0.89 (m, 3H), 1.20-1.29 (m, 6H), 1.44-1.56 (m, 2H), 3.18, 3.37 (t, t, 2H), 3.60, 3.71 (s, s, 2H), 3.81 (s, br, 3H), 4.50, 4.61 (s, s, 2H), 5.98 (s, br, 1H), 6.62-6.85 (m, 3H) and 7.11-7.36 (m, 5H).

b) Methyl 2-[(4-{2-[benzyl(hexyl)amino]-2-oxoethyl}-2-methoxyphenoxy)methyl]benzoate N-Benzyl-N-hexyl-2-(4-hydroxy-3-methoxyphenyl)acetamide (84 mg, 0.236 mmol), 2-bromomethylbenzoic acid methyl ester (57 mg, 0.248 mmol) and potassium carbonate anhydrous (49 mg, 0.355 mmol) were mixed in acetonitrile (5 ml). The mixture was heated to reflux overnight and then evaporated to dry. Ethyl acetate and water were added and the two phases were separated. The organic phase was washed with brine and dried (magnesium sulphate) and evaporated. Chromatography of the residue on a column (ISOLUTE® SI, 2 g/6 ml) using DCM, MeOH/DCM (0.5:99.5) as eluant gave 102 mg the desired product yield 86%.

$^1$H NMR (rotamers, 400 MHz, CDCl$_3$): δ 0.82-0.88 (m, 3H), 1.18-1.28 (m, 6H), 1.43-1.55 (m, 2H), 3.17, 3.35 (t, t, 2H), 3.61, 3.71 (s, s, 2H), 3.86 (s, 3H), 3.88 (s, 3H), 4.48, 4.60 (s, s, 2H), 5.55, 5.56 (s, s, 2H), 6.61-7.35 (m, 9H), 7.52 (t, 1H), 7.78 (d, 1H) and 8.01 (d, 1H).

c) 2-[(4-{2-[Benzyl(hexyl)amino]-2-oxoethyl}-2-methoxyphenoxy)methyl]benzoic acid Methyl 2-[(4-{2-[benzyl(hexyl)amino]-2-oxoethyl}-2-methoxyphenoxy)methyl]benzoate (98 mg, 0.195 mmol) was dissolved in THF (2 ml). Lithium hydroxide (9.3 mg, 0.389 mmol) solved in water (1 ml) was added. The mixture was put in a microwave oven (Smith Synthesizer) at 150° C. for 7 minutes. It was then acidified with 1% hydrochloric acid, pH~3, and extracted with ethyl acetate. The organic extract was washed with brine and dried (magnesium sulphate) and evaporated. Chromatography of the residue on a column (ISOLUTE®) SI, 2 g/6 ml) using DCM and then MeOH/DCM (0.5:99.5, then 1:99) as eluant gave 43 mg the desired product, yield 45%.

$^1$H NMR (rotamers, 400 MHz, CDCl$_3$): δ 0.82-0.88 (m, 3H), 1.18-1.28 (m, 6H), 1.44-1.57 (m, 2H), 3.18, 3.37 (t, t, 2H), 3.64, 3.74 (s, s, 2H), 3.86 (s, 3H), 4.50, 4.62 (s, s, 2H), 5.57, 5.58 (s, s, 2H), 6.63-7.39 (m, 9H), 7.56 (t, 1H), 7.80 (d, 1H) and 8.12 (d, 1H).

Example 12 a) 4-[3-(3,4-Dihydroisoquinolin-2(1H)-yl)-3-oxopropyl]phenol 3-(4-Hydroxyphenyl)propionic acid (202 mg, 1.216 mmol) in DMF (3 ml) was cooled in an ice-bath. 1,2,3,4-Tetrahydroisoquinoline (170 mg, 1.276 mmol) was added and then TBTU (410 mg, 1.276 mmol) followed by DIPEA (330 mg, 2.553 mmol). The mixture was stirred at room temperature overnight. Sodium hydrogencarbonate aqueous solution (sat.) was added. The mixture was extracted with ethyl acetate (×2). The extracts were combined and dried (magnesium sulphate) and evaporated. Chromatography of the residue on a column (ISOLUTE® SI, 2 g/6 ml) using DCM and then MeOH/DCM (1:99) as eluant gave 303 mg the desired product, yield 89%.

$^1$H NMR (rotamers, 400 MHz, CDCl$_3$): δ 2.72-2.77 (m, 2H), 2.83-2.90 (m, 2H), 2.95-3.01 (m, 2H), 3.88 (t, t, 2H), 4.57, 4.79 (s, s, 2H), 6.85-6.90 (m, 2H) and 7.07-7.26 (m, 6H).

b) Methyl 2-({4-[3-(3,4-dihydroisoquinolin-2(1H)-yl)-3-oxopropyl]phenoxy}methyl)-benzoate 4-[3-(3,4-dihydroisoquinolin-2(1H)-yl)-3-oxopropyl] phenol (155 mg, 0.551 mmol) was dissolved in acetonitrile (10 ml). 2-Bromomethylbenzoic acid methyl ester (126 mg, 0.551 mmol) was added followed by potassium carbonate anhydrous (114 mg, 0.826 mmol). The mixture was heated to reflux overnight and then evaporated to dry. Water and ethyl acetate were added and two phases were separated. The organic phase was dried (magnesium sulphate) and evaporated. Column chromatography of the residue on silica gel using ethyl acetate/heptane (40:60) as eluant gave 135 mg the desired product, yield 57%.

$^1$H NMR (rotamers, 500 MHz, CDCl$_3$): δ 2.69-2.74 (m, 2H), 2.82-2.87 (m, 2H), 2.95-3.01 (m, 2H), 3.62, 3.85 (t, t, 2H), 3.93 (s, 3H), 4.52, 4.73 (s, s, 2H), 5.48, 5.50 (s, s, 2H), 6.91-6.95 (m, 2H), 7.03-7.24 (m, 6H), 7.39 (t, 1H), 7.57 (t, 1H), 7.77 (d, 1H) and 8.05 (d, 1H).

c) 2-({4-[3-(3,4-Dihydroisoquinolin-2(1H)-yl)-3-oxopropyl]phenoxy}methyl)benzoic acid Lithium hydroxide (14.4 mg, 0.6 mmol) dissolved in water (1 ml) was added into 70377 methyl 2-({4-[3-(3,4-dihydroisoquinolin-2(1H)-yl)-3-oxopropyl]phenoxy}methyl) benzoate (129 mg, 0.3 mmol) in THF (2 ml). The mixture was put in a microwave oven (Smith Synthesizer) and irradiated at 150° C. for 7 minutes and then evaporated to remove THF. The residue was acidified with 1% hydrochloric acid, pH~5, and extracted with ethyl acetate (×2). The extracts were combined and dried (magnesium sulphate) and evaporated. Chromatography of the residue on a column (ISOLUTE® SI, 2 g/6 ml) using DCM, MeOH/DCM (1:99) as eluant gave 111 mg the desired product yield 89%.

$^1$H NMR (rotamers, 400 MHz, CDCl$_3$): δ 2.70-2.73 (m, 2H), 2.79-2.83 (m, 2H), 2.92-3.00 (m, 2H), 3.58, 3.84 (t, t, 2H), 4.50, 4.76 (s, s, 2H), 5.50, 5.53 (s, s, 2H), 6.87-6.93 (m, 2H), 6.99-7.22 (m, 6H), 7.39 (t, 1H), 7.57 (t, 1H), 7.78 (d, 1H) and 8.16 (d, 1H).

Example 13 a) 4-(2-Hydroxyethyl)phenol (2 g, 14.48 mmol) and methyl 2-(bromomethyl)benzoate (3.48 g, 15.20 mmol) were dissolved in acetonitrile (20 ml). Potassium carbonate anhydrous (4.0 g, 28.95 mmol) was added. After stirring at 60° C. for three hours PS-trisamine was added (0.2 eq) and the mixture was stirred overnight. The PS-trisamine was filtered off and the acetonitrile was removed by evaporation. EtOAc (10 ml) was added and the organic layer was washed with 3 portions of water (3×10 ml). The organic phase was dried (MgSO$_4$) and the solvent was removed by evaporation to give 3.732 g of methyl 2-{[4-(2-hydroxyethyl)phenoxy] methyl}benzoate (yield 90%).

$^1$HNMR (300 MHz, CDCl$_3$): δ 2.37 (bs, 1H), 2.8 (t, 2H), 3.8 (bm, 2H), 3.9 (s, 3H), 5.5 (s, 2H), 6.95 (d, 2H), 7.15 (d, 2H), 7.25 (t, 1H), 7.55 (t, 1H), 7.75 (d, 1H), 8.05 (d, 1H)

b) Methyl 2-{[4-(2-hydroxyethyl)phenoxy]methyl}benzoate (1.2 g, 4.19 mmol) was dissolved in dichloromethane (20 ml) and the solution was cooled to −20° C. Triethylamine (0.64 g, 6.29 mmol) was added dropwise, and then methylsulfonyl chloride (0.53 g, 4.61 mmol) was added dropwise. The ice bath was removed and the mixture was stirred at room temperature for one hour. Diethyl ether (5 ml) was added and the precipitate was filtered off. The organic phase was washed with 2 portions of brine, dried (MgSO$_4$)

and the solvent was removed by evaporation. The crude was purified by preparative HPLC (starting with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. EtOAc (10 ml) was added and the organic phase was washed with two portions of brine and dried ($MgSO_4$). This gave 0.703 g of methyl 2-[(4-{2-[(methylsulfonyl)oxy]ethyl}phenoxy)-methyl]benzoate (yield 46%).

$^1$HNMR (300 MHz, $CDCl_3$): δ 2.8 (s, 3H), 2.95 (t, 2H), 3.85 (s, 3H), 4.35 (t, 2H), 5.45 (s, 2H), 6.9 (d, 2H), 7.15 (d, 2H), 7.35 (t, 1H), 7.5 (t, 1H), 7.7 (d, 1H), 7.98 (d, 1H)

c) Methyl 2-[(4-{2-[(methylsulfonyl)oxy]ethyl}phenoxy)methyl]benzoate (0.2 g, 0.55 mmol) and 4-(1H-imidazol-1-yl)phenol (0.11 g, 0.66 mmol) was dissolved in acetonitrile (10 ml) and potassium carbonate (0.09 g, 0.66 mmol) was added. The mixture was stirred over night at 75° C. Remove the acetonitrile by evaporation, dilute with EtOAc (10 ml) and wash the organic phase with Brine three times, dry ($MgSO_4$) and evaporate. This gave 0.268 g of methyl 2-[(4-{2-[4-(1H-imidazol-1-yl)phenoxy]ethyl}phenoxy)methyl]benzoate (yield 90%).

$^1$HNMR (300 MHz, $CDCl_3$): δ 3.05 (t, 2H), 3.9 (s, 3H), 4.05-4.2 (bm, 2H), 5.55 (s, 2H), 6.9-7.0 (bm, 4H), 7.1-7.4 (bm, 7H), 7.52 (t, 2H), 7.75 (m, 2H), 7.98 (d, 1H)

d) Methyl 2-[(4-{2-[4-(1H-imidazol-1-yl)phenoxy]ethyl}phenoxy)methyl]benzoate (0.12 g, 0.28 mmol) was dissolved in a mixture of THF/water (7/1, 5 ml) and LiOH (0.03 g, 1.13 mmol) was added. The reaction was performed in a single node microwave oven (7 min, 150° C.). Workup by addition of HCl (1 ml, 1M), extract the product by adding two portions of EtOAc (5 ml). The pooled organic phases were dried ($MgSO_4$) and the solvent was removed by evaporation. The crude was purified by preparative HPLC (starting with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. EtOAc (10 ml) was added and the organic phase was washed with two portions of brine and dried ($MgSO_4$). Evaporation gave 6 mg of 2-[(4-{2-[4-(1H-imidazol-1-yl)phenoxy]ethyl}-phenoxymethyl]benzoic acid (yield 4.7%).

$^1$HNMR (500 MHz, $CDCl_3$): δ 3.05 (t, 2H), 4.18 (t, 2H), 5.55 (s, 2H), 6.95 (d, 2H), 7.05 (m, 3H), 7.25 (d, 2H), 7.3-7.45 (bm, 4H), 7.55 (t, 1H), 7.78 (d, 1H), 7.85 (s, 1H), 8.07 (d, 1H).

Example 14 a) 4-(2-Hydroxyethyl)phenol (2 g, 14.48 mmol) and methyl 2-(bromomethyl)benzoate (3.48 g, 15.20 mmol) was dissolved in acetonitrile (20 ml). Potassium carbonate anhydrous (4.0 g, 28.95 mmol) was added. After stirring at 60° C. for three hours PS-trisamine was added (0.2 eq) and was stirred overnight. The PS-trisamine was filtered of and the acetonitrile was removed by evaporation. EtOAc (10 ml) was added and the organic layer was washed with 3 portions of water (3×10 ml). The organic phase was dried ($MgSO_4$) and the solvent was removed by evaporation to give 3.732 g of methyl 2-{[4-(2-hydroxyethyl)phenoxy]methyl}benzoate (yield 90%).

$^1$HNMR (300 MHz, $CDCl_3$): δ 2.37 (bs, 1H), 2.8 (t, 2H), 3.8 (bm, 2H), 3.9 (s, 3H), 5.5 (s, 2H), 6.95 (d, 2H), 7.15 (d, 2H), 7.25 (t, 1H), 7.55 (t, 1H), 7.75 (d, 1H), 8.05 (d, 1H)

b) Methyl 2-{[4-(2-hydroxyethyl)phenoxy] methyl}benzoate (1 g, 3.49 mmol), 4-(benzyloxy)phenol (0.7 g, 3.49 mmol) and triphenylphosphine (1.01 g, 3.84 mmol) was added to a dry round bottomed flask fitted with a septum. $N_2$ was flushed through the flask for 5 minutes followed by the addition of dry toluene (30 ml) and diisopropylazo-dicarboxylate (0.78 g, 3.84 mmol). The reaction mixture was stirred at 55° C. overnight. The solvent was removed by evaporation and the crude material was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. EtOAc (10 ml) was added and the organic phase was washed with two portions of brine and dried ($MgSO_4$). After removing the solvent by evaporation, 0.7 g of methyl 2-[(4-{2-[4-(benzyloxy)phenoxy]ethyl}phenoxy)methyl]benzoate was isolated (yield 42.8%).

$^1$HNMR (300 MHz, $CDCl_3$,): δ 3.05 (t, 2H), 3.95 (s, 3H), 4.07 (t, 2H), 5.03 (s, 2H), 5.55 (s, 2H), 6.85 (d, 2H), 6.95 (d, 2H), 6.98 (d, 2H), 7.23 (d, 2H), 7.3-7.5 (bm, 6H), 7.6 (t, 1H), 7.8 (d, 1H), 8.07 (d, 1H).

c) Methyl 2-[(4-{2-[4-(benzyloxy)phenoxy]ethyl}phenoxy)methyl]benzoate (0.80 g 1.71 mmol), borontrifluoride etherate (2.42 g, 17.09 mol) and dimethyl sulfide (1.27 g, 20.51 mmol) were dissolved in dicloromethane (25 ml). The mixture was stirred for 6 hours at room temperature. EtOAc (20 ml) was added and the mixture was washed with three portions of water, the organic layer dried ($MgSO_4$) and the solvent removed by evaporation.

$^1$HNMR (300 MHz, $CDCl_3$): δ 3.0 (t, 2H), 3.9 (s, 3H), 4.1 (t, 2), 5.5 (s, 2H), 5.55 (s, 2H), 6.8 (bm, 4H), 7.0 (d, 2H), 7.2 (d, 2H), 7.4 (t, 1H), 7.55 (t, 1H), 7.8 (d, 1H), 8.05 (d, d) Methyl 2-({4-[2-(4-hydroxyphenoxy)ethyl]phenoxy}methyl)benzoate (0.547 g, 1.45 mmol) was dissolved in dichloromethane (10 ml) and the solution was cooled to −20° C. Triethylamine (0.22 g, 2.17 mmol) was added dropwise followed by the dropwise addition of methylsulfonyl chloride (0.18 g, 1.59 mmol). The ice bath was removed and the mixture was stirred overnight at room temperature. Excess of triethylamine was removed by addition of diethyl ether (5 ml) and filtering off the precipitate. The organic phase was washed with three portions of brine (10 ml) and dried ($MgSO_4$). The solvent was removed by evaporation, the crude was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min)). The product containing fractions were pooled and the acetonitrile was removed by evaporation. EtOAc (10 ml) was added and the organic phase was washed with two portions of brine and dried ($MgSO_4$). Removing the solvent by evaporation gave 0.317 g of methyl 2-{[4-(2-{4-[(methylsulfonyl)oxy] phenoxy}ethyl)phenoxy]methyl}benzoate (yield 48%).

$^1$HNMR (500 MHz, $CDCl_3$): δ 3.07 (t, 2H), 3.15 (s, 3H), 3.95 (s, 3H), 4.17 (t, 2H), 5.55 (s, 2H), 6.95 (d, 2H), 7.0 (d, 2H), 7.23 (m, 4H), 7.42 (t, 1H), 7.6 (t, 1H), 7.8 (d, 1H), 8.08 (d, 1H).

e) Methyl 2-{[4-(2-{4-[(methylsulfonyl)oxy] phenoxy}ethyl)phenoxy]methyl}benzoate (0.18 g, 0.38 mmol) was dissolved in a mixture of tetrahydrofuran and water 7:1 (5 ml). The reaction was performed in a single node microwave oven (150° C. in 7 minutes). The mixture was diluted with HCl (2 ml, 1 M) and the organic phase was isolated. The crude was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. EtOAc (10 ml) was added and the organic phase was washed with two portions of brine and dried ($MgSO_4$). Removing the solvent by evaporation gave 13 mg of 2-{[4-(2-{4-[(methylsulfonyl)oxy]phenoxy}ethyl) phenoxy]-methyl}benzoic acid (yield 7.7%).

$^1$HNMR (300 MHz, $CDCl_3$): δ 3.07 (t, 2H), 3.15 (s, 3H), 4.17 (t, 2H) 5.6 (s, 2H), 6.95 (d, 2H), 7.0 (d, 2H), 7.23 (m, 4H), 7.42 (t, 1H), 7.65 (t, 1H), 7.82 (d, 1H), 8.2 (d, 1H).

Example 15 a) 3-(2-Hydroxyethyl)phenol (1.0 g, 7.24 mmol) and methyl 2-(bromomethyl)benzoate (1.74 g, 7.6 mmol) were dissolved in acetonitrile (10 ml). Potassium carbonate anhydrous (2.0 g, 14.48 mmol) was added. After stirring at 60° C. for three hours PS-trisamine was added (0.3 eq) and was stirred overnight. The PS-trisamine was filtered off and the acetonitrile was removed by evaporation. EtOAc (10 ml) was added and the organic layer was washed with 3 portions of water (3×10 ml). The organic phase was dried ($MgSO_4$) and the solvent was removed by evaporation to give 1.99 g of methyl 2-{[3-(2-hydroxyethyl)phenoxy]methyl}benzoate (yield 90%).

1HNMR (300 MHz, $CDCl_3$): δ 2.95 (t, 2H), 3.45 (s, 1H), 3.9-4.0 (bm, 5H), 5.58 (s, 2H), 6.95 (m, 2H), 7.05 (s, 1H), 7.3 (t, 1H), 7.45 (t, 1H), 7.6 (t, 1H), 7.85 (d, 1H), 8.05 (d, 1H)

b) Methyl 2-{[3-(2-hydroxyethyl)phenoxy] methyl}benzoate (0.5 g, 1.75 mmol), 4-(benzyloxy)phenol (0.35 g, 1.75 mmol) and triphenylphosphine (0.5 g, 1.92 mmol) were added to a dry roundbottomed flask and fitted with a septum Dry toluene (10 ml) was added and $N_2$ was flushed through the mixture for 5 minutes. Diisopropyl (E)-diazene-1,2-dicarboxylate (0.39 g, 1.92 mmol) was added dropwise and the solution was stirred at room temperature. After three hour, another equivalent of reagents was added and stirred for one hour. After removing the solvent by evaporation the crude was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions was pooled and the acetonitrile was removed by evaporation EtOAc (10 ml) was added and the organic phase was washed with two portions of brine and dried ($MgSO_4$). Removing the solvent by evaporation gave 0.319 g methyl 2-[(3-{2-[4-(benzyloxy)phenoxy] ethyl}phenoxy)methyl]benzoate (yield 39%).

$^1$HNMR (300 MHz, $CDCl_3$): δ 3.15 (t, 2H), 3.95 (s, 3H), 4.2 (t, 2H), 5.07 (s, 2H), 5.6 (s, 2H), 6.9-7.1 (bm, 7H), 7.3-7.55 (bm, 7H), 7.6 (t, 1H), 7.85 (d, 1H), 8.05 (d, 1H)

c) Methyl 2-[(3-{2-[4-(benzyloxy)phenoxy] ethyl}phenoxy)methyl]benzoate (20 mg, 0.043 mmol) was dissolved in a mixture of $THF/H_2O$ (7/1, 3 ml) and LiOH (4.1 mg, 0.17 mmol) was added. The reaction was performed in a single node microwave oven (7 min, 150° C.). The mixture was acidified (HCl, 1 ml, 1M) and the water phase washed with two portions of EtOAc (3×5 ml). After removing the solvent by evaporation the crude was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min)). The product containing fractions were pooled and the acetonitrile was removed by evaporation. EtOAc (10 ml) was added and the organic phase was washed with two portions of brine and dried ($MgSO_4$). Removing the solvent by evaporation gave 19 mg of 2-[(3-{2-[4-(benzyloxy)phenoxy]ethyl}phenoxy)methyl]benzoic acid (yield 98%).

$^1$HNMR (300 MHz, $CDCl_3$): δ 3.1 (t, 2H), 4.15 (t, 2H), 5.03 (s, 2H), 5.57 (s, 2H), 6.8-7.0 (bm, 7H), 7.2-7.5 (bm, 7H), 7.6 (t, 1H), 7.85 (d, 1H), 8.15 (d, 1H)

Example 16 a) 3-(2-Hydroxyethyl)phenol (1.0 g, 7.24 mmol) and methyl 2-(bromomethyl)benzoate (1.74 g, 7.6 mmol) were dissolved in acetonitrile (10 ml). Potassium carbonate anhydrous (2.0 g, 14.48 mmol) was added. After stirring at 60° C. for three hours PS-trisamine was added (0.3 eq) and was stirred overnight. The PS-trisamine was filtered off and the acetonitrile was removed by evaporation. EtOAc (10 ml) was added and the organic layer was washed with 3 portions of water (3×10 ml). The organic phase was dried ($MgSO_4$) and the solvent was removed by evaporation to give 1.99 g of methyl 2-{[3-(2-hydroxyethyl)phenoxy]methyl}benzoate (yield 90%).

$^1$HNMR (300 MHz, $CDCl_3$): δ 2.95 (t, 2H), 3.45 (s, 1H), 3.9-4.0 (bm, 5H), 5.58 (s, 2H), 6.95 (m, 2H), 7.05 (s, 1H), 7.3 (t, 1H), 7.45 (t, 1H), 7.6 (t, 1H), 7.85 (d, 1H), 8.05 (d, 1H)

b) Methyl 2-{[3-(2-hydroxyethyl)phenoxy] methyl}benzoate (0.5 g, 1.75 mmol), 4-(benzyloxy)phenol (0.35 g, 1.75 mmol) and triphenylphosphine (0.5 g, 1.92 mmol) was added to a dry round bottomed flask and fitted with septum. Dry toluene (10 ml) was added and $N_2$ was flushed through the mixture for 5 minutes. Diisopropyl (E)-diazene-1,2-dicarboxylate (0.39 g, 1.92 mmol) was added dropwise and the solution was stirred at room temperature. After three hours another equivalent of reagents was added and stirred for one hour. After removing the solvent by evaporation the crude was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min)). The product containing fractions were pooled and the acetonitrile was removed by evaporation. EtOAc (10 ml) was added and the organic phase was washed with two portions of brine and dried ($MgSO_4$). Removing the solvent by evaporation gave 0.319 g methyl 2-[(3-{2-[4-(benzyloxy)phenoxy] ethyl}phenoxy)methyl]benzoate (yield 39%).

$^1$HNMR (300 MHz, $CDCl_3$): δ 3.15 (t, 2H), 3.95 (s, 3H), 4.2 (t, 2H), 5.07 (s, 2H), 5.6 (s, 2H), 6.9-7.1 (bm, 7H), 7.3-7.55 (bm, 7H), 7.6 (t, 1H), 7.85 (d, 1H), 8.05 (d, 1H)

c) Methyl 2-[(3-{2-[4-(benzyloxy)phenoxy] ethyl}phenoxy)methyl]benzoate (0.275 g, 0.59 mmol) was dissolved in dichloromethane (10 ml), dimethylsulfide (0.44 g, 7.0 mmol) and borontrifloureide eterate (0.83 g, 5.87 mmol) was added and the mixture was stirred at room temperature for six hours. EtOAc (10 ml) was added and the organic phase was washed with water (3×10 ml), dried ($MgSO_4$) and the solvent was removed by evaporation and the crude was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions was pooled and the acetonitrile was removed by evaporation. EtOAc (10 ml) was added and the organic phase was washed with two portions of brine and dried (MgSO$_4$). After removing the solvent by evaporation 0.096 gram of methyl 2-({3-[2-(4-hydroxyphenoxy)ethyl]-phenoxy}methyl)benzoate was obtained (yield 43.2%). This product was used directly in the next step.

d) Methyl 2-({3-[2-(4-hydroxyphenoxy)ethyl]phenoxy}methyl)benzoate (0.096 g, 0.25 mmol) was dissolved in dichloromethane (10 ml) and cooled to −20° C. Triethylamine (0.039 g, 0.38 mmol) was added drop wise and methanesulfonyl chloride (0.032 g, 0.28 mmol) was added drop wise. The ice bath was removed and the mixture was wormed to room temperature. Diethyl ether (5 ml) was added and the precipitate filtered off. The organic phase was washed with two portions of brine (5 ml) and dried (MgSO$_4$). Removing The solvent was removed by evaporation giving 0.109 gram of methyl 2-{[3-(2-{4-[(methylsulfonyl)oxy]phenoxy}-ethyl)phenoxy]methyl}benzoate (yield 94.1%).

$^1$HNMR (500 MHz, CDCl$_3$): δ 3.15 (m, 5H), 3.95 (s, 3H), 4.2 (t, 2H), 5.55 (s, 2H), 6.95 (s, 4H), 7.0 (s, 1H), 7.25 (d, 2H), 7.3 (t, 1H), 7.42 (t, 1H), 7.6 (t, 1H), 7.8 (d, 1H), 8.1 (d, 1H).

e) Methyl 2-{[3-(2-{4-[(methylsulfonyl)oxy]phenoxy}ethyl)phenoxy]methyl}benzoate (0.109 g, 0.24 mmol) was dissolved in a mixture of THF/water (7/1, 2.5 ml). Lithium hydroxide (23 mg, 0.96 mmol) was added. The reaction was performed in a single node microwave oven (7 min, 150° C.). The mixture was acidified (HCl, 1 ml, 1 M) and the water phase was extracted with two portions of EtOAc (2×5 ml). The organic phases were combined, dried (MgSO$_4$) and the solvent was removed by evaporation and gave 17 mg of 2-{[3-(2-{4-[(methylsulfonyl)oxy]phenoxy}ethyl)phenoxy]methyl}benzoic acid (yield 16%).

$^1$HNMR (500 MHz, CDCl$_3$): δ 3.15 (m, 5H), 4.2 (t, 2H), 5.55 (s, 2H), 6.95 (s, 4H), 7.0 (s, 1H), 7.25 (d, 2H), 7.3 (t, 1H), 7.42 (t, 1H), 7.6 (t, 1H), 7.8 (d, 1H), 8.1 (d, 1H).

Example 17 a) 3-(2-Hydroxyethyl)phenol (1.0 g, 7.24 mmol) and methyl 2-(bromomethyl)benzoate (1.74 g, 7.6 mmol) was dissolved in acetonitrile (10 ml). Potassium carbonate anhydrous (2.0 g, 14.48 mmol) was added. After stirring at 60° C. for three hours PS-trisamine was added (0.3 eq) and was stirred overnight. The PS-trisamine was filtered off and the acetonitrile was removed by evaporation. EtOAc (10 ml) was added and the organic layer was washed with 3 portions of water (3×10 ml). The organic phase was dried (MgSO$_4$) and the solvent was removed by evaporation to give 1.99 g of methyl 2-{[3-(2-hydroxyethyl)phenoxy]methyl}benzoate (yield 90%).

$^1$HNMR (300 MHz, CDCl$_3$): δ 2.95 (t, 2H), 3.45 (s, 1H), 3.9-4.0 (bm, 5H), 5.58 (s, 2H), 6.95 (m, 2H), 7.05 (s, 1H), 7.3 (t, 1H), 7.45 (t, 1H), 7.6 (t, 1H), 7.85 (d, 1H), 8.05 (d, 1H)

b) Methyl 2-{[3-(2-hydroxyethyl)phenoxy]methyl}benzoate (0.5 g, 1.75 mmol), 4-(benzyloxy)phenol (0.35 g, 1.75 mmol) and triphenylphosphine (0.5 g, 1.92 mmol) was added to a dry round bottomed flask and fitted with septum. Dry toluene (10 ml) was added and N$_2$ was flushed through the mixture for 5 minutes. Diisopropyl (E)-diazene-1,2-dicarboxylate (0.39 g, 1.92 mmol) was added dropwise and the solution was stirred at room temperature. After three hours another equivalent of reagents was added and stirred for one hour. After removing the solvent by evaporation the crude was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min)). The product containing fractions were pooled and the acetonitrile was removed by evaporation. EtOAc (10 ml) was added and the organic phase was washed with two portions of brine and dried (MgSO$_4$). Removing the solvent by evaporation gave 0.319 g methyl 2-[(3-{2-[4-(benzyloxy)phenoxy]ethyl}phenoxy)methyl]benzoate (yield 39%).

$^1$HNMR (300 MHz, CDCl$_3$): δ 3.15 (t, 2H), 3.95 (s, 3H), 4.2 (t, 2H), 5.07 (s, 2H), 5.6 (s, 2H), 6.9-7.1 (bm, 7H), 7.3-7.55 (bm, 7H), 7.6 (t, 1H), 7.85 (d, 1H), 8.05 (d, 1H)

c) Methyl 2-[(3-{2-[4-(benzyloxy)phenoxy]ethyl}phenoxy)methyl]benzoate (0.275 g, 0.59 mmol) was dissolved in dichloromethane (10 ml), dimethyl sulfide (0.44 g, 7.0 mmol) and borontrifluoride etherate (0.83 g, 5.87 mmol) was added and the mixture was stirred at room temperature for six hours. EtOAc (10 ml) was added and the organic phase was washed with water (3×10 ml), dried (MgSO$_4$) and the solvent was removed by evaporation and the crude was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min)). The product containing fractions were pooled and the acetonitrile was removed by evaporation. EtOAc (10 ml) was added and the organic phase was washed with two portions of brine and dried (MgSO$_4$). After removing the solvent by evaporation 0.096 gram of methyl 2-({3-[2-(4-hydroxyphenoxy)ethyl]-phenoxy}methyl)benzoate was obtained (yield 43.2%). This product was used directly in the next step.

d) Methyl 2-({3-[2-(4-hydroxyphenoxy)ethyl]phenoxy}methyl)benzoate (0.096 g, 0.25 mmol) was dissolved in dichloromethane (10 ml) and cooled to −20° C. Triethylamine (0.039 g, 0.38 mmol) was added drop wise and methanesulfonyl chloride (0.032 g, 0.28 mmol) was added drop wise. The ice bath was removed and the mixture was wormed to room temperature. Add diethyleter (5 ml) and filter of the precipitate, wash the organic phase with two portions of brine (5 ml) and dry (MgSO$_4$). Removing the solvent by evaporation gave 0.109 gram of methyl 2-{[3-(2-{4-[(methylsulfonyl)oxy]phenoxy}ethyl)-phenoxy]methyl}benzoate (yield 94.1%).

$^1$HNMR (500 MHz, CDCl$_3$): δ 3.15 (m, 5H), 3.95 (s, 3H), 4.2 (t, 2H), 5.55 (s, 2H), 6.95 (s, 4H), 7.0 (s, 1H), 7.25 (d, 2H), 7.3 (t, 1H), 7.42 (t, 1H), 7.6 (t, 1H), 7.8 (d, 1H), 8.1 (d, 1H).

f) Methyl 2-{[3-(2-{4-[(methylsulfonyl)oxy]phenoxy}ethyl)phenoxy]methyl}benzoate (0.109 g, 0.24 mmol) was dissolved in a mixture of THF/water (7/1, 2.5 ml). Lithium hydroxide (23 mg, 0.96 mmol) was added. The reaction was performed in a single node microwave oven (7 min, 150° C.). The mixture was acidified (HCl, 1 ml, 1 M) and the water phase was extracted with two portions of EtOAc. The organic phases were combined, dried (MgSO$_4$) and the solvent was removed by evaporation and gave 16 mg of 2-({3-[2-(4-hydroxyphenoxy)ethyl]phenoxy}methyl)benzoic acid (yield 18%)

$^1$HNMR (400 MHz, CDCl$_3$): δ 3.0 (t, 2H), 4.1 (t, 2H), 5.55 (s, 2H), 6.7 (m, 4H), 6.8-6.95 (bm, 3H), 7.4 (m, 1H), 7.6 (1, 1H), 7.8 (m, 1H), 8.15 (m, 1H).

Example 18 a) 4-(3-Hydroxypropyl)phenol (1.0 g, 6.57 mmol) and methyl 2-(bromomethyl)benzoate (1.66 g, 7.23 mmol) was dissolved in acetonitrile (10 ml). Potassium carbonate (1.82 g, 13.14 mmol) was added and the mixture was stirred at 60° C. for three hours. Polymer supported trisamine (0.3 eqv) was added and the solution was stirred at room temperature overnight. The PS-trisamine was filtered of and the acetonitrile was removed by evaporation. EtOAc (10 ml) was added and the organic layer was washed with 3 portions of water (3×10 ml). The organic phase was dried (MgSO$_4$) and the solvent was removed by evaporation to give 1.66 gram of methyl 2-{[4-(3-hydroxypropyl)phenoxy]-methyl}benzoate (yield 84.2%).

$^1$HNMR (500 MHz, CDCl$_3$): δ 1.9 (m, 2H), 2.65 (t, 2H), 3.25 (s, 1H), 3.65 (t, 2H), 3.85 (s, 3H), 5.45 (s, 2H), 6.95 (d, 2H), 7.15 (d, 2H), 7.35 (t, 1H), 7.5 (t, 1H), 7.75 (d, 1H), 8.05 (d, 1H).

b) Methyl 2-{[4-(3-hydroxypropyl)phenoxy]methyl}benzoate (0.50 g, 1.66 mmol) and 4-(benzyloxy)phenol (0.33 g, 1.66 mmol) was added to a dry round bottomed flask fitted with a septum Dry toluene (10 ml) was added and N$_2$ was flushed through the mixture for 5 minutes. (Tributylphosphoranylidene)acetonitrile (0.80 g, 3.33 mmol) was added dropwise and the reaction was performed in a single node microwave oven. After removing the solvent by evaporation the crude was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min)). The product containing fractions were pooled and the acetonitrile was removed by evaporation. EtOAc (10 ml) was added and the organic phase was washed with two portions of brine and dried (MgSO$_4$). Removing the solvent by evaporation gave 0.515 gram of methyl 2-[(4-{3-[4-(benzyloxy)phenoxy]-propyl}phenoxy)methyl]benzoate (yield 64.1%).

$^1$HNMR (500 MHz, CDCl$_3$): δ 2.15 (m, 2H), 2.85 (t, 2H), 4.0 (m, 5H), 5.1 (s, 2H), 5.6 (s, 2H), 6.9-7.1 (bm, 6H), 7.22 (d, 2H), 7.35-7.55 (bm, 6H), 7.62 (t, 1H), 7.9 (d, 1H), 8.15 (d, 1H).

c) Methyl 2-[(4-{3-[4-(benzyloxy)phenoxy]propyl}phenoxy)methyl]benzoate (0.047 g, 0.097 mmol) was dissolved in a mixture of THF/water (7/1, 2 ml) and lithium hydroxide (9.3 mg, 0.39 mmol) was added. The reaction was performed in a single node microwave oven (7 min, 150° C.). The reaction mixture was acidified (HCl, 1 M, 1 ml) and the water phase was washed with two portions of EtOAc (2×5 ml). The organic phases were combined, dried (MgSO$_4$) and the solvent was removed by evaporation. The crude product was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min)). The product containing fractions were pooled and the acetonitrile was removed by evaporation. EtOAc (10 ml) was added and the organic phase was washed with two portions of brine and dried (MgSO$_4$). Removing the solvent by evaporation gave 2 mg of 2-[(4{3-[4-(benzyloxy)phenoxy]propyl}phenoxy)methyl]-benzoic acid (yield 4.4%).

$^1$HNMR (500 MHz, CDCl$_3$): δ 2.05 (m, 2H), 2.75 (t, 2H), 4.0 (t, 2H), 5.05 (s, 2H), 5.6 (s, 2H), 6.8-7.0 (bm, 6H), 7.15 (d, 2H), 7.35-7.55 (bm, 6H), 7.55 (t, 1H), 7.8 (d, 1H), 8.15 (d, 1H).

Example 19 a) 4-(3-Hydroxypropyl)phenol (1.0 g, 6.57 mmol) and methyl 2-(bromomethyl)benzoate (1.66 g, 7.23 mmol) was dissolved in acetonitrile (10 ml). Potassium carbonate (1.82 g, 13.14 mmol) was added and the mixture was stirred at 60° C. for three hours. Polymer supported trisamine (0.3 eqv) was added and the solution was stirred at room temperature overnight. The PS-trisamine was filtered off and the acetonitrile was removed by evaporation EtOAc (10 ml) was added and the organic layer was washed with 3 portions of water (3×10 ml). The organic phase was dried (MgSO$_4$) and the solvent was removed by evaporation to give 1.66 gram of methyl 2-{[4-(3-hydroxypropyl)phenoxy]-methyl}benzoate (yield 84.2%).

$^1$HNMR (500 MHz, CDCl$_3$): δ 1.9 (m, 2H), 2.65 (t, 2H), 3.25 (s, 1H), 3.65 (t, 2H), 3.85 (s, 3H), 5.45 (s, 2H), 6.95 (d, 2H), 7.15 (d, 2H), 7.35 (t, 1H), 7.5 (t, 1H), 7.75 (d, 1H), 8.05 (d, 1H).

b) Methyl 2-{[4-(3-hydroxypropyl)phenoxy]methyl}benzoate (0.50 g, 1.66 mmol) and 4-(benzyloxy)phenol (0.33 g, 1.66 mmol) was added to a dry round bottomed flask and fitted with septa. Dry toluene (10 ml) was added and N$_2$ was flushed through the mixture for 5 minutes. (Tributylphosphoranylidene)acetonitrile (0.80 g, 3.33 mmol) was added dropwise and the reaction was performed in a single node microwave oven. After removing the solvent by evaporation the crude was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min)). The product containing fractions were pooled and the acetonitrile was removed by evaporation. EtOAc (10 ml) was added and the organic phase was washed with two portions of brine and dried (MgSO$_4$). Removing the solvent by evaporation gave 0.515 gram of methyl 2-[(4-{3-[4-(benzyloxy)phenoxy]-propyl}phenoxy)methyl]benzoate (yield 64.1%).

$^1$HNMR (500 MHz, CDCl$_3$): δ 2.15 (m, 2H), 2.85 (t, 2H), 4.0 (m, 5H), 5.1 (s, 2H), 5.6 (s, 2H), 6.9-7.1 (bm, 6H), 7.22 (d, 2H), 7.35-7.55 (bm, 6H), 7.62 (t, 1H), 7.9 (d, 1H), 8.15 (d, 1H).

c) Methyl 2-[(4-{3-[4-(benzyloxy)phenoxy]propyl}phenoxy)methyl]benzoate (0.70 g, 1.45 mmol) was dissolved in dichloromethane (10 ml). Dimethylsulfide (1.08 g, 17.4 mmol) and boron trifluoride etherate (2.06 g, 14.5 mmol) was added and the mixture was stirred at room temperature for six hours. EtOAc (10 ml) was added and the organic phase was washed with water (3×10 ml), dried (MgSO$_4$) and the solvent was removed by evaporation. The crude was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min)). The product containing fractions were pooled and the acetonitrile was removed by evaporation. EtOAc (10 ml) was added and the organic phase was washed with two portions of brine and dried (MgSO$_4$). After removing the solvent by evaporation 0.328 gram of methyl 2-({4-[3-(4-hydroxyphenoxy)propyl]-phenoxy}methyl)benzoate (yield 57.6%) was obtained.

$^1$HNMR (500 MHz, CDCl$_3$): δ 2.05 (m, 2H), 2.75 (t, 2H), 3.9 (m, 5H), 5.5 (s, 2H), 6.65-6.8 (bm, 4H), 6.95 (d, 2H), 7.15 (d, 2H), 7.4 (t, 1H), 7.55 (t, 1H), 7.8 (d, 1H), 8.05 (d, 1H).

d) Methyl 2-({4-[3-(4-hydroxyphenoxy)propyl]phenoxy}methyl)benzoate (0.32 g, 0.81 mmol) was dissolved in dichloromethane (10 ml) and cooled to −20° C. Triethylamine (0.123 g, 1.22 mmol) was added drop wise and methanesulfonyl chloride (0.10 g, 0.89 mmol) was added drop wise. The ice bath was removed and the mixture was wormed to room temperature. Diethyl ether (5 ml) was added and the precipitate was filtered off. The organic phase was washed with two portions of brine (5 ml) and dried (MgSO$_4$). Removing the solvent by evaporation gave 0.37 gram of methyl 2-{[4-(3-{4-[(methylsulfonyl)oxy]-phenoxy}propyl)phenoxy]methyl}benzoate (yield 97.3%).

$^1$HNMR (500 MHz, CDCl$_3$): δ 2.1 (m, 2H), 2.75 (t, 2H), 3.15 (s, 3H), 3.9 (m, 5H), 5.5 (s, 2H), 6.9-7.0 (bm, 4H), 7.15 (d, 2H), 7.22 (d, 2H), 7.4 (t, 1H), 7.55 (t, 1H), 7.8 (d, 1H), 8.05 (d, 1H).

e) Methyl 2-{[4-(3-{4-[(methylsulfonyl)oxy]phenoxy}propyl)phenoxy]methyl}benzoate (0.38 g, 0.81 mmol) was dissolved in a mixture of THF/water (7/1, 4 ml) and lithium hydroxide (9.3 mg, 0.39 mmol) was added. The reaction was performed in a single node microwave oven (7 min, 150° C.). The reaction mixture was acidified (HCl, 1 M, 1 ml) and the water phase was washed with two portions of EtOAc (2×5 ml). The organic phases were combined, dried (MgSO$_4$) and the solvent was removed by evaporation The crude was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min)). The product containing fractions were pooled and the acetonitrile was removed by evaporation. EtOAc (10 ml) was added and the organic phase was washed with two portions of brine and dried (MgSO$_4$). Removing the solvent by evaporation gave 88 mg of 2-{[4-(3-{4-[(methylsulfonyl)oxy]phenoxy}propyl)phenoxy]-methyl}benzoic acid (yield 23.7%).

$^1$HNMR (500 MHz, CDCl$_3$): δ 2.1 (m, 2H), 2.75 (t, 2H), 3.15 (s, 3H), 3.95 (t, 2H), 5.58 (s, 2H), 6.9-7.05 (bm, 4H), 7.15-7.25 (bm, 4H), 7.45 (t, 1H), 7.65 (t, 1H), 7.85 (d, 1H), 8.2 (d, 1H).

Example 20 a) 4-(3-Hydroxypropyl)phenol (1.0 g, 6.57 mmol) and methyl 2-(bromomethyl)benzoate (1.66 g, 7.23 mmol) was dissolved in acetonitrile (10 ml). Potassium carbonate (1.82 g, 13.14 mmol) was added and the mixture was stirred at 60° C. for three hours. Polymer supported trisamine (0.3 eqv) was added and the solution was stirred at room temperature overnight. The PS-trisamine was filtered off and the acetonitrile was removed by evaporation. EtOAc (10 ml) was added and the organic layer was washed with 3 portions of water (3×10 ml). The organic phase was dried (MgSO$_4$) and the solvent was removed by evaporation to give 1.66 gram of methyl 2-{[4-(3-hydroxypropyl)phenoxy]-methyl}benzoate (yield 84.2%).

$^1$HNMR (500 MHz, CDCl$_3$): δ 1.9 (m, 2H), 2.65 (t, 2H), 3.25 (s, 1H), 3.65 (t, 2H), 3.85 (s, 3H), 5.45 (s, 2H), 6.95 (d, 2H), 7.15 (d, 2H), 7.35 (t, 1H), 7.5 (t, 1H), 7.75 (d, 1H), 8.05 (d, 1H).

b) Methyl 2-{[4-(3-hydroxypropyl)phenoxy]methyl}benzoate (0.50 g, 1.66 mmol) and 4-(benzyloxy)phenol (0.33 g, 1.66 mmol) was added to a dry round bottomed flask and fitted with a septum Dry toluene (10 ml) was added and N$_2$ was flushed through the mixture for 5 minutes. (Tributylphosphoranylidene)acetonitrile (0.80 g, 3.33 mmol) was added drop wise and the reaction was performed in a single node microwave oven. After removing the solvent by evaporation the crude was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min)). The product containing fractions were pooled and the acetonitrile was removed by evaporation. EtOAc (10 ml) was added and the organic phase was washed with two portions of brine and dried (MgSO$_4$). Removing the solvent by evaporation gave 0.515 gram of methyl 2-[(4-{3-[4(benzyloxy)phenoxy]-propyl}phenoxy)methyl]benzoate (yield 64.1%).

$^1$HNMR (500 MHz, CDCl$_3$): δ 2.15 (m, 2H), 2.85 (t, 2H), 4.0 (m, 5H), 5.1 (s, 2H), 5.6 (s, 2H), 6.9-7.1 (bm, 6H), 7.22 (d, 2H), 7.35-7.55 (bm, 6H), 7.62 (t, 1H), 7.9 (d, 1H), 8.15 (d, 1H).

c) Methyl 2-[(4-{3-[4(benzyloxy)phenoxy]propyl}phenoxy)methyl]benzoate (0.70 g, 1.45 mmol) was dissolved in dichloromethane (10 ml). Dimethylsulfide (1.08 g, 17.4 mmol) and borontrifluoride etherate (2.06 g, 14.5 mmol) was added and the mixture was stirred at room temperature for six hours. EtOAc (10 ml) was added and the organic phase was washed with water (3×10 ml), dried (MgSO$_4$) and the solvent was removed by evaporation. The crude was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min)). The product containing fractions were pooled and the acetonitrile was removed by evaporation. EtOAc (10 ml) was added and the organic phase was washed with two portions of brine and dried (MgSO$_4$). After removing the solvent by evaporation 0.328 gram of methyl 2-({4-[3-(4-hydroxyphenoxy)propyl]-phenoxy}methyl)benzoate (yield 57.6%) was obtained.

$^1$HNMR (500 MHz, CDCl$_3$): δ 2.05 (m, 2H), 2.75 (t, 2H), 3.9 (m, 5H), 5.5 (s, 2H), 6.65-6.8 (bm, 4H), 6.95 (d, 2H), 7.15 (d, 2H), 7.4 (t, 1H), 7.55 (t, 1H), 7.8 (d, 1H), 8.05 (d, 1H).

d) Methyl 2-({4-[3-(4-hydroxyphenoxy)propyl]phenoxy}methyl)benzoate (0.32 g, 0.81 mmol) was dissolved in dichloromethane (10 ml) and cooled to −20° C. Triethylamine (0.123 g, 1.22 mmol) was added drop wise and methanesulfonyl chloride (0.10 g, 0.89 mmol) was added drop wise. The ice bath was removed and the mixture was wormed to room temperature. Diethyl ether (5 ml) was added and the precipitate was filtered off. The organic phase was washed with two portions of brine (5 ml) and dried (MgSO$_4$). Removing the solvent by evaporation gave 0.37 gram of methyl 2-{[4-(3-{4-[(methylsulfonyl)oxy]phenoxy}propyl)phenoxy]methyl}benzoate (yield 97.3%).

$^1$HNMR (500 MHz, CDCl$_3$): δ 2.1 (m, 2H), 2.75 (t, 2H), 3.15 (s, 3H), 3.9 (m, 5H), 5.5 (s, 2H), 6.9-7.0 (bm, 4H), 7.15 (d, 2H), 7.22 (d, 2H), 7.4 (t, 1H), 7.55 (t, 1H), 7.8 (d, 1H), 8.05 (d, 1H).

e) Methyl 2-{[4-(3-{4-[(methylsulfonyl)oxy]phenoxy}propyl)phenoxy]methyl}benzoate (0.38 g, 0.81 mmol) was dissolved in a mixture of THF/water (7/1, 4 ml) and lithium hydroxide (9.3 mg, 0.39 mmol) was added. The reaction was performed in a single node microwave oven (7 min, 150° C.). The reaction mixture was acidified (HCl, 1 M, 1 ml) and the water phase was washed with two portions of EtOAc (2×5 ml). The organic phases were combined, dried (MgSO$_4$) and the solvent was removed by evaporation the crude was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min)). The product containing fractions was pooled and the acetonitrile was removed by evaporation. EtOAc (10 ml) was added and the organic phase was washed with two portions of brine and dried (MgSO$_4$). Removing the solvent by evaporation gave 63 mg of 2-({4-[3-(4-hydroxyphenoxy)propyl]phenoxy}methyl)benzoic acid (yield 20.5%).

¹HNMR (500 MHz, CDCl₃): δ 2.05 (m, 2H), 2.75 (t, 2H), 3.9 (t, 2H), 5.58 (s, 2H), 6.65-6.8 (bm, 4H), 6.95 (d, 2H), 7.15 (d, 2H), 7.4 (t, 1H), 7.65 (t, 1H), 7.85 (d, 1H), 8.2 (d, 1H).

Example 21 a) 2-(2-Ethoxyphenyl)ethanamine (0.55 g, 3.33 mmol) and 3-(4-hydroxyphenyl)propanoic acid (0.50 g, 3.00 mmol) was dissolved in dimethyl formamide (5 ml) and cooled to 0° C. N-[(1H-1,2,3-benzotriazol-1-yloxy)(dimethylamino)methylene]-N-methylmethanaminium tetrafluoroborate (1.18 g, 3.66 mmol) and diisopropylethylamine (0.90 g, 7.0 mmol) were added and the solution was warmed to room temperature and stirred overnight. EtOAc (15 ml) was added and the organic phase was washed with two portions of sodium hydrogencarbonate (aq, 10 ml). The organic phase was dried (MgSO₄) and EtOAc was removed by evaporation to give 0.98 gram of N-[2-(2-ethoxyphenyl)ethyl]-3-(4-hydroxyphenyl)propanamide (yield 93.9%).

¹HNMR (Rotamers, 500 MHz, CDCl₃): δ 1.42 (t, 3H), 2.42 (t, 2H), 2.8-2.92 (m, 4H), 3.55 (q, 2H), 4.05 (q, 2H), 6.08 (m, 1H), 6.82-6.93 (m, 4H), 6.96-7.1 (m, 3H), 7.22 (t, 1H).

b) N-[2-(2-ethoxyphenyl)ethyl]-3-(4-hydroxyphenyl)propanamide (0.35 g, 1.12 mmol) and methyl 2-(bromomethyl)benzoate (0.28 g, 1.23 mmol) was dissolved in acetonitrile (5 ml) and potassium carbonate (324 mg, 2.34 mmol) was added. The mixture was stirred at 60° C. for three hours. Polymer supported trisamine (0.3 eqv) was added and stirred overnight. The polymer was filtered off, solvent was removed by evaporation, addition of EtOAc (10 ml) and the organic phase was washed with three portions of water. After drying the crude (MgSO₄) and the solvent was removed by evaporation, the crude was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min)). The product containing fractions were pooled and the acetonitrile was removed by evaporation. EtOAc (10 ml) was added and the organic phase was washed with two portions of brine and dried (MgSO₄). Removing the solvent by evaporation gave 26 mg of methyl 2-{[4-(3-{[2-(2-ethoxyphenyl)ethyl]amino}-3-oxopropyl)phenoxy]methyl}benzoate (yield 50.4%).

¹HNMR (Rotamers, 500 MHz, CDCl₃): δ 1.38 (t, 3H), 2.35 (t, 2H), 2.76 (t, 2H), 2.85 (t, 2H), 3.45 (q, 2H), 3.86 (s, 3H), 3.99 (q, 2H), 5.44 (s, 2H), 5.84 (m, 1H), 6.78-6.9 (m, 4H), 6.96-7.03 (m, 3H), 7.15 (t, 1H), 7.32 (t, 1H), 7.5 (t, 1H), 7.72 (d, 1H), 8.0 (d, 1H).

c) Methyl 2-{[4-(3-{[2-(2-ethoxyphenyl)ethyl]amino}-3-oxopropyl)phenoxy]methyl}-benzoate (0.26 g, 0.56 mmol) was dissolved in a mixture of THF/water (7/1, 5 ml) and lithium hydroxide (54 mg, 2.25 mmol) was added. The reaction was performed in a single node microwave oven (7 min, 150° C.). The reaction mixture was acidified (HCl, 1 M, 1 ml) and the water phase was washed with two portions of EtOAc (2×5 ml). The organic phases were combined, dried (MgSO₄) and the solvent was removed by evaporation. The crude product was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min)). The product containing fractions were pooled and the acetonitrile was removed by evaporation. EtOAc (10 ml) was added and the organic phase was washed with two portions of brine and dried (MgSO₄). Removing the solvent by evaporation gave 136 mg of 2-{[4-(3-{[2-(2-ethoxyphenyl)ethyl]amino}-3-oxopropyl)phenoxy]methyl}benzoic acid (yield 53.9%).

¹HNMR (Rotamers, 500 MHz, CDCl₃): δ 1.42 (t, 3H), 2.38 (t, 2H), 2.8 (t, 2H), 2.9 (t, 2H), 3.42 (q, 2H), 3.99 (q, 2H), 5.55 (s, 2H), 6.81-6.95 (m, 4H), 7.05-7.17 (m, 4H), 7.38 (t, 1H), 7.55 (m, 1H), 7.81 (d, 1H), 8.11 (d, 1H)

Example 22 a) N-Ethyl-N-(2-pyridin-2-ylethyl)amine (0.5 g, 3.32 mmol) and 3-(4-hydroxyphenyl)-propanoic acid (0.50 g, 3.00 mmol) was dissolved in dimethylformamide (5 ml) and cooled to 0° C. N-[(1H-1,2,3-benzotriazol-1-yloxy)(dimethylamino)methylene]-N-methylmethanaminium tetrafluoroborate (1.18 g, 3.66 mmol) and diisopropylethylamine (0.90 g, 7.0 mmol) were added and the solution was warmed to room temperature and stirred overnight. EtOAc (15 ml) was added and the organic phase was washed with two portions of sodium hydrogencarbonate (aq, 10 ml). The organic phase was dried MgSO₄) and EtOAc was removed by evaporation to give 0.913 gram of N-ethyl-3-(4 hydroxyphenyl)-N-(2-pyridin-2-ylethyl)propanamide (yield 91.9%).

¹HNMR (Rotamers, 500 MHz, CDCl₃): δ 0.97, 1.05 (t, t, 3H), 2.41, 2.52 (t, t, 2H), 2.75-3.0 (m, 4H), 3.09, 3.33 (q, q, 2H), 3.54, 3.61 (t, t, 2H), 6.74-6.82 (m, 2H), 6.93-7.2 (m, 4H), 7.58 (m, 1H), 8.48 (m, 1H).

b) N-Ethyl-3-(4-hydroxyphenyl)-N-(2-pyridin-2-ylethyl)propanamide (0.35 g, 1.17 mmol) and methyl 2-(bromomethyl)benzoate (0.30 g, 1.29 mmol) were dissolved in acetonitrile (5 ml) and potassium carbonate (324 mg, 2.34 mmol) was added. The mixture was stirred at 60° C. for three hours. Polymer supported trisamine (0.3 eqv) was added and stirred overnight. The polymer was filtered off, solvent was removed by evaporation, EtOAc (10 ml) was added and the organic phase was washed with three portions of water. After drying the organic layer (MgSO₄), the solvent was removed by evaporation. The crude was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min)). The product containing fractions were pooled and the acetonitrile was removed by evaporation EtOAc (10 ml) was added and the organic phase was washed with two portions of brine and dried (MgSO₄). Removing the solvent by evaporation gave 135 mg of methyl 2-[(4-{3-[ethyl(2-pyridin-2-ylethyl)amino]-3-oxopropyl}phenoxy)methyl]benzoate (yield 25.8%).

¹HNMR (Rotamers, 600 MHz, CDCl₃): δ 0.97, 1.05 (t, t, 3H), 2.41, 2.52 (t, t, 2H), 2.75-3.0 (m, 4H), 3.09, 3.33 (q, q, 2H), 3.54, 3.61 (t, t, 2H), 3.83 (s, 3H), 5.43 (s, 2H), 6.75-6.85 (m, 2H), 6.93-7.2 (m, 4H), 7.3 (t, 1H), 5.42 (m, 2H), 7.7 (d, 1H), 7.97 (d, 1H), 8.48 (m, 1H).

c) Methyl 2-[(4-{3-[ethyl(2-pyridin-2-ylethyl)amino]-3-oxopropyl}phenoxy)methyl]-benzoate (0.135 g, 0.30 mmol) was dissolved in a mixture of THF/water (7/1, 5 ml) and lithium hydroxide (29 mg, 1.2 mmol) was added. The reaction was performed in a single node microwave oven (7 min, 150° C.). The reaction mixture was acidified (HCl, 1 M, 1 ml) and the water phase was washed with two portions of EtOAc (2×5 ml). The organic phases were combined, dried (MgSO₄) and the solvent was removed by evaporation. The crude product was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min)). The product containing fractions were pooled and the acetonitrile was removed by evaporation. EtOAc (10 ml) was added and the organic phase was washed with two portions of brine and dried (MgSO$_4$). Removing the solvent by evaporation gave 27 mg of 2-[(4-{3-[ethyl(2-pyridin-2-ylethyl)amino]-3-oxopropyl}phenoxy)methyl]benzoic acid (yield 20.6%).

$^1$HNMR (Rotamers, 500 MHz, CDCl$_3$): δ 1.02, 1.12 (t, t, 3H), 2.48, 2.59 (t, t, 2H), 2.85-3.43 (m, 6H), 3.58, 3.66 (t, t, 2H), 5.51, 5.53 (s, s, 2H), 6.86-6.96 (m, 2H), 7.06-7.33 (m, 4H), 7.4 (t, 1H), 5.56 (t, 1H), 7.64-7.75 (m, 2H), 8.14 (m, 1H), 8.64 (m, 1H)

Example 23 a) 1-(2-Bromoethyl)-3-tert-butoxybenzene 3-(2-Bromoethyl)phenol (1.349 g, 6.709 mmol) in DCM (7 ml) was cooled under argon to −78° C. Under stirring, isobutene was bubbled into the mixture until more than 5 ml were added. Trifluoromethanesulphonic acid (50 μl) was dropped in. The mixture was stirred under argon at −78° C. for 4.5 hours. Triethylamine (120 μl) was added. The reaction mixture was allowed up to room temperature and then filtered. The filtrate was evaporated to dryness and petroleum ether (25 ml) was added into the residue. It was then filtered and evaporated. The obtained oil was solved in ethyl acetate, washed with water, dried (sodium sulphate) and evaporated. The residue was dissolved in CDCl$_3$ and then evaporated. 1.223 g desired product was left, yield 71%.

$^1$H NMR (500 MHz, CDCl$_3$): δ 1.42 (s, 9H), 3.17 (t, 2H), 3.59 (t, 2H), 6.92-6.98 (m, 3H) and 7.25 (t, 1H).

b) Methyl 2-{[2-(3-tert-butoxyphenyl)ethyl]thio}benzoate 1-(2-Bromoethyl)-3-tert-butoxybenzene (320 mg, 1.244 mmol) was dissolved in acetonitrile (15 ml). Methyl thiosalicylate (209 mg, 1.244 mmol) was added and then potassium carbonate, anhydrous (258 mg, 1.866 mmol) was added. The mixture was heated to reflux for 3 hours and then evaporated under vacuum to dryness. Chromatography of the residue on a column (ISOLUTE® SI, 5 g/25 ml) using ethyl acetate/heptane (5:95) as eluant gave 421 mg desired product, yield 98%.

$^1$H NMR (500 MHz, CDCl$_3$): δ 1.39 (s, 9H), 3.00 (t, 2H), 3.21 (t, 2H), 3.96 (s, 3H), 6.90-6.93 (m, 2H), 7.01 (d, 1H), 7.19-7.26 (m, 2H), 7.38 (d, 1H), 7.48 (t, 1H) and 8.00 (d, 1H).

c) Methyl 2-{[2-(3-hydroxyphenyl)ethyl]thio}benzoate

Methyl 2-{[2-(3-tert-butoxyphenyl)ethyl]thio}benzoate (402 mg, 1.167 mmol) was dissolved in DCM (3 ml). Trifluoroacetic acid (3 ml) was added. The mixture was stirred overnight and then evaporated to dryness. Chromatography of the residue on a column (ISOLUTE® SI, 2 g/6 ml) using ethyl acetate/heptane (2.5:97.5, then 5:95, then 10:90 and then 25:75) as eluant gave 260 mg the desired product, yield 77%. $^1$H NMR (500 MHz, CDCl$_3$): δ 2.94 (t, 2H), 3.17 (t, 2H), 3.95 (s, 3H), 6.18 (s, 1H) 6.77-6.83 (m, 3H), 7.18 (t, 2H), 7.34 (d, 1H), 7.44 (t, 1H) and 7.99 (d, 1H).

d) N-benzyl-2-bromo-N-hexylacetamide

N-hexylbenzylamine (4.2 g, 21.953 mmol) and triethylamine (3.98 ml, 28.539 mmol) were mixed in DCM (20 ml) and cooled in an ice-bath. Bromacetyl chloride (3.455 mg, 21.953 mmol) in DCM (5 ml) was added. The mixture was stirred over weekend and the temperature was allowed going up to room temperature. The mixture was washed with water mixed with 1% hydrochloric acid (water phase pH~4-5) and brine, dried with magnesium sulphate, and evaporated. Column chromatography of the residue on silica gel using ethyl acetate/heptane (10:90, then 20:80) as eluant gave 4.0 g desired product, yield 58%.

$^1$H NMR (rotamers, 300 MHz, CDCl$_3$): δ 0.85-0.92 (m, 3H), 1.28 (s, br, 6H), 1.53-1.62 (m, 2H), 3.25, 3.39 (t, t, 2H), 4.05, 4.16 (s, s, 2H), 4.61, 4.63 (s, s, 2H) and 7.19-7.42 (m, 5H).

e) Methyl 2-{[2-(3-{2-[benzyl(hexyl)amino]-2-oxoethoxy}phenyl)ethyl]thio}benzoate Methyl 2-{[2-(3-hydroxyphenyl)ethyl]thio}benzoate (129 mg, 0.447 mmol), N-benzyl-2-bromo-N-hexylacetamide (154 mg, 0.492 mmol) and potassium carbonate, anhydrous (93 mg, 0.671 mmol) were mixed in acetonitrile (10 ml). The mixture was heated to reflux overnight and then evaporated to dryness. Water and ethyl acetate were added into the residue. The two phases were separated. The organic phase was washed with brine and dried with magnesium sulphate and then evaporated. Chromatography of the residue on a column (ISOLUTE® SI, 2 g/6 ml) using ethyl acetate/heptane (10:90, then 25:75) as eluant gave 208 mg the desired product, yield 89.5%.

$^1$H NMR (rotamers, 500 MHz, CDCl$_3$): δ 0.86-0.91 (m, 3H), 1.24-1.32 (m, 6H), 1.53-1.64 (m, 2H), 2.94-3.03 (m, 2H), 3.13-3.20 (m, 2H), 3.29, 3.41 (t, t, 2H), 3.93 (s, 3H), 4.64, 4.65 (s, s, 2H), 4.71, 4.81 (s, s, 2H), 6.75-6.77 (m, 1H), 6.85-6.93 (m, 2H), 7.17-7.39 (m, 8H), 7.46 (t, 1H) and 7.99 (d, 1H).

$^{13}$C NMR (rotamers, 125 MHz, CDCl$_3$): δ 13.85, 13.86, 22.39, 26.38, 27.03, 28.27, 31.31, 31.37, 33.28, 34.51, 34.57, 46.34, 48.13, 50.33, 51.94, 67.13, 67.38, 112.33, 112.39, 114.84, 114.96, 121.48, 121.56, 123.79, 125.49, 126.40, 127.24, 127.54, 127.64, 127.89, 128.42, 128.74, 129.48, 129.57, 131.17, 132.22, 136.51, 137.03, 141.30, 141.74, 141.87, 158.06, 158.15, 166.75, 167.74 and 167.88.

f) 2-{[2-(3-{2-[Benzyl(hexyl)amino]-2-oxoethoxy}phenyl)ethyl]thio}benzoic acid

Methyl 2-{[2-(3-{2-[benzyl(hexyl)amino]-2-oxoethoxy}phenyl)ethyl]thio}benzoate (80 mg, 0.154 mmol) in tetrahydrofuran (3 ml) was cooled in an ice-bath. Lithium hydroxide (7.4 mg, 0.308 mmol) in water (3 ml) was added. The cooling bath was then removed and the mixture was stirred for 12 days and then evaporated in vacuum to remove tetrahydrofuran. The residue was acidified with 1% hydrochloric acid, pH=3, and extracted with ethyl acetate. The organic phase was dried with magnesium sulphate and evaporated. Chromatography of the residue on a column (ISOLUTE® SI, 2 g/6 ml) using DCM, MeOH/DCM (1:99, and then 2:98) as eluant gave 27 mg product mixture. Re-chromatography of the mixture on a column (ISOLUTE® SI, 1 g/6 ml) using DCM and then MeOH/AcOH/DCM (0.25:0.25:99.5) as eluant gave 17 mg desired product, yield 22%.

$^1$H NMR (rotamers, 500 MHz, CDCl$_3$): δ 0.85-0.90 (m, 3H), 1.23-1.31 (m, 6H), 1.53-1.63 (m, 2H), 2.91-3.00 (m, 2H), 3.11-3.20 (m, 2H), 3.29, 3.41 (t, t, 2H), 4.65, 4.66 (s, s, 2H), 4.74, 4.83 (s, s, 2H), 6.72-6.93 (m, 3H), 7.20-7.32 (m, 6H), 7.37 (t, 2H), 7.47 (t, 1H) and 8.09 (d, 1H).

$^{13}$C NMR (rotamers, 125 MHz, CDCl$_3$): δ 13.98, 22.51, 26.51, 27.11, 28.36, 31.42, 31.49, 34.16, 34.60, 34.66, 46.52, 48.35, 50.52, 67.20, 67.47, 112.60, 115.15, 115.29, 121.66, 121.75, 124.46, 126.54, 126.80, 127.42, 127.70, 128.04, 128.56, 128.89, 129.59, 129.67, 132.13, 132.79, 136.46, 136.98, 141.16, 141.75, 141.89, 158.08, 158.17, 168.25, 168.37 and 169.60.

Example 24

AR-H072686 a) Heptan-1-amine (1 g, 8.679 mmol was dissolved in DMF (10 ml), (2-methoxyphenyl)acetic acid (1.587 g, 9.547 mmol) was added and the mixture was cooled to 0° C. N-[(1H-1,2,3-benzotriazol-1-yloxy)(dimethylamino)methylene]-N-methylmethanaminium tetrafluoroborate (3.065, 9.547 mmol) and N-ethyl-N,N-diisopropylamine (2.356 g, 18.226 mmol) were added. The solution was stirred overnight at room temperature. EtOAc (20 ml) was added and the organic phase was washed with two portions of NaHCO3 (2×20 ml, aq). The organic layer was dried (MgSO$_4$) and the solvent was removed by evaporation. The crude was purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation EtOAc (10 ml) was added and the organic phase was washed with two portions of brine and dried (MgSO$_4$) and the solvent was removed by evaporation to give 2.00 g of N-heptyl-2-(2-methoxyphenyl)acetamide (yield 87.5%).

$^1$HNMR (500 MHz, CDCl$_3$): δ 0.75 (t, 3H), 1.10 (m, 8H), 1.28 (m, 2H), 3.02 (q, 2H), 3.39 (s, 2H), 3.45 (s, 3H), 6.2 (bs, 1H), 6.75 (m, 2H), 7.08 (m, 2H).

b) N-Heptyl-2-(2-methoxyphenyl)acetamide (2.00 g, 7.594 mmol) was dissolved in THF (10 ml) and was cooled to zero degrees under argon atmosphere. (Methylthio)methane compound with borane (1:1) (1.442 g, 18.984 mmol) was added and the mixture was refluxed for 5 hours. After the mixture was cooled to room temperature, 5 ml HCl (10%) was gently added and the mixture was stirred overnight. The solvent was removed by evaporation. EtOAc (20 ml) was added and the organic phase was washed with K$_2$CO$_3$ (2M, 2×20 ml). The crude was purified by flash cromatography (started with isocratic heptane/EtOAc 50/50 and then the EtOAc concentration was increased to 100%, (silica gel 60 0.004-0.063 mm). The product containing fractions were pooled and the EtOAc was removed by evaporation to give 1.037 g of N-[2-(2-methoxyphenyl)ethyl]heptan-1-amine (yield 54.8%).

$^1$HNMR (300 MHz, CDCl$_3$): δ 0.83 (t, 3H), 1.07 (s, 1H), 1.13 (m, 8H), 1.43 (m, 2H), 2.57 (m, 2H), 2.80 (s, 4H), 3.72 (s, 3H), 6.8 (bm, 2H), 7.08 (m, 2H).

c) N-[2-(2-Methoxyphenyl)ethyl]heptan-1-amine (0.091 g, 0.366 mmol) was dissolved in DMF (5 ml), (4-{[2-(methoxycarbonyl)benzyl]oxy}phenyl)acetic acid (0.100 g, 0.333 mmol) was added and the mixture was cooled to 0° C. N-[(1H-1,2,3-Benzotriazol-1-yloxy)(dimethylamino)methylene]-N-methylmethanaminium tetrafluoroborate (0.118 g, 0.366 mmol) and N-ethyl-N,N-diisopropylamine (0.090 g, 0.699 mmol) were added. The solution was stirred overnight at room temperature. EtOAc (20 ml) was added and the organic phase was washed with two portions of water (2×20 ml). The organic layer was dried (MgSO$_4$) and the solvent was removed by evaporation. The crude was purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. EtOAc (10 ml) was added and the organic phase was washed with two portions of brine and dried (MgSO$_4$) and the solvent was removed by evaporation to give 0.094 g of methyl 2-{[4-(2-{heptyl[2-(2-methoxyphenyl)ethyl]amino}-2-oxoethyl)phenoxy]methyl}benzoate (yield 53.1%).

$^1$HNMR (Rotamers, 400 MHz, CDCl$_3$): δ 0.85 (t, 3H), 1.13 (m, 8H), 1.43 (m, 2H), 2.7-3.75 (m, 8H), 3.77-3.95 (bm, 6H), 5.5 (m, 2H), 6.8-7.45 (bm, 9H), 7.55 (q, 1H), 7.73 (q, 1H), 8.03 (3H).

d) Methyl 2-{[4-(2-{heptyl[2-(2-methoxyphenyl)ethyl]amino}-2-oxoethyl)phenoxy]methyl}benzoate (0.094 g, 0.177 mmol) was dissolved in EtOH (5 ml, 95%), potassium hydroxide (0.015 g, 0.265 mmol) was added. The reaction was performed in an single node microwave oven (7 min, 150 deg). Workup by removing the solvent by evaporation and addition of HCl (2 ml, 1 M). The waterphase was extracted with two portions of EtOAc (20 ml) and the organic phase was dried (MgSO$_4$) and the solvent was removed by evaporation. The crude was purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. EtOAc (10 ml) was added and the organic phase was washed with two portions of brine and dried (MgSO$_4$). The solvent was removed by evaporation to give 0.011 g of 2-{[4-(2-{heptyl[2-(2-methoxyphenyl)ethyl]amino}-2-oxoethyl)phenoxy]methyl}benzoic acid (yield 12%).

$^1$HNMR (Rotamers, 500 MHz, CDCl$_3$): δ 0.85 (t, 3H), 1.13 (m, 8H), 1.43 (m, 2H), 2.7-3.75 (m, 8H), 3.77-3.95 (bm, 3H), 5.5 (m, 2H), 6.8-7.45 (bm, 9H), 7.55 (q, 1H), 7.73 (q, 1H), 8.03 (3H).

Example 25

AR-H072687 a) Heptan-1-amine (1 g, 8.679 mmol) was dissolved in dry THF under N$_2$ and polymer supported N-benzyl-N,N-diisopropylamine (4.955 g, 26.038 mmol) was added. The mixture was stirred for 30 min and cooled to 0 degrees and (4-chlorophenyl)acetyl chloride (1.969 g, 10.415 mmol) was added. The solution was stirred overnight at room temperature. The excess of (4-chlorophenyl)acetyl chloride was removed by filtering the mixture through an NH$_2$ cartridge. The solvent was removed by evaporation. The crude was purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation EtOAc (10 ml) was added and the organic phase was washed with two portions of brine and dried (MgSO$_4$) and the solvent was removed by evaporation to give 1.045 g of 2-(4-chlorophenyl)-N-heptylacetamide (yield 45.0%).

$^1$HNMR (500 MHz, CDCl$_3$): δ 0.82 (t, 3H), 1.2 (m, 8H), 1.39 (m, 2H), 3.12 (t, 2H), 3.43 (s, 2H), 6.35 (bs, 1H), 7.15 (d, 2H), 7.23 (d, 2H).

b) 2-(4-Chlorophenyl)-N-heptylacetamide (0.886 g, 3.797 mmol) was dissolved in THF (10 ml) and was cooled to zero degrees under argon atmosphere. (Methylthio)methane compound with borane (1:1) (0.741 g, 9.755 mmol) was added and the mixture was refluxed for 5 hours. After the mixture was cooled to room temperature, 5 ml HCl (10%) was gently added and the mixture was stirred overnight. The solvent was removed by evaporation. EtOAc (20 ml) was added and the organic phase was washed with $K_2CO_3$ (2M, 2×20 ml). The crude was purified by flash chromatography (started with isocratic heptane/EtOAc 50/50 and then the EtOAc concentration was increased to 100%, (silica gel 60 0.004-0.063 mm). The product containing fractions were pooled and the EtOAc was removed by evaporation to give 0.609 g of N-[2-(4-chlorophenyl)ethyl]-N-heptylamine (yield 61.5%).

$^1$HNMR (300 MHz, $CDCl_3$): δ 0.85 (t, 3H), 1.22 (m, 8H), 1.39 (m, 2H), 2.52 (t, 2H), 2.45-2.6 (t, 2H), 2.6-2.82 (m, 4H), 7.0-7.2 (bm, 2H).

c) N-[2-(4-Chlorophenyl)ethyl]-N-heptylamine (0.093 g, 0.366 mmol) was dissolved in DMF (5 ml). (4-{[2-(Methoxycarbonyl)benzyl]oxy}phenyl)acetic acid (0.100 g, 0.333 mmol) was added and the mixture was cooled to 0° C. N-[(1H-1,2,3-Benzotriazol-1-yloxy)(dimethylamino)methylene]-N-methylmethanaminium tetrafluoroborate (0.118 g, 0.366 mmol) and N-ethyl-N,N-diisopropylamine (0.090 g, 0.699 mmol) were added. The solution was stirred overnight at room temperature. EtOAc (20 ml) was added and the organic phase was washed with two portions of water (2×20 ml). The organic layer was dried ($MgSO_4$) and the solvent was removed by evaporation. The crude was purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. EtOAc (10 ml) was added and the organic phase was washed with two portions of brine and dried ($MgSO_4$) and the solvent was removed by evaporation to give 0.112 g of methyl 2-[(4-{2-[[2-(4-chlorophenyl)ethyl](heptyl)amino]-2-oxoethyl}phenoxy)methyl]benzoate (yield 62.7%).

$^1$HNMR (Rotamers, 300 MHz, $CDCl_3$): δ 0.85 (t, 3H), 1.22 (m, 8H), 1.39 (m, 2H), 2.62-3.7 (bm, 8H), 3.9 (m, 3H), 5.45-5.55 (m, 2H), 6.89-7.43 (bm, 9H), 7.52 (m, 1H), 7.75 (t, 1H), 8.02 (t, 1H).

d) Methyl 2-[(4-{2-[[2-(4-chlorophenyl)ethyl](heptyl)amino]-2-oxoethyl}phenoxy)methyl]benzoate (0.112 g, 0.209 mmol) was dissolved in EtOH (5 ml, 95%) and potassium hydroxide (0.018 g, 0.313 mmol) was added. The reaction was performed in an single node microwave oven (7 min, 150 deg). Workup was by removing the solvent by evaporation and addition of HCl (2 ml, 1 M). The water-phase was extracted with two portions of EtOAc (20 ml) and the organic phase was dried ($MgSO_4$) and the solvent was removed by evaporation. The crude was purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation EtOAc (10 ml) was added and the organic phase was washed with two portions of brine and dried ($MgSO_4$). The solvent was removed by evaporation to give 0.006 g of 2-[(4-{2-[[2-(4-chlorophenyl)ethyl](heptyl)amino]-2-oxoethyl}phenoxy)methyl]benzoic acid (yield 5.5%). $^1$HNMR (Rotamers, 300 MHz, $CDCl_3$): δ 0.85 (t, 3H), 1.22 (m, 8H), 1.39 (m, 2H), 2.62-3.7 (bm, 8H), 5.45-5.55 (m, 2H), 6.89-7.43 (bm, 9H), 7.52 (m, 1H), 7.78 (t, 1H), 8.13 (t, 1H).

Example 26

AR-H072688 a) Heptan-1-amine (1 g, 8.679 mmol) was dissolved in dry THF under $N_2$ and polymer supported N-benzyl-N,N-diisopropylamine (4.955 g, 26.038 mmol) was added. The mixture was stirred for 30 min and cooled to 0 degrees and phenylacetyl chloride (1.610 g, 10.415 mmol) was added. The solution was stirred overnight at room temperature. The excess of phenylacetyl chloride was removed by filtering the mixture through an $NH_2$ cartridge. The solvent was removed by evaporation. The crude was purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. EtOAc (10 ml) was added and the organic phase was washed with two portions of brine and dried ($MgSO_4$) and the solvent was removed by evaporation to give 0.886 g of N-heptyl-2-phenylacetamide (yield 43.7%).

$^1$HNMR (500 MHz, $CDCl_3$): δ 0.82 (t, 3H), 1.22 (m, 8H), 1.39 (m, 2H), 3.12 (t, 2H), 3.45 (s, 2H), 6.45 (bs, 1H), 7.18-7.3 (bm, 5H).

b) N-Heptyl-2-phenylacetamide (0.886 g, 3.797 mmol) was dissolved in THF (10 ml) and was cooled to zero degrees under argon atmosphere. (Methylthio)methane compound with borane (1:1) (0.721 g, 9.492 mmol) was added and the mixture was refluxed for 5 hours. After the mixture was cooled to room temperature, 5 ml HCl (10%) was gently added and was stirred overnight. The solvent was removed by evaporation. EtOAc (20 ml) was added and the organic phase was washed with $K_2CO_3$ (2M, 2×20 ml). The crude was purified by flash chromatography (started with isocratic heptane/EtOAc 50/50 and then the EtOAc concentration was increased to 100%, (silica gel 60 0.004-0.063 mm). The product containing fractions were pooled and the EtOAc was removed by evaporation to give 0.584 g of N-(2-phenylethyl)heptan-1-amine (yield 70.1%).

$^1$HNMR (300 MHz, $CDCl_3$): δ 0.85 (t, 3H), 1.25 (m, 8H), 1.43 (m, 2H), 2.6 (t, 2H), 2.7-2.95 (bm, 4H), 7.1-7.35 (bm, 5H).

c) N-(2-Phenylethyl)heptan-1-amine (0.080 g, 0.366 mmol) was dissolved in DMF (5 ml), (4-{[2-(methoxycarbonyl)benzyl]oxy}phenyl)acetic acid (0.100 g, 0.333 mmol) was added and the mixture was cooled to 0° C. N-[(1H-1,2, 3-Benzotriazol-1-yloxy)(dimethylamino)methylene]-N-methylmethanaminium tetrafluoroborate (0.118 g, 0.366 mmol) and N-ethyl-N,N-diisopropylamine (0.090 g, 0.699 mmol) were added. The solution was stirred overnight at room temperature. EtOAc (20 ml) was added and the organic phase was washed with two portions of water (2×20 ml). The organic layer was dried ($MgSO_4$) and the solvent was removed by evaporation. The crude was purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. EtOAc (10 ml) was added and the organic phase was washed with two portions of brine and dried ($MgSO_4$) and the solvent was removed by evaporation to give 0.146 g of methyl 2-[(4-{2-[heptyl(2-phenylethyl)amino]-2-oxoethyl}phenoxy)methyl]-benzoate (yield 87.4%).

¹HNMR (Rotamers, 400 MHz, CDCl₃): δ 0.85 (t, 3H), 1.1-1.35 (bm, 8H), 1.4-1.6 (bm, 2H), 2.65-65 (m, 8H), 3.9 (m, 3H), 5.43-5.56 (m, 2H), 6.85-7.4 (bm, 10H), 7.52 (m, 1H), 7.73 (t, 1H), 8.02 (t, 1H).

d) Methyl 2-[(4-{2-[heptyl(2-phenylethyl)amino]-2-oxoethyl}phenoxy)methyl]benzoate (0.146 g, 0.291 mmol) was dissolved in EtOH (5 ml, 95%), potassium hydroxide (0.025 g, 0.437 mmol) was added. The reaction was performed in an single node microwave oven (7 min, 150° C.). Work-up was by removing the solvent by evaporation and addition of HCl (2 ml, 1 M). The water-phase was extracted with two portions of EtOAc (20 ml) and the organic phase was dried (MgSO₄) and the solvent was removed by evaporation. The crude was purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation EtOAc (10 ml) was added and the organic phase was washed with two portions of brine and dried (MgSO₄). The solvent was removed by evaporation to give 0.043 g of 2-[(4-{2-[heptyl(2-phenylethyl)amino]-2-oxoethyl}-phenoxy)methyl]benzoic acid (yield 30.3%).

¹HNMR (Rotamers, 500 MHz, CDCl₃): δ 0.85 (t, 3H), 1.1-1.35 (bm, 8H), 1.4-1.6 (bm, 2H), 2.65-65 (m, 8H), 5.43-5.56 (m, 2H), 6.9-7.45 (bm, 10H), 7.57 (m, 1H), 7.78 (t, 1H), 8.17 (t, 1H).

Example 27

AR-H075101 a) N-(2-Fluorobenzyl)ethanamine (0.248 g, 0.993) was dissolved in DMF (10 ml), (4-hydroxyphenoxy)acetic acid (0.150 g, 0.903 mmol) was added and the mixture was cooled to 0° C. N-[(1H-1,2,3-benzotriazol-1-yloxy)(dimethylamino)methylene]-N-methylmethanaminium tetrafluoroborate (0.319 g, 0.993 mmol) and N-ethyl-N,N-diisopropylamine (0.245 g, 1.896 mmol) were added. The solution was stirred overnight at room temperature. EtOAc (20 ml) was added and the organic phase was washed with two portions of Na₂CO3 (2×20 ml, aq). The organic layer was dried (MgSO₄) and the solvent was removed by evaporation. The crude was purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. EtOAc (10 ml) was added and the organic phase was washed with two portions of brine and dried (MgSO₄) and the solvent was removed by evaporation to give 0.177 g of N-ethyl-N-(2-fluorobenzyl)-2-(4-hydroxyphenoxy)acetamide (yield 64.6%).

¹HNMR (Rotamers, 300 MHz, CDCl₃): δ 1.02-1.25 (m, 3H), 3.4 (q, 2H), 4.68 (m, 4H), 6.65-6.85 (m, 4H), 6.95-7.4 (m, 4H).

b) N-Ethyl-N-(2-fluorobenzyl)-2-(4-hydroxyphenoxy)acetamide (0.177 g, 0.586 mmol) was dissolved in acetonitrile (10 ml), methyl 2-(bromomethyl)benzoate (0.147 g, 0.642 mmol) and dipotassium carbonate (0.161 g, 1.167 mmol) were added. The solution was stirred for 2 hours at 60° C. EtOAc (20 ml) was added and the organic phase was washed with two portions of brine (2×20 ml, aq). The organic layer was dried (MgSO₄) and the solvent was removed by evaporation. The crude was purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. EtOAc (10 ml) was added and the organic phase was washed with two portions of brine and dried (MgSO₄) and the solvent was removed by evaporation to give 0.242 g of methyl 2-[(4-{2-[ethyl(2-fluorobenzyl)amino]-2-oxoethoxy}phenoxy)methyl]benzoate (yield 91.9%).

¹HNMR (Rotamers, 300 MHz, CDCl₃): δ 1.02-1.28 (m, 3H), 3.39 (m, 2H), 3.89 (s, 3H) 4.6-4.75 (m, 4H), 5.42 (d, 2H), 6.75-7.42 (bm, 9H), 7.55 (t, 1H), 7.72 (t, 1H), 8.0 (d, 1H).

c) Methyl 2-[(4-{2-[ethyl(2-fluorobenzyl)amino]-2-oxoethoxy}phenoxy)methyl]-benzoate (0.242 g, 0.536 mmol) was dissolved in EtOH (5 ml, 95%), potassium hydroxide (0.060 g, 1.072 mmol) was added. The reaction was performed in an single node microwave oven (7 min, 150° C.). Work-up was by removing the solvent by evaporation and addition of HCl (2 ml, 1 M). The water-phase was extracted with two portions of EtOAc (20 ml) and the organic phase was dried (MgSO₄) and the solvent was removed by evaporation. The crude was purified by flash chromatography (started with isocratic DCM 100% and then the MeOH concentration was increased from 0.5% to 20%, (silica gel 60 0.004-0.063 mm). The product containing fractions were pooled and the EtOAc was removed by evaporation to give 0.160 g of 2-[(4-{2-[ethyl(2-fluorobenzyl)amino]-2-oxoethoxy}phenoxy)methyl]benzoic acid (yield 68.2%).

¹HNMR (Rotamers, 500 MHz, CDCl₃): δ 1.07-1.28 (m, 3H), 3.42 (m, 2H), 4.62-4.78 (m, 4H), 5.48 (d, 2H), 6.78-7.37 (bm, 8H), 7.40 (m, 1H), 7.60 (q, 1H), 7.80 (t, 1H), 8.18 (d, 1H).

Example 28

AR-H075104 a) N-(2-Fluorobenzyl)ethanamine (0.077 g, 0.500 mmol) was dissolved in DMF (10 ml), (4-{[2-(methoxycarbonyl)phenoxy]methyl}phenyl)acetic acid (0.150 g, 0.500 mmol) was added and the mixture was cooled to 0° C. N-[(1H-1,2,3-benzotriazol-1yloxy)(dimethylamino)methylene]-N-methylmethanaminium tetrafluoroborate (0.176 g, 0.549 mmol) and N-ethyl-N,N-diisopropylamine (0.136 g, 1.049 mmol) was added. The solution was stirred overnight at room temperature. EtOAc (20 ml) was added and the organic phase was washed with two portions of Na₂CO₃ (2×20 ml, aq). The organic layer was dried (MgSO₄) and the solvent was removed by evaporation. The crude was purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. EtOAc (10 ml) was added and the organic phase was washed with two portions of brine and dried (MgSO₄) and the solvent was removed by evaporation to give 0.146 g of methyl 2-[(4-{2-[ethyl(2-fluorobenzyl)amino]-2-oxoethyl}benzyl)oxy]benzoate (yield 67.1%).

¹HNMR (Rotamers, 400 MHz, CDCl₃): δ 1.02-1.15 (m, 3H), 3.25-3.5 (m, 2H), 3.65-3.8 (m, 2H), 3.88 (s, 3H), 4.5-4.7 (bm, 2H), 5.17 (m, 2H), 6.92-7.5 (bm, 11H), 7.8 (m, 2H).

b) Methyl 2-[(4-{2-[ethyl(2-fluorobenzyl)amino]-2-oxoethyl}benzyl)oxy]benzoate (0.242 g, 0.555 mmol) was dissolved in EtOH (5 ml, 95%), potassium hydroxide (0.062 g, 1.111 mmol) was added. The reaction was performed in an single node microwave oven (7 min, 150° C.). Work-up by removing the solvent by evaporation and addition of HCl (2 ml, 1 M). The water-phase was extracted with two portions of EtOAc (20 ml) and the organic phase was dried (MgSO$_4$) and the solvent was removed by evaporation. The crude was purified by flash chromatography (started with isocratic DCM 100% and then the MeOH concentration was increased from 0.5% to 20%, (silica gel 60 0.004-0.063 mm). The product containing fractions were pooled and the EtOAc was removed by evaporation to give 0.013 g of 2-[(4-{2-[ethyl(2-fluorobenzyl)amino]-2-oxoethyl}benzyl)oxy]benzoic acid (yield 5.6%).

$^1$HNMR (Rotamers, 400 MHz, CDCl$_3$): δ 1.1 (t, 3H), 3.3-3.5 (bm, 2H), 3.7-3.82 (m, 2H), 4.55-4.7 (bm, 2H), 5.23 (d, 2H), 6.95-7.45 (bm, 11H), 7.55 (t, 3H), 8.22 (d, 1H).

Example 29

AR-H075106 a) Heptan-1-amine (1 g, 8.679 mmol) was dissolved in dry THF under N2 and polymer supported N-benzyl-N,N-diisopropylamine (4.955 g, 26.038 mmol) was added. The mixture was stirred for 30 min and cooled to 0° C. and phenylacetyl chloride (1.610 g, 10.415 mmol) was added. The solution was stirred overnight at room temperature. The excess of phenylacetyl chloride was removed by filtering the mixture through an NH$_2$ cartridge. The solvent was removed by evaporation. The crude was purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. EtOAc (10 ml) was added and the organic phase was washed with two portions of brine and dried (MgSO$_4$) and the solvent was removed by evaporation to give 0.886 g of N-heptyl-2-phenylacetamide (yield 43.7%).

$^1$HNMR (500 MHz, CDCl$_3$): δ 0.82 (t, 3H), 1.22 (m, 8H), 1.39 (m, 2H), 3.12 (t, 2H), 3.45 (s, 2H), 6.45 (bs, 1H), 7.18-7.3 (bm, 5H).

b) N-Heptyl-2-phenylacetamide (0.886 g, 3.797 mmol) was dissolved in THF (10 ml) and was cooled to 0° C. under argon atmosphere. (Methylthio)methane compound with borane (1:1) (0.721 g, 9.492 mmol) was added and the mixture was refluxed for 5 hours. After the mixture was cooled to room temperature, 5 ml HCl (10%) was gently added and the mixture was stirred overnight. The solvent was removed by evaporation. EtOAc (20 ml) was added and the organic phase was washed with K$_2$CO$_3$ (2M, 2×20 ml). The crude was purified by flash chromatography (started with isocratic heptane/EtOAc 50/50 and then the EtOAc concentration was increased to 100%, (silica gel 60 0.004-0.063 mm). The product containing fractions were pooled and the EtOAc was removed by evaporation to give 0.584 g of N-(2-phenylethyl)heptan-1-amine (yield 70.1%).

$^1$HNMR (300 MHz, CDCl$_3$): δ 0.85 (t, 3H), 1.25 (m, 8H), 1.43 (m, 2H), 2.6 (t, 2H), 2.7-2.95 (bm, 4H), 7.1-7.35 (bm, 5H).

c) N-(2-Phenylethyl)heptan-1-amine (0.110 g, 0.500 mmol) was dissolved in DMF (10 ml), (4-{[2-(methoxycarbonyl)phenoxy]methyl}phenyl)acetic acid (0.150 g, 0.500 mmol) was added and the mixture was cooled to 0° C. N-[(1H-1,2,3-benzotriazol-1-yloxy)(dimethylamino)methylene]-N-methylmethanaminium tetrafluoroborate (0.176 g, 0.549 mmol) and N-ethyl-N,N-diisopropylamine (0.136 g, 1.049 mmol) were added. The solution was stirred overnight at room temperature. EtOAc (20 ml) was added and the organic phase was washed with two portions of Na$_2$CO$_3$ (2×20 ml, aq). The organic layer was dried (MgSO$_4$) and the solvent was removed by evaporation. The crude was purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation EtOAc (10 ml) was added and the organic phase was washed with two portions of brine and dried (MgSO$_4$) and the solvent was removed by evaporation to give 0.229 g of methyl 2-[(4-{2-[heptyl(2-phenylethyl)amino]-2-oxoethyl}benzyl)oxy]benzoate (yield 91.4%).

$^1$HNMR (Rotamers, 400 MHz, CDCl$_3$): δ 0.85 (m, 3H), 1.25 (m, 8H), 1.40-1.6 (m, 2H), 2.75-3.7 (bm, 8H), 3.9 (m, 3H), 5.17 (d, 2H), 6.96-7.5 (bm, 12H), 7.8 (t, 1H).

d) Methyl 2-[(4-{2-[heptyl(2-phenylethyl)amino]-2-oxoethyl}benzyl)oxy]benzoate (0.229 g, 0.457 mmol) was dissolved in EtOH (5 ml, 95%) and potassium hydroxide (0.051 g, 0.913 mmol) was added. The reaction was performed in an single node microwave oven (7 min, 150° C.). Work-up was by removing the solvent by evaporation and addition of HCl (2 ml, 1 M). The water-phase was extracted with two portions of EtOAc (20 ml) and the organic phase was dried (MgSO$_4$) and the solvent was removed by evaporation. The crude was purified by flash chromatography (started with isocratic DCM 100% and then the MeOH concentration was increased from 0.5% to 20%, (silica gel 60 0.004-0.063 mm). The product containing fractions were pooled and the EtOAc was removed by evaporation. The product was not pure and was therefore purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. EtOAc (10 ml) was added and the organic phase was washed with two portions of brine and dried (MgSO$_4$). The solvent was removed by evaporation to give 0.025 g of 2-[(4-{2-[heptyl(2-phenylethyl)amino]-2-oxoethyl}benzyl)oxy]benzoic acid (yield 11.2%).

$^1$HNMR (Rotamers, 400 MHz, CDCl$_3$): δ 0.85 (m, 3H), 1.25 (m, 8H), 1.40-1.62 (m, 2H), 2.75-3.7 (bm, 8H), 5.23 (d, 2H), 7.05-7.6 (bm, 12H), 8.2 (t, 1H).

Example 30

AR-H075107 a) Heptan-1-amine (1 g, 8.679 mmol) was dissolved in dry THF under N$_2$ and polymer supported N-benzyl-N,N-diisopropylamine (4.955 g, 26.038 mmol) was added. The mixture was stirred for 30 min and cooled to 0° C. and (4-chlorophenyl)acetyl chloride (1.969 g, 10.415 mmol) was added. The solution was stirred overnight at room temperature. The excess of (4-chlorophenyl)acetyl chloride was removed by filtering the mixture through an NH$_2$ cartridge. The solvent was removed by evaporation. The crude was purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. EtOAc (10 ml) was added and the organic phase was washed with two portions of brine and dried (MgSO$_4$) and the solvent was removed by evaporation to give 1.045 g of 2-(4-chlorophenyl)-N-heptylacetamide (yield 45.0%).

$^1$HNMR (500 MHz, CDCl$_3$): δ 0.82 (t, 3H), 1.22 (m, 8H), 1.35 (m, 2H), 3.12 (q, 2H), 3.40 (s, 2H), 6.35 (bs, 1H), 7.1-7.3 (bm, 4H).

b) 2-(4-Chlorophenyl)-N-heptylacetamide (1.045 g, 3.902 mmol) was dissolved in THF (10 ml) and was cooled to 0° C. under argon atmosphere. (Methylthio)methane compound with borane (1:1) (0.741 g, 9.756 mmol) was added and the mixture was refluxed for 5 hours. After the mixture was cooled to room temperature, 5 ml HCl (10%) was gently added and was stirred overnight. The solvent was removed by evaporation. EtOAc (20 ml) was added and the organic phase was washed with K$_2$CO$_3$ (2M, 2×20 ml). The crude was purified by flashchromatography (started with isocratic heptane/EtOAc 50/50 and then the EtOAc concentration was increased to 100%, (silica gel 60 0.004-0.063 mm). The product containing fractions was pooled and the EtOAc was removed by evaporation to give 0.609 g of N-[2-(4-chlorophenyl)ethyl]-N-heptylamine (yield 61.5%).

$^1$HNMR (300 MHz, CDCl$_3$): δ 0.82 (t, 3H), 1.22 (m, 8H), 1.38 (m, 2H), 2.52 (t, 2H), 2.6-2.85 (bm, 4H), 7.0-7.3 (bm, 4H).

c) N-[2-(4-Chlorophenyl)ethyl]-N-heptylamine (0.127 g, 0.500 mmol) was dissolved in DMF (10 ml), (4-{[2-(methoxycarbonyl)phenoxy]methyl}phenyl)acetic acid (0.150 g, 0.500 mmol) was added and the mixture was cooled to 0° C. N-[(1H-1,2,3-benzotriazol-1-yloxy)(dimethylamino)methylene]-N-methylmethanaminium tetrafluoroborate (0.176 g, 0.549 mmol) and N-ethyl-N,N-diisopropylamine (0.136 g, 1.049 mmol) was added. The solution was stirred overnight at room temperature. EtOAc (20 ml) was added and the organic phase was washed with two portions of Na$_2$CO3 (2×20 ml, aq). The organic layer was dried (MgSO$_4$) and the solvent was removed by evaporation. The crude was purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions was pooled and the acetonitrile was removed by evaporation EtOAc (10 ml) was added and the organic phase was washed with two portions of brine and dried (MgSO$_4$) and the solvent was removed by evaporation to give 0.224 g of methyl 2-[(4-{2-[[2-(4-chlorophenyl)ethyl](heptyl)-amino]-2-oxoethyl}benzyl)oxy]benzoate (yield 83.7%).

$^1$HNMR (Rotamers, 400 MHz, CDCl$_3$): δ 0.85 (m, 3H), 1.25 (m, 8H), 1.40-1.6 (m, 2H), 2.7-3.75 (bm, 8H), 3.9 (m, 3H), 5.17 (d, 2H), 6.96-7.5 (bm, 11H), 7.8 (t, 1H).

d) Methyl 2-[(4-{2-[[2-(4-chlorophenyl)ethyl](heptyl)amino]-2-oxoethyl}benzyl)oxy]-benzoate (0.224 g, 0.418 mmol) was dissolved in EtOH (5 ml, 95%) and potassium hydroxide (0.047 g, 0.836 mmol) was added. The reaction was performed in an single node microwave oven (7 min, 150° C.). Work-up was by removing the solvent by evaporation and addition of HCl (2 ml, 1 M). The water-phase was extracted with two portions of EtOAc (20 ml) and the organic phase was dried (MgSO$_4$) and the solvent was removed by evaporation. The crude was purified by flash chromatography (started with isocratic DCM 100% and then the MeOH concentration was increased from 0.5% to 20%, (silica gel 60 0.004-0.063 mm). The product containing fractions were pooled and the EtOAc was removed by evaporation. The product was not pure and was therefore purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions was pooled and the acetonitrile was removed by evaporation. EtOAc (10 ml) was added and the organic phase was washed with two portions of brine and dried (MgSO4). The solvent was removed by evaporation to give 0.154 g of 2-[(4-{2-[[2-(4-chlorophenyl)ethyl](heptyl)amino]-2-oxoethyl}benzyl)oxy]-benzoic acid (yield 76.8%).

$^1$HNMR (Rotamers, 500 MHz, CDCl$_3$): δ 0.85 (m, 3H), 1.25 (m, 11H), 1.40-1.62 (m, 2H), 2.7-3.7 (bm, 10H), 4.5 (d, 2H), 7-7.4 (bm, 8H).

Example 31

AR-H075135 a) N-Isobutyl-N-[4-(trifluoromethyl)benzyl]amine (0.172 g, 0.746 mol) was dissolved in dry acetonitrile under N2 and N-ethyl-N,N-diisopropylamine (0.371 g, 2.867 mmol) was added. The mixture was stirred for 30 min and methyl 2-{2-[4-(2-chloro-2-oxoethoxy)phenyl]ethoxy}benzoate (0.200 g, 0.573 mmol) was added. The solution was stirred over night at room temperature. The crude was purified by flash chromatography (started with isocratic heptane/EtOAc 50/50 and then the EtOAc concentration was increased to 100%, (silica gel 60 0.004-0.063 mm). The product containing fractions were pooled and the EtOAc was removed by evaporation to give 0.242 g of methyl 2-{2-[4-(2-{isobutyl[4-(trifluoromethyl)benzyl]amino}-2-oxoethoxy)phenyl]ethoxy}benzoate (yield 77.6%).

$^1$HNMR (Rotamers, 500 MHz, CDCl$_3$): δ 0.82-0.97 (bm, 6H, 2.0 (m, 1H), 3.02-3.24 (m, 4H), 3.88 (s, 3H), 4.18 (m, 2H), 4.62-4.8 (m, 4H), 6.78-7.0 (m, 4H), 7.1-7.32 (m, 4H) 7.35-7.62 (m, 3H), 7.78 (d, 1H).

b) Methyl 2-{2-[4-(2-{isobutyl[4-(trifluoromethyl)benzyl]amino}-2-oxoethoxy)phenyl]-ethoxy}benzoate (0.242 g, 0.455 mmol) was dissolved in a mixture of THF (freshly distilled)/water (2/1, 3 ml), lithium hydroxide (0.218 g, 0.909 mmol) was added. The reaction was performed in a single node microwave oven (5 min, 150 deg). THF was removed by evaporation. Water was added (10 ml) and the basic water phase was washed with diethyl ether (2×10 ml). Addition of HCl (2 ml, 1 M, pH 1). The water phase was extracted with two portions of DCM (20 ml), the organic phase was dried (MgSO$_4$) and the solvent was removed by evaporation to give 0.135 g of 2-{2-[4-(2-{isobutyl[4-(trifluoromethyl)benzyl]amino}-2-oxoethoxy)phenyl]ethoxy}benzoic acid (yield 57.3%).

$^1$HNMR (Rotamers, 400 MHz, CDCl$_3$): δ 0.82-0.97 (bm, 6H), 1.98 (m, 1H), 3.06-3.24 (m, 4H), 4.4 (m, 2H), 4.62-4.8 (m, 4H), 6.8 (d, 1H), 6.92 (d, 1H), 7.01 (m, 1H), 7.03-7.22 (m, 3H), 7.27 (m, 2H), 7.5 (m, 2H), 7.58 (d, 1H), 8.1 (d, 1H).

Biological Activity

Formulations

Compounds were dissolved in DMSO to obtain 16 mM stock solutions. Before assays, stock solutions were further diluted in DMSO and culture media General Chemicals and Reagents Luciferase assay reagent was purchased from Packard, USA. Restriction Enzymes were from Boehringer and Vent polymerase from New England Biolabs.

Cell Lines and Cell Culture Conditions

U2-OS, (Osteogenic sarcoma, Human) was purchased from ATCC, USA. Cells were expanded and refrozen in batches from passage number six. Cells were cultured in Dulbecco's modified Eagle medium (DMEM) with 25 mM glucose, 2 mM glutamine or 4 mM L-alanyl-L-glutamine, 10% fetal calf serum, at 5% $CO_2$. Phosphate buffered saline (PBS) without addition of calcium or magnesium was used. All cell culture reagents were from Gibco (USA) and 96-well cell culture plates were purchased from Wallach.

Plasmid Constructs for Heterologous Expression

Standard recombinant DNA techniques were carried out as described by Ausubel (7). The Luciferase reporter vector, pGL5UAS (clone consists of five copies of the GAL4 DNA binding sequence, 5'-CGACGGAGTACTGTCCTC-CGAGCT-3', cloned into the SacI/XhoI sites of pGL3-Promoter (Promega). The SacI/XhoI fragment carrying the UAS sites was constructed using annealed overlapping oligonucleotides.

Expression vectors used are based upon pSG5 (Stratagene). All vectors contain an EcoRI/NheI fragment encoding the DNA binding domain of GAL4 (encoding amino acid positions 1-145 of database accession number P04386) followed by an in-frame fusion to a fragment encoding the nuclear localisation sequence from T antigen of Polyoma Virus. The nuclear localisation sequence was constructed using annealed overlapping oligonucleotides creating NheI/KpnI sticky ends (5'-CTAGCGCTCCTAGAAGAAACG-CAAGGTTGGTAC-3'). The ligand binding domains from human and mouse PPARα and human and mouse PPARγ were PCR amplified as KpnI/BamHI fragments and cloned in frame to the GAL4 DNA binding domain and the nuclear localisation sequence. The sequence of all plasmid constructs used were confirmed by sequencing.

The following expression vectors were used for transient transfections:

| vector | encoded PPAR subtype | sequence reference[1] |
|---|---|---|
| pSGGALhPPa | human PPARα | S74349, nt 625-1530 |
| pSGGALmPPa | murine PPARα | X57638, nt 668-1573 |
| pSGGALhPPg | human PPARγ | U63415, nt 613-1518 |
| pSGGALmPPg | murine PPARγ | U09138, nt 652-1577 |

[1] refers to nucleotide positions of data base entry used to express the ligand binding domain.

Transient Transfections

Frozen stocks of cells from passage number six were thawed and expanded to passage number eight before transfections. Confluent cells were trypsinised, washed and pelleted by centrifugation at 270×g for 2 minutes. The cell pellet was resuspended in cold PBS to a cell concentration of about $18 \times 10^6$ cells/ml. After addition of DNA, the cell suspension was incubated on ice for approximately 5 minutes before electroporation at 230 V, 960 μF in Biorad's Gene Pulser™ in 0.5 ml batches. A total of 50 μg DNA was added to each batch of 0.5 ml cells, including 2.5 μg expression vector, 25 μg reporter vector and 22.5 μg unspecific DNA (pBluescript, Stratagene).

After electroporation, cells were diluted to a concentration of 320,000 cells/ml in DMEM without phenol red, and approximately 25,000 cells/well were seeded in 96-well plates. In order to allow cells to recover, seeded plates were incubated at 37° C. for 3-4 hours before addition of test compounds. In assays for PPARα, the cell medium was supplemented with resin-charcoal stripped fetal calf serum (FCS) in order to avoid background activation by fatty acid components of the FCS. The resin-charcoal stripped FCS was produced as follows; for 500 ml of heat-inactivated FCS, 10 g charcoal and 25 g Bio-Rad Analytical Grade Anion Exchange Resin 200-400 mesh were added, and the solution was kept on a magnetic stirrer at room temperature over night. The following day, the FCS was centrifuged and the stripping procedure was repeated for 4-6 hours. After the second treatment, the FCS was centrifuged and filter sterilised in order to remove remnants of charcoal and resin.

Assay Procedure

Stock solutions of compounds in DMSO were diluted in appropriate concentration ranges in master plates. From master plates, compounds were diluted in culture media to obtain test compound solutions for final doses.

After adjustment of the amount of cell medium to 75 μl in each well, 50 μl test compound solution was added. Transiently transfected cells were exposed to compounds for about 24 hours before the luciferase detection assay was performed. For luciferase assays, 100 μl of assay reagent was added manually to each well and plates were left for approximately 20 minutes in order to allow lysis of the cells. After lysis, luciferase activity was measured in a 1420 Multiwell counter, Victor, from Wallach Reference Compounds The TZD pioglitazone was used as reference substance for activation of both human and murine PPARγ. 5,8,11,14-Eicosatetrayonic acid (ETYA) was used as reference substance for human PPARα.

Calculations and Analysis

For calculation of $EC_{50}$ values, a concentration-effect curve was established. Values used were derived from the average of two or three independent measurements (after subtraction of the background average value) and were expressed as the percentage of the maximal activation obtained by the reference compound. Values were plotted against the logarithm of the test compound concentration. $EC_{50}$ values were estimated by linear intercalation between the data points and calculating the concentration required to achieve 50% of the maximal activation obtained by the reference compound.

The compound of formula I have an $EC_{50}$ of less than 50 μmol/l for PPARα and/or PPARγ. Preferred compounds have an $EC_{50}$ of less than 5 μmol/l for either PPARα or PPARγ. For example, Example 2 has an $EC_{50}$ of 2.96 μmol/l for human PPAR alpha and an $EC_{50}$ of 3.05 μmol/l for mouse PPAR gamma.

What is claimed is:

1. A compound of formula I

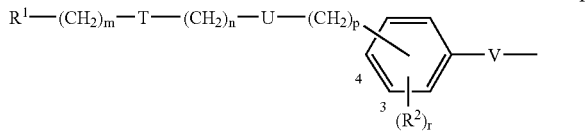

-continued

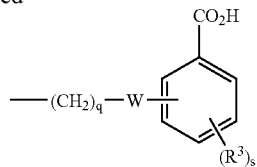

wherein:
R¹ represents aryl optionally substituted by a heterocyclic group or a heterocyclic group optionally substituted by aryl wherein each aryl or heterocyclic group is optionally substituted by one or more of the following groups:
a $C_{1-6}$alkyl group;
a $C_{1-6}$acyl group;
aryl$C_{1-6}$alkyl, wherein the alkyl, aryl, or alkylaryl group is optionally substituted by one or more $R^b$;
halogen;
—CN and $NO_2$;
—$NR^cCOOR^a$;
—$NR^cCOR^a$;
—$NR^cR^a$;
—$NR^cSO_2R^d$;
—$NR^cCONR^kR^c$;
—$NR^cCSNR^aR^k$;
—$OR^a$;
—$OSO_2R^d$;
—$SO_2R^d$;
—$SOR^d$;
—$SR^c$;
—$SO_2NR^aR^f$;
—$SO_2OR^a$;
—$CONR^cR^a$;
—$OCONR^fR^a$;
wherein $R^a$ represents H, a $C_{1-6}$alkyl group, aryl or aryl$C_{1-6}$alky group wherein the alkyl, aryl or aryl$C_{1-6}$alkyl group is optionally substituted one or more times by $R^b$, wherein $R^b$ represents $C_{1-6}$alkyl, aryl, aryl$C_{1-6}$alkyl, cyano, —$NR^cR^d$, =O, halo, —OH, —SH, -$OC_{1-4}$alkyl, —Oaryl, —$OC_{1-4}$alkylaryl, —$COR^c$, —$SR^d$, —$SOR^d$, or —$SO_2R^d$, wherein $R^c$ represents H, $C_{1-4}$alkyl, aryl, aryl$C_{1-4}$alkyl and $R^d$ represents $C_{1-4}$alkyl, aryl, aryl$C_{1-4}$alkyl;
wherein $R^f$ represents hydrogen, $C_{1-4}$alkyl, $C_{1-4}$acyl, aryl, aryl$C_{1-4}$alkyl and $R^a$ is as defined above; and
$R^k$ represents hydrogen, $C_{1-4}$alkyl, aryl, aryl $C_{1-4}$alkyl;
the group —$(CH_2)_m$-T-$(CH_2)_n$—U—$(CH_2)_p$— is attached at either the 3 or 4 position in the phenyl ring as indicated by the numbers in formula I and represents a group selected from one or more of the following: $O(CH_2)_2$, $O(CH_2)_3$, $NC(O)NR^4(CH_2)_2$, $CH_2S(O_2)NR^5(CH_2)_2$, $CH_2N(R^6)C(O)CH_2$, $(CH_2)_2N(R^6)C(O)(CH_2)_2$, $C(O)NR^7CH_2$, $C(O)NR^7(CH_2)_2$, and $CH_2N(R^6)C(O)CH_2O$;
V represents O;
q represents 1;
W represents a single bond;
$R^2$ represents halo, a $C_{1-4}$alkyl group which is optionally substituted by one or more fluoro, a $C_{1-4}$alkoxy group which is optionally substituted by one or more fluoro, a $C_{1-4}$acyl group, aryl, an aryl$C_{1-4}$alkyl group, CN or $NO_2$;
r represents 0, 1, 2 or 3;
$R^3$ represents halo, a $C_{1-4}$akyl group which is optionally substituted by one or more fluoro, a $C_{1-4}$alkoxy group which is optionally substituted by one or more fluoro, a $C_{1-4}$acyl group, aryl, an aryl$C_{1-4}$alkyl group, or CN;
s represents 0, 1, 2 or 3; and
$R^4$, $R^5$, $R^6$, $R^7$, $R^8$, $R^9$ and $R^{10}$ independently represent H, a $C_{1-10}$alkyl group, aryl or an aryl$C_{1-4}$alkyl group or when m is 0 and T represents a group $N(R^6)C(O)$ or a group $(R^5)NS(O_2)$ then $R^1$ and $R^6$ or $R^1$ and $R^5$ together with the nitrogen atom to which they are attached represent a heteroaryl group;
or a pharmaceutically acceptable salts thereof;
with the proviso that:
1) when $R^1$ is phenyl optionally substituted by one or two groups independently selected from halo, a $C_{1-4}$alkyl group which is optionally substituted by one or more fluoro, a is $C_{1-4}$alkoxy group which is optionally substituted by one or more fluoro;
m is 1;
T is $N(R^6)C(O)$ wherein $R^6$ represents a $C_{2-8}$alkyl group which is optionally interrupted by oxygen;
n is 1;
U is absent or represents methylene;
p is 0;
r is 0;
V is O;
q is 1; and
W is a single bond attached to the position ortho to the carboxylic acid group;
then s does not represent 0;
wherein the group —V—$(CH_2)_q$—W— is joined at the ortho position with respect to the carboxylic acid group.

2. A compound selected from one or more of the following:
2-{[4-(2-oxo-2-{[4-(trifluoromethyl)benzyl]amino)ethyl)phenoxy]methyl}benzoic acid;
2-[(3-{2-[benzyl(hexyl)amino]-2-oxoethyl}phenoxy)methyl]benzoic acid;
2- {[3-(2-oxo-2-{[4-(trifluoromethyl)benzyl]amino}ethyl)phenoxy]methyl}benzoic acid;
2-[(4-{3-[[2-(3,4-dimethoxyphenyl)ethyl](methyl)amino]-3-oxopropyl}phenoxy)-15 methyl]benzoic acid;
2-[(4-{2-[({4-methyl-2-[4-(trifluoromethyl)phenyl]-1,3-thiazol-5-yl}carbonyl)amino]-ethyl}phenoxy)methyl]benzoic acid;
2-({4-[2-({[(2,4-difluorophenyl)amino]carbonyl}amino)ethyl]phenoxy}methyl)benzoic acid;
2-[(4-{2-[(2-methyl-5-phenyl-3-furoyl)amino]ethyl}phenoxy)methyl]benzoic acid;
2-[(4-{2-[(benzylsulfonyl)amino]ethyl}phenoxy)methyl]benzoic acid;
2-[(4-{2-[benzyl(hexyl)amino]-2-oxoethyl}-2-fluorophenoxy)methyl]benzoic acid;
2-[(4-{2-[benzyl(hexyl)amino]-2-oxoethyl}-2-methoxyphenoxy)methyl]benzoic acid;
2-({4-[3-(3,4-dihydroisoquinolin-2(1H)-yl)-3-oxopropyl]phenoxy)methyl)benzoic acid;
2-[(4-{2-[4-(1H-imidazol-1-yl)phenoxy]ethyl)-phenoxymethyl]benzoic acid;
2-([4-{2-{4-[(methylsulfonyl)oxy]phenoxy}ethyl)phenoxy]methyl}benzoic acid;
2-[(3-{2-[4-(benzyloxy)phenoxy]ethyl}phenoxy)methyl]benzoic acid;
2-{[3-(2-{4-[(methylsulfonyl)oxy]phenoxy}ethyl )phenoxy]methyl}benzoic acid;
2-({3-[2-(4-hydroxyphenoxy)ethyl]phenoxy}methyl)benzoic acid;
2-[(4-{3-[4-(benzyloxy)phenoxy]propyl}phenoxy)methyl]benzoic acid;

2-{[4-(3-{4-[(methylsulfonyl)oxy]phenoxy}propyl)phenoxy]methyl}benzoic acid;
2-({4-[3-(4-hydroxyphenoxy)propyl]phenoxy}methyl) benzoic acid;
2-{[4-(3-{[2-(2-ethoxyphenyl)ethyl]amino}-3-oxopropyl)phenoxy]methyl}benzoic acid;
2-[(4-{3-[ethyl(2-pyridin-2-ylethyl)amino]-3-oxopropyl}phenoxy)methyl]benzoic acid;
2-{[4-(2-{heptyl[2-(2-methoxyphenyl)ethyl]amino}-2-oxoethyl)phenoxy]methyl}benzoic acid;
2-[(4-{2-[[2-(4-chlorophenyl)ethyl](heptyl)amino]-2-oxoethyl}phenoxy)methyl]benzoic acid;
2-[(4-{2-[heptyl(2-phenylethyl)amino]-2-oxoethyl}-phenoxy)methyl]benzoic acid; and
2-[(4-{2-[ethyl(2-fluorobenzyl)amino]-2-oxoethoxy}phenoxy)methyl]benzoic acid;
or a pharmaceutically acceptable salt thereof.

3. A pharmaceutical formulation comprising a compound according to claim 1 in admixture with a pharmaceutically acceptable adjuvant, diluent, and/or carrier.

4. A method of treating insulin resistance comprising the administration of a compound to a mammal in need thereof, wherein the compound is of formula I

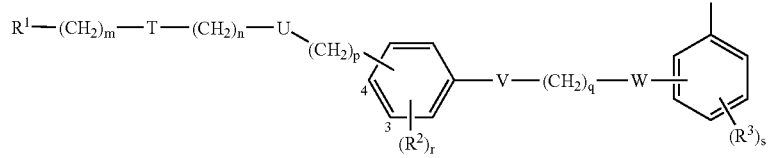

wherein:
R$^1$ represents aryl optionally substituted by a heterocyclic group or a heterocyclic group optionally substituted by aryl wherein each aryl or heterocyclic group is optionally substituted by one or more of the following groups:
a C$_{1-6}$alkyl group;
a C$_{1-6}$acyl group;
arylC$_{1-6}$alkyl, wherein the alkyl, aryl, or alkylaryl group is optionally substituted by one or more R$^b$;
halogen;
—CN and NO$_2$;
—NR$^c$COOR$^a$;
—NR$^c$COR$^a$;
—NR$^c$R$^a$;
—NR$^c$SO$_2$R$^d$;
—NR$^c$CONR$^k$R$^c$;
—NR$^c$CSNR$^a$R$^k$;
—OR$^a$;
—OSO$_2$R$^d$;
—SO$_2$R$^d$;
—SOR$^d$;
—SR$^c$;
—SO$_2$NR$^a$R$^f$;
—SO$_2$OR$^a$;
—CONR$^c$R$^a$;
—OCONR$^f$R$^a$;
wherein R$^a$ represents H, a C$_{1-6}$alkyl group, aryl or arylC$_{1-6}$ alky group wherein the alkyl, aryl or arylC$_{1-6}$alkyl group is optionally substituted one or more times by R$^b$, wherein R$^b$ represents C$_{1-6}$alkyl, aryl, arylC$_{1-6}$alkyl, cyano, —NR$^c$R$^d$, ═O, halo, —OH, —SH, —OC$_{1-4}$ alkyl, —Oaryl, —OC$_{1-4}$alkylaryl, —COR$^c$, —SR$^d$, —SOR$^d$, or —SO$_2$R$^d$, wherein R$^c$ represents H, C$_{1-4}$alkyl, aryl, arylC$_{1-4}$alkyl and R$^d$ represents C$_{1-4}$alkyl, aryl, arylC$_{1-4}$alkyl;
wherein R$^f$ represents hydrogen, C$_{1-4}$alkyl, C$_{1-4}$acyl, aryl, arylC$_{1-4}$alkyl and R$^a$ is as defined above; and
R$^k$ represents hydrogen, C$_{1-4}$alkyl, aryl, aryl C$_{1-4}$alkyl;
the group —(CH$_2$)$_m$-T-(CH$_2$)$_n$—U—(CH$_2$)$_p$— is attached at either the 3 or 4 position in the phenyl ring as indicated by the numbers in formula I and represents a group selected from one or more of the following: O(CH$_2$)$_2$, O(CH$_2$)$_3$, NC(O)NR$^4$(CH$_2$)$_2$, CH$_2$S(O$_2$)NR$^5$(CH$_2$)$_2$, CH$_2$N(R$^6$)C(O)CH$_2$, (CH$_2$)$_2$N(R$^6$)C(O)(CH$_2$)$_2$, C(O)NR$^7$CH$_2$, C(O)NR$_7$(CH$_2$)$_2$, and CH$_2$N(R$^6$)C(O)CH$_2$O;
V represents O;
q represents 1;
W represents a single bond;
R$^2$ represents halo, a C$_{1-4}$alkyl group which is optionally substituted by one or more Fluoro, a C$_{1-4}$alkoxy group which is optionally substituted by one or more fluoro, a C$_{1-4}$acyl group, aryl, an arylC$_{1-4}$alkyl group, CN or NO$_2$;
r represents 0, 1, 2 or 3;
R$^3$ represents halo, a C$_{1-4}$akyl group which is optionally substituted by one or more fluoro, a C$_{1-4}$alkoxy group which is optionally substituted by one or more fluoro, a C$_{1-4}$acyl group, aryl, an arylC$_{1-4}$alkyl group, or CN;
s represents 0, 1, 2 or 3; and
R$^4$, R$^5$, R$^6$, R$^7$, R$^8$, R$^9$ and R$^{10}$ independently represent H, a C$_{1-10}$alkyl group, aryl or an arylC$_{1-4}$alkyl group or when m is 0 and T represents a group N(R$^6$)C(O) or a group (R$^5$)NS(O$_2$) then R$^1$ and R$^6$ or R$^1$ and R$^5$ together with the nitrogen atom to which they are attached represent a heteroaryl group;
or a pharmaceutically acceptable salts thereof;
with the proviso that:
1) when R$^1$ is phenyl optionally substituted by one or two groups independently selected from halo, a C$_{1-4}$alkyl group which is optionally substituted by one or more fluoro, a is C$_{1-4}$alkoxy group which is optionally substituted by one or more fluoro;
m is 1;
T is N(R$^6$)C(O) wherein R$^6$ represents a C$_{2-8}$alkyl group which is optionally interrupted by oxygen;
n is 1;
U is absent or represents methylene;
p is 0;
r is 0;
V is O;
q is 1; and
W is a single bond attached to the position ortho to the carboxylic acid group;
then s does not represent 0.

5. The method of claim 4 wherein the group —V—$(CH_2)_q$—W— of the compound is joined at the ortho position with respect to the carboxylic acid group.

6. The method of claim 4 wherein the compound is chosen from:
- 2-{[4-(2-oxo-2-{[4-(trifluoromethyl)benzyl]amino)ethyl)phenoxy]methyl}benzoic acid;
- 2-[(3-{2-[benzyl(hexyl)amino]-2-oxoethyl}phenoxy)methyl]benzoic acid;
- 2-{[3-(2-oxo-2-{[4-(trifluoromethyl)benzyl]amino}ethyl)phenoxy]15 methyl}benzoic acid;
- 2-[(4-{3-[[2-(3,4-dimethoxyphenyl)ethyl](methyl)amino]-3-oxopropyl}phenoxy)-methyl]benzoic acid;
- 2-[(4-{2-[({4-methyl-2-[4-(trifluoromethyl)phenyl]-1,3-thiazol-5-yl}carbonyl)amino]-ethyl}phenoxy)methyl]benzoic acid;
- 2-({4-[2-({[(2,4-difluorophenyl)amino]carbonyl}amino)ethyl]phenoxy}methyl) benzoic acid;
- 2-[(4-{2-[(2-methyl-5-phenyl-3-furoyl)amino]ethyl}phenoxy)methyl]benzoic acid;
- 2-[(4-{2-[(benzylsulfonyl)amino]ethyl}phenoxy)methyl]benzoic acid;
- 2-[(4-{2-[benzyl(hexyl)amino]-2-oxoethyl}-2-fluorophenoxy)methyl]benzoic acid;
- 2-[(4-{2-[benzyl(hexyl)amino]-2-oxoethyl}-2-methoxyphenoxy)methyl]benzoic acid;
- 2-({4-[3-(3,4-dihydroisoquinolin-2(1H)-yl)-3-oxopropyl]phenoxy)methyl)benzoic acid;
- 2-[(4-{2-[4-(1H-imidazol-1-yl)phenoxy]ethyl)-phenoxymethyl]benzoic acid;
- 2-([4-{2-{4-[(methylsulfonyl)oxy]phenoxy}ethyl)phenoxy]methyl}benzoic acid;
- 2-[(3-{2-[4-(benzyloxy)phenoxy]ethyl}phenoxy)methyl]benzoic acid;
- 2-{[3-(2-{4-[(methylsulfonyl)oxy]phenoxy}ethyl)phenoxy]methyl}benzoic acid;
- 2-({3-[2-(4-hydroxyphenoxy)ethyl]phenoxy}methyl)benzoic acid;
- 2-[(4-{3-[4-(benzyloxy)phenoxy]propyl}phenoxy)methyl]benzoic acid;
- 2-{[4-(3-{4-[(methylsulfonyl)oxy]phenoxy}propyl)phenoxy]methyl}benzoic acid;
- 2-({4-[3-(4-hydroxyphenoxy)propyl]phenoxy}methyl) benzoic acid;
- 2-{[4-(3-{[2-(2-ethoxyphenyl)ethyl]amino}-3-oxopropyl)phenoxy]methyl}benzoic acid;
- 2-[(4-{3-[ethyl(2-pyridin-2-ylethyl)amino]-3-oxopropyl}phenoxy)methyl]benzoic acid;
- 2-{[4-(2-{heptyl[2-(2-methoxyphenyl)ethyl]amino}-2-oxoethyl)phenoxy]methyl}benzoic acid;
- 2-[(4-{2-[[2-(4-chlorophenyl)ethyl](heptyl)amino]-2-oxoethyl}phenoxy)methyl]benzoic acid;
- 2-[(4-{2-[heptyl(2-phenylethyl)amino]-2-oxoethyl}-phenoxy)methyl]benzoic acid; and
- 2-[(4-{2-[ethyl(2-fluorobenzyl)amino]-2-oxoethoxy}phenoxy)methyl]benzoic acid;

or a pharmaceutically acceptable salt thereof.

7. The method of claim 4 wherein $R^1$ represents phenyl which is optionally substituted by one or more of the following: halo, hydroxy, a $C_{1-4}$alkyl group which is optionally substituted by one or more fluoro, a $C_{1-4}$alkoxy group which is optionally substituted by one or more fluoro, benzyloxy, a $C_{1-4}$alkylsulphonyloxy group, phenyl or a heteroaryl group, or $R^1$ represents heteroaryl which is optionally substituted by one or more of the following: halo, a $C_{1-4}$alkyl group which is optionally substituted by one or more fluoro, a $C_{1-4}$alkoxy group which is optionally substituted by one or more fluoro or phenyl optionally substituted by one or more of the following: halo, a $C_{1-4}$alkyl group which is optionally substituted by one or more fluoro, a $C_{1-4}$alkoxy group which is optionally substituted by one or more fluoro.

8. The method of claim 4 wherein the group —$(CH_2)_m$-T-$(CH_2)_n$—U—$(CH_2)_p$— is attached at the 4 position in the phenyl ring as indicated by the numbers in formula I, that is para to the group V.

9. The method of claim 4 wherein $R^2$ is halo, a $C_{1-4}$alkyl group or a $C_{1-4}$alkoxy group and r is 0 or 1.

10. The method of claim 4 wherein s is 0.

* * * * *

UNITED STATES PATENT AND TRADEMARK OFFICE
CERTIFICATE OF CORRECTION

PATENT NO. : 7,521,461 B2  Page 1 of 1
APPLICATION NO. : 10/518819
DATED : April 21, 2009
INVENTOR(S) : Lanna Li It is certified that error appears in the above-identified patent and that said Letters Patent is hereby corrected as shown below:

At Columns 61 and 62, Claim 4, between Lines 24-35, as part of the chemical structure, "COPG" should read -- $CO_2H$ -- and should have been depicted as follows:

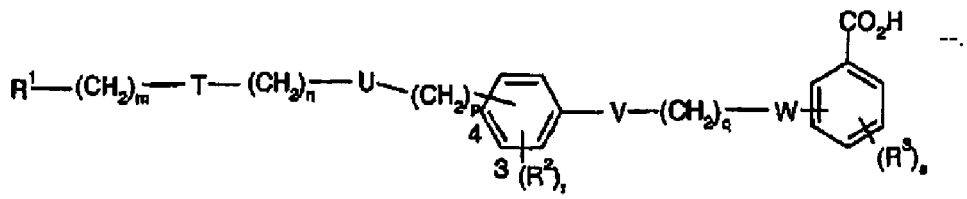

Column 63, Line 11:

"amino}ethyl)phenoxy]15 methyl}benzoic acid"
should read -- amino}ethyl)phenoxy] methyl}benzoic acid --.

Signed and Sealed this

Sixteenth Day of June, 2009

JOHN DOLL
*Acting Director of the United States Patent and Trademark Office*